United States Patent
Darty

(10) Patent No.: US 10,448,836 B2
(45) Date of Patent: Oct. 22, 2019

(54) METHODS AND APPARATUS FOR COAXIAL IMAGING OF MULTIPLE WAVELENGTHS

(71) Applicant: Hypermed Imaging, Inc., Memphis, TN (US)

(72) Inventor: Mark Anthony Darty, Collierville, TN (US)

(73) Assignee: Hypermed Imaging, Inc., Memphis, TN (US)

(*) Notice: Subject to any disclaimer, the term of this patent is extended or adjusted under 35 U.S.C. 154(b) by 0 days.

(21) Appl. No.: 15/143,399

(22) Filed: Apr. 29, 2016

(65) Prior Publication Data

US 2016/0345835 A1  Dec. 1, 2016

Related U.S. Application Data

(63) Continuation of application No. 14/333,406, filed on Jul. 16, 2014, now Pat. No. 9,354,115, which is a
(Continued)

(51) Int. Cl.
*A61B 5/00* (2006.01)
*G01J 3/02* (2006.01)
(Continued)

(52) U.S. Cl.
CPC ............ *A61B 5/0075* (2013.01); *A61B 5/443* (2013.01); *A61B 5/447* (2013.01); *A61B 5/4869* (2013.01);
(Continued)

(58) Field of Classification Search
CPC ...... G01J 3/10; G01J 3/12; G01J 3/447; G01J 3/0208; G01J 3/2823; G01J 3/36;
(Continued)

(56) References Cited

U.S. PATENT DOCUMENTS 4,845,010 A * 7/1989 Coppens ............... G03C 1/005
                                                            430/204
5,276,321 A   1/1994 Chang et al.
(Continued)

FOREIGN PATENT DOCUMENTS

EP           2359745        8/2011
WO     WO 2008-100582      8/2008
WO     WO 2011-070357      6/2011

OTHER PUBLICATIONS

Supplementary European Search Report for Application No. EP 13 81 3563 dated Feb. 5, 2016.
(Continued)

*Primary Examiner* — Mohamed K Amara
(74) *Attorney, Agent, or Firm* — Morgan, Lewis & Bockius LLP

(57) ABSTRACT

A hyperspectral/multispectral imager comprising a housing is provided. At least one light source is attached to the housing. An objective lens, in an optical communication path comprising originating and terminating ends, is further attached to the housing and causes light to (i) be backscattered by the tissue of a subject at the originating end and then (ii) pass through the objective lens to a beam steering element at the terminating end of the communication path inside the housing. The beam steering element has a plurality of operating modes each of which causes the element to be in optical communication with a different optical detector in a plurality of optical detectors offset from the optical communication path. Each respective detector filter in a plurality of detector filters covers a corresponding optical detector in the plurality of optical detectors thereby filtering light received by the corresponding detector from the beam steering element.

22 Claims, 19 Drawing Sheets

Related U.S. Application Data continuation of application No. PCT/US2013/032682, filed on Mar. 15, 2013.

(60) Provisional application No. 61/655,800, filed on Jun. 5, 2012.

(51) Int. Cl.

| | |
|---|---|
| *G01J 3/28* | (2006.01) |
| *G01J 3/36* | (2006.01) |
| *G01N 21/25* | (2006.01) |
| *G01N 21/31* | (2006.01) |
| *G01N 21/47* | (2006.01) |
| *G01J 3/447* | (2006.01) |
| *A61B 90/30* | (2016.01) |
| *A61B 90/00* | (2016.01) |
| *G01J 3/10* | (2006.01) |
| *G01J 3/12* | (2006.01) |

(52) U.S. Cl.
CPC ............ *A61B 90/30* (2016.02); *A61B 90/361* (2016.02); *G01J 3/021* (2013.01); *G01J 3/0208* (2013.01); *G01J 3/0224* (2013.01); *G01J 3/0291* (2013.01); *G01J 3/10* (2013.01); *G01J 3/12* (2013.01); *G01J 3/2803* (2013.01); *G01J 3/2823* (2013.01); *G01J 3/36* (2013.01); *G01J 3/447* (2013.01); *G01N 21/255* (2013.01); *G01N 21/31* (2013.01); *G01N 21/47* (2013.01); *A61B 2090/309* (2016.02); *A61B 2090/3618* (2016.02); *A61B 2560/0425* (2013.01); *A61B 2562/028* (2013.01); *A61B 2562/0233* (2013.01); *G01J 2003/1213* (2013.01); *G01J 2003/2826* (2013.01); *G01N 2021/4709* (2013.01)

(58) Field of Classification Search
CPC ........ G01J 3/0291; G01J 3/021; G01J 3/0224; G01J 3/2803; G01J 2003/2826; G01J 2003/1213; A61B 90/30; A61B 5/447; A61B 5/443; A61B 5/4869; A61B 5/0079; A61B 2562/028; A61B 2090/309; A61B 2090/3618; A61B 2562/0233; A61B 2560/0425; A61B 5/0075; A61B 90/361; A61B 5/1455; G01N 21/47; G01N 21/255; G01N 21/31; G01N 2003/2826; G01N 2021/4709

See application file for complete search history.

(56) References Cited

U.S. PATENT DOCUMENTS

| | | | |
|---|---|---|---|
| 6,081,612 A | 6/2000 | Gutkowicz-Krushin et al. | |
| 6,504,943 B1 | 1/2003 | Sweatt et al. | |
| 6,735,507 B2 | 5/2004 | Kudryashov et al. | |
| 6,826,424 B1* | 11/2004 | Zeng | G01J 3/0289 |
| | | | 600/407 |
| 6,975,898 B2* | 12/2005 | Seibel | A61B 1/00048 |
| | | | 600/473 |
| 7,869,032 B2 | 1/2011 | Jones et al. | |
| 8,320,650 B2 | 11/2012 | Demos et al. | |
| 8,406,859 B2 | 3/2013 | Zuzak et al. | |
| 9,551,616 B2* | 1/2017 | McQuilkin | G01J 3/2803 |
| 9,642,532 B2* | 5/2017 | Fengler | A61B 1/00186 |
| 9,706,953 B2* | 7/2017 | Saito | A61B 1/00009 |
| 2002/0049386 A1* | 4/2002 | Yang | A61B 5/0059 |
| | | | 600/476 |
| 2002/0049683 A1 | 4/2002 | Yang et al. | |
| 2003/0036855 A1* | 2/2003 | Harris | G02B 21/0028 |
| | | | 702/19 |
| 2003/0139886 A1* | 7/2003 | Bodzin | G01N 21/47 |
| | | | 702/28 |
| 2003/0231159 A1* | 12/2003 | Dalal | G09G 3/342 |
| | | | 345/102 |
| 2005/0075575 A1* | 4/2005 | Vo-Dinh | G01N 21/6408 |
| | | | 600/476 |
| 2005/0154277 A1 | 7/2005 | Tang et al. | |
| 2005/0234302 A1* | 10/2005 | MacKinnon | A61B 1/00186 |
| | | | 600/181 |
| 2005/0270528 A1* | 12/2005 | Geshwind | G01J 3/02 |
| | | | 356/330 |
| 2006/0273245 A1* | 12/2006 | Kim | G01J 3/0259 |
| | | | 250/226 |
| 2007/0002276 A1* | 1/2007 | Hirohara | A61B 5/14555 |
| | | | 351/206 |
| 2007/0016079 A1* | 1/2007 | Freeman | A61B 5/0059 |
| | | | 600/476 |
| 2007/0092107 A1* | 4/2007 | Danielson | G07C 9/00158 |
| | | | 382/100 |
| 2007/0114362 A1* | 5/2007 | Feng | G01N 21/6428 |
| | | | 250/208.1 |
| 2008/0068604 A1 | 3/2008 | Grossinger et al. | |
| 2008/0135739 A1* | 6/2008 | Kim | G01J 3/02 |
| | | | 250/226 |
| 2008/0267472 A1 | 10/2008 | Demos | |
| 2008/0306337 A1 | 12/2008 | Livingston et al. | |
| 2009/0122313 A1* | 5/2009 | Jones | G01N 15/0205 |
| | | | 356/326 |
| 2009/0318815 A1* | 12/2009 | Barnes | A61B 5/742 |
| | | | 600/473 |
| 2009/0326383 A1* | 12/2009 | Barnes | A61B 5/0059 |
| | | | 600/476 |
| 2010/0056928 A1* | 3/2010 | Zuzak | A61B 5/0071 |
| | | | 600/476 |
| 2010/0110170 A1* | 5/2010 | Bringer | G06K 9/00046 |
| | | | 348/77 |
| 2010/0193704 A1* | 8/2010 | Pratt | G01J 3/4406 |
| | | | 250/459.1 |
| 2010/0195097 A1* | 8/2010 | Wenz | G01N 21/4738 |
| | | | 356/237.5 |
| 2010/0245616 A1 | 9/2010 | Yoshino et al. | |
| 2011/0028790 A1* | 2/2011 | Farr | A61B 1/00052 |
| | | | 348/77 |
| 2011/0118547 A1 | 5/2011 | Erikawa | |
| 2011/0205536 A1* | 8/2011 | Johnsen | G01J 3/06 |
| | | | 356/326 |
| 2012/0140240 A1* | 6/2012 | Hillman | G01N 21/4795 |
| | | | 356/496 |
| 2013/0015370 A1* | 1/2013 | Damaskinos | G01N 21/6452 |
| | | | 250/459.1 |
| 2013/0076910 A1* | 3/2013 | Scott | H04N 5/332 |
| | | | 348/164 |
| 2013/0128227 A1 | 5/2013 | Cui et al. | |
| 2013/0296709 A1* | 11/2013 | Zuzak | A61B 5/0071 |
| | | | 600/476 |
| 2015/0044098 A1* | 2/2015 | Smart | A61B 5/0013 |
| | | | 422/82.05 |
| 2016/0198961 A1* | 7/2016 | Homyk | A61B 5/0082 |
| | | | 600/476 |
| 2016/0202178 A1* | 7/2016 | Acosta | G01N 21/27 |
| | | | 356/303 |
| 2016/0249810 A1* | 9/2016 | Darty | A61B 5/0075 |
| | | | 600/477 |
| 2017/0243079 A1* | 8/2017 | Hiriyannaiah | G06K 9/209 |
| 2017/0303838 A1* | 10/2017 | Brill | A61B 5/0071 |
| 2017/0340212 A1* | 11/2017 | Lin | A61B 5/14551 |
| 2018/0252647 A1* | 9/2018 | Levitz | G01N 21/21 |
| 2019/0069824 A1* | 3/2019 | Darty | A61B 1/04 |
| 2019/0149749 A1* | 5/2019 | Darty | G01J 3/0294 |

OTHER PUBLICATIONS

U.S. Appl. No. 14/372,711, 2015-0051498, U.S. Pat. No. 9,107,624, Granted, filed Jul. 16, 2014, Feb. 19, 2015, Aug. 18, 2015.
U.S. Appl. No. 14/333,406, 2015-0308896, U.S. Pat. No. 9,354,115, Granted, filed Jul. 16, 2014, Oct. 29, 2015, May 31, 2016.

(56) References Cited

OTHER PUBLICATIONS

Riza, Nabel A., "Digital Micro-Mirror Device-Based Broadband Optical Image Sensor for Robust Imaging Applications", Optics Communications, 284 (2011) 103-111.

* cited by examiner

METHODS AND APPARATUS FOR COAXIAL IMAGING OF MULTIPLE WAVELENGTHS

CROSS-REFERENCE TO RELATED APPLICATION

This application is a continuation of U.S. patent application Ser. No. 14/333,406, filed Jul. 16, 2014, issued as U.S. Pat. No. 9,354,115, which is a continuation of International Patent Application No. PCT/US2013/032682, filed on Mar. 15, 2013, which claims priority to U.S. Provisional Patent Application Ser. No. 61/655,800, filed Jun. 5, 2012, the disclosures of which are hereby incorporated herein by reference in their entireties for all purposes.

FIELD OF THE APPLICATION

This application generally relates to systems and methods for hyperspectral/multi spectral imaging.

BACKGROUND

Hyperspectral/multispectral spectroscopy is an imaging technique that integrates multiples images of an object resolved at different narrow spectral bands (e.g., narrow ranges of wavelengths) into a single data cube, referred to as a hyperspectral/multispectral data cube. Data provided by hyperspectral/multispectral spectroscopy allow for the identification of individual components of a complex composition through the recognition of hyperspectral/multispectral signatures for individual components within the hyperspectral/multispectral data cube.

Hyperspectral/multispectral spectroscopy has been used for a variety of applications, ranging from geological and agricultural surveying to military surveillance and industrial evaluation. For example, satellite hyperspectral/multispectral imaging has been used in mineral exploration, environmental monitoring and military surveillance. (See, Bowles J. H. et al., Imaging Spectrometry III; 1997: Proc SPIE 1997. p. 38-45; Riaza A. et al., Inteml J Applied Earth Observation and Geoinformation Special issue: Applications of imaging spectroscopy 2001; 3-4:345-354; Thenkabail P. S. et al., Remote Sens Environ 2000; 71 (REMOTE SENS ENVIRON): 158-182., and Tran C. D., Fresenius J Anal Chem 2001; 369(3-4):313-9, the contents of which are hereby incorporated herein by reference in their entireties for all purposes.)

Hyperspectral/multispectral spectroscopy has also been used in medical applications to assist with complex diagnosis and predict treatment outcomes. For example, medical hyperspectral/multispectral imaging has been used to accurately predict viability and survival of tissue deprived of adequate perfusion, and to differentiate diseased (e.g. tumor) and ischemic tissue from normal tissue. (See, Colarusso P. et al., Appl Spectrosc 1998; 52:106A-120A; Greenman R. I. et al., Lancet 2005; 366:1711-1718; and Zuzak K. J. et al., Circulation 2001; 104(24):2905-10; the contents of which are hereby incorporated herein by reference in their entireties for all purposes.)

Despite the great potential hyperspectral/multispectral spectroscopy holds for medical imaging, several drawbacks have limited its use in the clinic setting (Kester R. T. et al., J. Biomed. Opt. 16, 056005 (May 10, 2011)). For example, medical hyperspectral/multispectral instruments are costly, typically tens to hundreds of thousands of dollars, due to the complex optics required to resolve images at a plurality of narrow spectral bands.

Hyperspectral/multispectral imaging can also suffer from poor temporal and spatial resolution, as well as low optical throughput, due to the complex optics and taxing computational requirements for assembling, processing, and analyzing data into three-dimensional hyperspectral/multispectral data cubes.

Thus, there is an unmet need in the field for less expensive and more rapid means of hyperspectral/multispectral imaging and data analysis. The present disclosure meets these and other needs by providing methods and systems for co-axial hyperspectral/multispectral imaging.

SUMMARY

Certain aspects of the application provide methods and systems for co-axial hyperspectral/multispectral imaging. In particular embodiments, the methods and systems are based on a specific architectural arrangement of the internal hardware of a hyperspectral/multispectral imaging system, which serves to direct and resolve light of multiple wavelengths in a co-axial fashion. In a particular embodiment, a beam steering element having a plurality of operating modes directs light of different wavelengths to distinct optical detectors from a common point of origin, thus maintaining co-axial alignment between images captured by the respective optical detectors.

In one aspect, the present disclosure provides a hyperspectral/multispectral imaging device. One embodiment provides a hyperspectral/multispectral imaging device comprising a housing having an exterior and an interior and at least one objective lens attached to or within the housing. The at least one objective lens is disposed in an optical communication path comprising an originating end and a terminating end. The hyperspectral/multispectral imaging device further comprises a beam steering element within the interior of the housing. The beam steering element is in optical communication with the at least one objective lens and is positioned at the terminating end of the optical communication path. The beam steering element is characterized by a plurality of operating modes. Each respective operating mode in the plurality of operating modes causes the beam steering element to be in optical communication with a different optical detector.

The hyperspectral/multispectral imaging device further comprises a plurality of optical detectors offset from the optical communication path. Each respective optical detector in the plurality of optical detectors is in optical communication with a corresponding operating mode of the beam steering element. The hyperspectral/multispectral imaging device further comprises a plurality of detector filters within the housing. Each respective detector filter in the plurality of detector filters covers a corresponding optical detector in the plurality of optical detectors thereby filtering light received by the corresponding optical detector from the beam steering element.

The hyperspectral/multispectral imaging device further comprises at least one processor within the interior of the housing. The at least one processor is in electrical communication with the beam steering element and the plurality of optical detectors. There is a non-transitory memory within the interior of the housing and at least one program is stored in the memory and is executable by the at least one processor.

The at least one program comprises instructions for (i) switching the beam steering element between operating modes in the plurality of operating modes, and (ii) controlling each optical detector in the plurality of optical detectors.

There is a communication interface in electrical communication with the at least one processor. In a specific embodiment, the hyperspectral/multispectral imaging device further comprises at least one light source for illuminating a target object or subject.

In another aspect, the present disclosure provides a hyperspectral/multispectral camera for medical imaging. One embodiment provides a hyperspectral/multispectral imaging device comprising a housing having an exterior and an interior and at least one light source disposed on the exterior of the housing. The hyperspectral/multispectral imaging device comprises at least one objective lens attached to or within the housing. The at least one objective lens is disposed in an optical communication path. The optical communication path comprises an originating end and a terminating end. The at least one light source is offset from the optical communication path and is positioned so that light from the at least one light source is (i) first backscattered by a surface of a patient positioned at the originating end of the optical communication path and (ii) then passed from the originating end of the optical communication path, through the at least one objective lens, and to the terminating end of the optical communication path. The hyperspectral/multispectral imaging device further comprises a beam steering element within the interior of the housing. The beam steering element is in optical communication with the at least one objective lens and is positioned at the terminating end of the optical communication path. The beam steering element is characterized by a plurality of operating modes. Each respective operating mode in the plurality of operating modes causes the beam steering element to be in optical communication with a different optical detector. The hyperspectral/multispectral imaging device further comprises a plurality of optical detectors offset from the optical communication path. Each respective optical detector in the plurality of optical detectors is in optical communication with a corresponding operating mode of the beam steering element. The hyperspectral/multispectral imaging device further comprises a plurality of detector filters within the housing. Each respective detector filter in the plurality of detector filters covers a corresponding optical detector in the plurality of optical detectors thereby filtering light received by the corresponding optical detector from the beam steering element. At least one processor is within the interior of the housing. The at least one processor is in electrical communication with the one or more light source, the beam steering element, and the plurality of optical detectors. There is a memory within the interior of the housing. At least one program is stored in the memory and is executable by the at least one processor. The at least one program comprises instructions for operating the at least one light source, switching the beam steering element between operating modes in the plurality of operating modes, and controlling each optical detector in the plurality of optical detectors. Further, in some embodiments, there is a communication interface in electrical communication with the at least one processor.

In some embodiments of the devices described above, the light source comprises a first incoherent light source. In some embodiments of the devices described above, the first incoherent light source is configured to emit near-infrared radiation. In some embodiments of the devices described above, the first incoherent light source is a light-emitting diode. In some embodiments of the devices described above, the first incoherent light source is a broadband light source, where the broadband light source emits radiation of wavelengths spanning at least 200 nm. In some embodiments of the devices described above, the broadband light source emits radiation of wavelengths spanning at least 500 nm. In some embodiments of the devices described above, the broadband light source is a white light-emitting diode.

In some embodiments of the devices described above, the device further comprises a first illumination lens covering the first incoherent light source thereby focusing the light emitted by the incoherent light source. In some embodiments of the devices described above, the device further comprises a first light source filter covering the first incoherent light source thereby filtering light emitted by the incoherent light source. In some embodiments of the devices described above, the device further comprises a first light source polarizer covering the first incoherent light source thereby polarizing light emitted by the first incoherent light source. In some embodiments of the devices described above, the device further comprises a first homogenizer covering the first incoherent light source thereby homogenizing light emitted by the first incoherent light source.

In some embodiments of the devices described above, the first incoherent light source is in a first plurality of incoherent light sources disposed on the exterior of the housing. In some embodiments of the devices described above, the first incoherent light source is configured to emit radiation of a first wavelength and a second incoherent light source in the plurality of incoherent light sources is configure to emit radiation of a second wavelength, where the first and second wavelengths are different. In some embodiments of the devices described above, the plurality of incoherent light sources comprises a first sub-plurality of incoherent light sources capable of emitting radiation of a first wavelength. In some embodiments of the devices described above, the first sub-plurality of incoherent light sources is arranged in a first pattern on the exterior of the housing, for instance the first pattern having radial symmetry with respect to the at least one objective lens. In some embodiments of the devices described above, the plurality of incoherent light sources further comprises a second sub-plurality of incoherent light sources capable of emitting radiation of a second wavelength. In some embodiments of the devices described above, the second sub-plurality of incoherent light sources is arranged in a second pattern on the exterior of the housing, for instance the second pattern having radial symmetry with respect to the at least one objective lens. In some embodiments of the devices described above, the plurality of incoherent light sources comprises a plurality of light-emitting diodes. In some embodiments of the devices described above, the plurality of incoherent light sources comprises a plurality of broadband light sources.

In some embodiments of the devices described above, the device further comprises a first plurality of illumination lenses disposed on the exterior of the housing, each illumination lens in the first plurality of illumination lenses covering a corresponding incoherent light source in the plurality of incoherent light sources thereby focusing light emitted by the corresponding incoherent light source. In some embodiments of the devices described above, the plurality of illumination lenses is removable from the exterior of the housing.

In some embodiments of the devices described above, the device further comprises a first plurality of light source filters disposed on the exterior of the housing, each respective light source filter in the first plurality of light source filters covering a corresponding incoherent light source in the plurality of incoherent light sources thereby filtering light emitted by the corresponding incoherent light source.

In some embodiments of the devices described above, the plurality of light source filters is removable from the exterior of the housing.

In some embodiments of the devices described above, the device further comprises a first plurality of light source polarizers, each respective light source polarizer in the first plurality of light source polarizers covering a corresponding incoherent light source in the plurality of incoherent light sources thereby polarizing light emitted by the corresponding incoherent light source. In some embodiments of the devices described above, the plurality of light source polarizers is removable from the exterior of the housing.

In some embodiments of the devices described above, the device further comprises a first plurality of light homogenizers, each respective light homogenizer in the first plurality of light homogenizers covering a corresponding incoherent light source in the plurality of incoherent light sources thereby homogenizing light emitted by the corresponding incoherent light source. In some embodiments of the devices described above, the plurality of light homogenizers is removable from the exterior of the housing.

In some embodiments of the devices described above, the at least one light source comprises a first coherent light source. In some embodiments of the devices described above, the first coherent light source is configured to emit near-infrared radiation. In some embodiments of the devices described above, the first coherent light source is a laser (e.g., a laser diode). In some embodiments of the devices described above, the first coherent light source is in a plurality of coherent light sources disposed on the exterior of the housing. In some embodiments of the devices described above, the plurality of incoherent light sources comprises a plurality of laser diodes.

In some embodiments of the devices described above, the at least one objective lens comprises a fixed focus lens or a variable focus lens. In some embodiments of the devices described above, the at least one objective lens is a variable focus lens that is focused manually. In some embodiments of the devices described above, the objective lens is a variable focus lens that is an autofocus lens. In some embodiments of the devices described above, the variable focus lens is a zoom lens (e.g., a manual zoom lens or an auto-zoom lens).

In some embodiments of the devices described above, the beam steering element comprises a mirror mounted on an actuator. In such embodiments the actuator has a plurality of operating modes.

In some embodiments of the devices described above, the mirror is a single-surface mirror. In some embodiments of the devices described above, the mirror is mounted on an actuator, the actuator having a plurality of operating modes.

In some embodiments of the devices described above, the mirror is a two-axis micro electrical (MEMS) mirror.

In some embodiments of the devices described above, the beam steering element comprises an array of micromirrors. In some embodiments, the array of micromirrors comprises a first and second plurality of micromirrors. Each respective micromirror in the first plurality of micromirrors is in a first orientation with respect to the optical communication path. Each respective micromirror in the second plurality of micromirrors is in a second orientation with respect to the optical communication path. The first and second orientations comprise different operating modes. In some embodiments of the devices described above, the array of micromirrors comprises a digital micromirror device. In some embodiments of the devices described above, the array of micromirrors is mounted on an actuator that has a plurality of operating modes. In some embodiments of the devices described above, the array of micromirrors is mounted on a two-axis micro electro-mechanical (MEMS) device.

In some embodiments of the devices described above, the beam steering element comprises a two-axis scanning device. In some embodiments of the devices described above, the two-axis scanning device is mounted on an actuator. In such embodiments the actuator has a plurality of operating modes. In some embodiments of the devices described above, the two-axis scanning device is mounted on a two-axis micro electro-mechanical (MEMS) device.

In some embodiments of the devices described above, the plurality of optical detectors comprises at least four optical detectors. In some embodiments of the devices described above, each respective optical detector in the plurality of optical detectors is arranged in the interior of the housing and is positioned to receive reflected light from the beam steering element. In some embodiments of the devices described above, each respective optical detector in the plurality of optical detectors is selected from the group consisting of a charge-coupled device (CCD), a complementary metal-oxide-semiconductor (CMOS), a photo-cell, and a focal plane array. In some embodiments of the devices described above, the plurality of optical detectors comprises a plurality of charge-coupled devices (CCDs). In some embodiments of the devices described above, the plurality of optical detectors comprises a plurality of complementary metal-oxide-semiconductors (CMOSs). In some embodiments of the devices described above, the plurality of optical detectors comprises a plurality of photo-cells. In some embodiments of the devices described above, the plurality of optical detectors comprises a plurality of focal plane arrays. In some embodiments of the devices described above, each respective optical detector in the plurality of optical detectors is used for detecting a different frequency of radiation.

In some embodiments of the devices described above, at least one optical detector in the plurality of optical detectors is not covered by a detector filter in the plurality of detector filters. In some embodiments of the devices described above, the at least one optical detector that is not covered by a detector filter is configured for capturing a color image of the surface of the patient. In some embodiments of the devices described above, the at least one optical detector that is not covered by a detector filter is configured for focusing an image of the surface of the patient acquired by at least one respective optical detector in the plurality of optical detectors. In some embodiments of the devices described above, at least one optical detector is covered by a detector filter in the plurality of detector filters and is configured for focusing an image of the surface of the patient acquired by at least one respective optical detector in the plurality of optical detectors.

In some embodiments of the devices described above, the plurality of detector filters comprises at least one bandpass filter, at least one longpass filter, and/or at least one shortpass filter. In some embodiments of the devices described above, the plurality of detector filters is removable from the interior of the housing. In some embodiments of the devices described above, the at least one light source is a plurality of light sources disposed on the exterior of the housing, each respective light source in the plurality of light sources corresponding to an optical detector in the plurality of optical detectors, and each respective detector filter in the plurality of detector filters allows radiation emitted from a corresponding light source in the plurality of light sources to pass through to the corresponding optical detector.

In some embodiments of the devices described above, the device further comprises a plurality of detector polarizers in the interior of the housing, each respective polarizer in the plurality of detector polarizers covering a corresponding optical detector in the plurality of optical detectors thereby polarizing light received by the corresponding optical detector. In some embodiments of the devices described above, the plurality of detector polarizers is removable from the interior of the housing.

In some embodiments of the devices described above, a processor in the at least one processor is selected from the group consisting of a field programmable gate array (FPGA), an application-specific integrated circuit (ASIC), a stream processor, a microprocessor, and a digital signal processor.

In some embodiments of the devices described above, the memory is selected from the group consisting of a random-access memory (RAM), a read-only memory (ROM), and a flash memory.

In some embodiments of the devices described above, the at least one program stored in the memory and executable by the at least one processor comprises instructions for turning on a first light source in the at least one light source, and placing the beam steering element in an operating mode in the plurality of operating modes that causes the beam steering element to be in optical communication with a corresponding optical detector in the plurality of optical detectors. In some embodiments of the devices described above, the at least one program further comprises instructions for sequentially turning on and off each respective light source in the plurality of light sources. In some embodiments of the devices described above, the at least one program further comprises instructions for sequentially switching the beam steering element to each respective operating mode in the plurality of operating modes such that each respective optical detector in the plurality of optical detectors is in optical communication with the beam steering element when said corresponding light source is turned on.

In some embodiments of the devices described above, each respective light source in the plurality of light sources is turned on for less than one second. In some embodiments of the devices described above, each respective light source in the plurality of light sources is turned on for less than one-half of a second. In some embodiments of the devices described above, each respective light source in the plurality of light sources is turned on for less than one-quarter of a second.

In some embodiments of the devices described above, the at least one light source is a plurality of light sources, and the beam steering element comprises a digital micromirror device having a plurality of micromirrors. Each respective micromirror in the plurality of micromirrors has at least a first operating mode in optical communication with a first corresponding optical detector in the plurality of optical detectors and a second operating mode in optical communication with a second corresponding optical detector in the plurality of optical detectors. The at least one program further comprises instructions for turning on a first and a second respective light source in the plurality of light sources and toggling each respective micromirror in the plurality of micromirrors between the first and second operating modes when the first and second respective light sources are turned on. In some embodiments of the devices described above, each respective micromirror in the plurality of micromirrors further has at least a third operating mode in which the respective micromirrors are in optical communication with a third corresponding optical detector in the plurality of optical detectors, and a fourth operating mode in which the respective micromirrors are in optical communication with a fourth corresponding optical detector in the plurality of optical detectors. The at least one program further comprises instructions for turning off the first and second respective light sources, turning on a third and a fourth respective light source in the plurality of light sources, and toggling each respective micromirror in the plurality of micromirrors between the third and fourth operating modes when the third and fourth respective light sources are turned on.

In some embodiments of the devices described above, the at least one light source in the plurality of light sources comprises a plurality of light sources and the beam steering element comprises a digital micromirror device comprising a plurality of micromirrors. In such embodiments, each respective micromirror in the plurality of micromirrors comprises a first operating mode in which the respective micromirror is in optical communication with a first optical detector in the plurality of optical detectors, and a second operating mode in which the respective micromirror is in optical communication with a second optical detector in the plurality of optical detectors. The at least one program further comprises instructions for turning on a first and a second respective light source in the plurality of light sources, placing a first sub-plurality of micromirrors in the plurality of micromirrors to the first operating mode when the first and second respective light sources are turned on, and placing a second sub-plurality of micromirrors in the plurality of micromirrors to the second operating mode when the first and second respective light sources are turned on. In some embodiments of the devices described above, each respective micromirror in the plurality of micromirrors further comprises a third operating mode in which the respective micromirror is in optical communication with a third corresponding optical detector in the plurality of optical detectors, and a fourth operating mode in which the respective micromirror is in optical communication with a fourth corresponding optical detector in the plurality of optical detectors. The at least one program further comprises instructions for turning off the first and second light sources, turning on a third and a fourth respective light source in the plurality of light sources, placing a third sub-plurality of micromirrors in the plurality of micromirrors to the third operating mode when the third and fourth respective light sources are turned on, and placing a fourth sub-plurality of micromirrors in the plurality of micromirrors to the fourth operating mode when the third and fourth respective light sources are turned on.

In some embodiments of the devices described above, the at least one program further comprises instructions for processing a digital image acquired by the plurality of optical detectors. In some embodiments of the devices described above, the instructions for processing a digital image acquired by the plurality of optical detectors comprises instructions for performing at least one of adjusting the brightness of the acquired digital image, adjusting the contrast of the acquired digital image, removing an artifact from the acquired digital image, cropping the acquired digital image, processing one or more sub-pixels of the acquired digital image, compressing the size of the acquired digital image, assembling a plurality of acquired digital images into a spectral hypercube, transforming a spectral hypercube assembled from the plurality of acquired digital images, formatting data contained within the acquired digital image; and encrypting data contained within the acquired digital image.

In some embodiments of the devices described above, the communication interface comprises a wireless signal transmission element. In some embodiments of the devices described above, the wireless signal transmission element is selected from the group consisting of a bluetooth transmission element, a ZigBee transmission element, a Wi-Fi transmission element, a cellular transmission element, or an IEEE 802.11b, 802.11a, 802.11g, or 802.11n communication element. In some embodiments of the devices described above, the communication interface comprises a communication bus. In some embodiments of the devices described above, the communication bus is a universal serial bus (USB), a FireWire serial bus, a serial advanced technology attachment (Serial ATA) bus, a secure digital bus (SD), or an Ethernet bus. In some embodiments of the devices described above, the communication bus is configured to interface with a removable storage media.

In some embodiments of the devices described above, the communication interface comprises a docking station for a mobile device having a mobile device display. In some embodiments of the devices described above, the mobile device is a smart phone, a personal digital assistant (PDA), an enterprise digital assistant, a tablet computer, a digital camera, or a portable music player.

In some embodiments of the devices described above, the device further comprises a housing display disposed on the exterior of the housing. In such embodiments, the housing display is in electronic communication with the at least one processor. In such embodiments, the at least one program further comprises instructions for displaying an image captured by a respective optical detector in the plurality of optical detectors on the housing display. In some embodiments of the devices described above, the housing display is a touch screen display. In some embodiments of the devices described above, the housing display is used for focusing an image of the surface of the patient acquired by at least one respective optical detector in the plurality of optical detectors.

In some embodiments of the devices described above, the imaging device has a maximum power consumption of less than 15 watts, less than 10 watts, or less than 5 watts. In some embodiments of the devices described above, the imaging device is battery powered.

Another aspect of the instant disclosure provides a method of acquiring a set of co-axial images for hyperspectral/multispectral analysis. In one embodiment, the method comprises resolving a plurality of images of an object or subject using a hyperspectral/multispectral imaging device comprising a housing having an exterior and an interior and at least one objective lens attached to or within the housing. The at least one objective lens is disposed in an optical communication path comprising an originating end located at the object or subject and a terminating end. The hyperspectral/multispectral imaging device further comprises a beam steering element within the interior of the housing. The beam steering element is in optical communication with the at least one objective lens and is positioned at the terminating end of the optical communication path. The beam steering element is characterized by a plurality of operating modes. Each respective operating mode in the plurality of operating modes causes the beam steering element to be in optical communication with a different optical detector. The hyperspectral/multispectral imaging device further comprises a plurality of optical detectors offset from the optical communication path. Each respective optical detector in the plurality of optical detectors is in optical communication with a corresponding operating mode of the beam steering element. There is a plurality of detector filters within the housing. Each respective detector filter in the plurality of detector filters covers a corresponding optical detector in the plurality of optical detectors thereby filtering light received by the corresponding optical detector from the beam steering element. At least one processor is in electrical communication with the beam steering element and the plurality of optical detectors. A non-transitory memory is in electrical communication with the at least one processor. There is at least one program stored in the memory that is executable by the at least one processor. The at least one program comprises instructions for switching the beam steering element between operating modes in the plurality of operating modes and controlling each optical detector in the plurality of optical detectors. In some embodiments, there is a communication interface in electrical communication with the at least one processor. Each respective image in the plurality of images is resolved at a different wavelength of light by a respective optical detector in the plurality of optical detectors. Each respective optical detector brought into optical communication with the objective lens by cycling the beam steering element through a plurality of operating modes.

In another aspect, the present disclosure provides a method of hyperspectral/multispectral medical imaging for providing information on a medical condition of a subject. One embodiment provides a method for providing information on a medical condition of a subject using a hyperspectral/multispectral imaging device with a plurality of light sources as described herein. The method comprising illuminating a tissue of the subject with a plurality of lights. Each respective light in the plurality of lights characterized by a different wavelength. Each respective light in the plurality of lights emitted from a corresponding light source in the plurality of light sources and is backscattered from the tissue, thereby forming a plurality of backscattered lights. Each respective backscattered light in the plurality of backscattered lights is resolved by a corresponding optical detector in the plurality of optical detectors, thereby forming a plurality of digital images of the tissue of the subject. Each respective digital image in the plurality of digital images corresponding to a different wavelength of backscattered light. The method further comprises identifying a spectral signature within the plurality of digital images that corresponds with a medical condition, thereby providing information on the medical condition of the subject.

In some embodiments of the devices and methods described above, the step of providing information on a medical condition comprises diagnosing a medical condition.

In some embodiments of the devices and methods described above, the plurality of lights illuminates the tissue in a sequential fashion. In some embodiments, this sequential fashion characterized in that only one light in the plurality of lights is illuminating the tissue of the subject at a time.

In some embodiments of the devices and methods described above, the step of illuminating a tissue of a subject comprises illuminating the tissue with a first respective light and a second respective light in the plurality of lights off the surface of the subject concurrently or nearly concurrently. The first respective light is characterized by a first wavelength and the second respective light is characterized by a second wavelength. This results in the formation of a first backscattered light characterized by the first wavelength and a second backscattered light characterized by the second wavelength.

In some embodiments of the devices and methods described above, the step of resolving the plurality of backscattered lights comprises resolving the first backscattered light by a first respective optical detector in the plurality of optical detectors. The first respective optical detector is covered by a first respective detector filter in the plurality of detector filters. The first detector filter is configured to allow light characterized by the first wavelength to pass through, and not allow light characterized by the second wavelength to pass through. The step of resolving the plurality of backscattered lights further comprises resolving the second backscattered light by a second respective optical detector in the plurality of optical detectors. The second optical detector is covered by a second respective detector filter in the plurality of detector filters. The second optical detector filter is configured to: allow light characterized by the second wavelength to pass through, and to not allow light characterized by the first wavelength to pass through.

In some embodiments of the devices and methods described above, the first and second detector filters are characterized by corresponding first and second central wavelengths, and wherein the first and second central wavelengths are separated by at least 10 nm or by at least 25 nm.

In some embodiments of the devices and methods described above, the first and second detector filters are bandpass filters. In some embodiments of the devices and methods described above, the first detector filter is a shortpass filter and the second detector filter is a longpass filter. In some embodiments of the devices and methods described above, the first and second wavelengths are separated by at least 50 nm or by at least 100 nm.

In some embodiments of the devices and methods described above, the plurality of lights comprises at least three respective lights, each respective light characterized by a different wavelength. In some embodiments of the devices and methods described above, at least one respective light in the plurality of lights is characterized by a near infrared wavelength. In some embodiments of the devices and methods described above, at least one respective light in the plurality of lights is characterized by a visible wavelength. In some embodiments of the devices and methods described above, the plurality of lights includes at least one light characterized by a near infrared wavelength and at least one light characterized by a visible wavelength.

In some embodiments of the devices and methods described above, the step of illuminating the tissue comprises illuminating the tissue of the subject with each respective light in the plurality of lights for no longer than two seconds, or for no longer than one second, or for no longer than a half second, or for no longer than a quarter second.

In some embodiments of the devices and methods described above, the step of identifying a spectral signature within the plurality of digital images that corresponds with a medical condition comprises processing the plurality of digital images of the tissue of the subject to determine a set of values corresponding to the tissue of the subject. In some embodiments of the devices and methods described above, the set of values is selected from deoxyhemoglobin levels, oxyhemoglobin levels, total hemoglobin levels, oxygen saturation, oxygen perfusion, hydration levels, total hematocrit levels, melanin levels, and collagen levels.

In some embodiments of the devices and methods described above, the step of identifying a spectral signature within the plurality of digital images that corresponds with a medical condition comprises processing the plurality of digital images of the surface of the subject to identify a pattern of oxidation or hydration in a tissue associated with the surface of the subject. In some embodiments of the devices and methods described above, processing the plurality of digital images comprises performing at least one of adjusting the brightness of at least one of the respective digital images, adjusting the contrast of at least one of the respective digital images, removing an artifact from at least one of the respective digital images, cropping at least one of the respective digital images, processing one or more subpixels of at least one of the respective digital images, compressing the size of at least one of the respective digital images, assembling the plurality of digital images into a spectral hypercube, transforming a spectral hypercube assembled from the plurality of digital images, formatting data contained within at least one of the respective digital images, and encrypting data contained within at least one of the respective digital images.

In some embodiments of the devices and methods described above, at least a first processing step is performed by the at least one processor of the hyperspectral/multispectral imaging device. In some embodiments of the devices and methods described above, at least a second processing step is performed external to the hyperspectral/multispectral imaging device. In some embodiments of the devices and methods described above, the at least second processing step is performed by a mobile device, where the mobile device is configured to be in electrical communication with the hyperspectral/multispectral imaging device. In some embodiments of the devices and methods described above, the mobile device is selected from the group consisting of a smart phone, a personal digital assistant (PDA), an enterprise digital assistant, a tablet computer, a digital camera, and a portable music player. In some embodiments of the devices and methods described above, the at least second processing step is performed by an external server. In some embodiments of the devices and methods described above, the external server is a cloud computing environment. In other embodiments of the devices and methods described above, the external server is a server hosted within a hospital where the imaging takes place.

In some embodiments of the devices and methods described above, the medical condition is selected from the group consisting of tissue ischemia, ulcer formation, ulcer progression, venous stasis, venous ulcer disease, infection, shock, cardiac decompensation, respiratory insufficiency, hypovolemia, the progression of diabetes, congestive heart failure, sepsis, dehydration, hemorrhage, hypertension, exposure to a chemical or biological agent, and an inflammatory response.

In some embodiments of the methods described above, the method further comprises focusing a preliminary image of the tissue of the subject prior to resolving the plurality of backscattered lights.

In some embodiments of the devices and methods described above, the hyperspectral/multispectral imaging device further comprises a housing display disposed on the exterior of the housing, the housing display is in electronic communication with the at least one processor, where the preliminary image is displayed on the housing display. In some embodiments of the devices and methods described above, the communication interface of the hyperspectral/multispectral imaging device is in electronic communication with a mobile device having a mobile device display, where the preliminary image is displayed on the mobile device display. In some embodiments of the devices described above, the mobile device is selected from the group consisting of a smart phone, a personal digital assistant (PDA), an enterprise digital assistant, a tablet computer, a digital camera, and a portable music player.

In one aspect, the present disclosure provides a method for acquiring a hyperspectral/multispectral imaging comprising a plurality of images. In one embodiment, the method includes resolving the plurality of images of a subject using a hyperspectral/multispectral imaging device comprising: a housing having an exterior and an interior; at least one objective lens attached to or within the housing, the at least one objective lens disposed in an optical communication path, the optical communication path comprising an originating end located at the object or subject and a terminating end; a beam steering element within the interior of the housing, the beam steering element in optical communication with the at least one objective lens and positioned at the terminating end of the optical communication path, the beam steering element characterized by a plurality of operating modes, each respective operating mode in the plurality of operating modes causing the beam steering element to be in optical communication with a different optical detector; a plurality of optical detectors offset from the optical communication path, each respective optical detector in the plurality of optical detectors in optical communication with a corresponding operating mode of the beam steering element; a plurality of detector filters within the housing, each respective detector filter in the plurality of detector filters covering a corresponding optical detector in the plurality of optical detectors thereby filtering light received by the corresponding optical detector from the beam steering element; at least one processor in electrical communication with the beam steering element and the plurality of optical detectors; a memory in electrical communication with the at least one processor, wherein at least one program is stored in the memory and executable by the at least one processor, the at least one program comprising instructions for: switching said beam steering element between operating modes in the plurality of operating modes and controlling each optical detector in said plurality of optical detectors; and a communication interface in electrical communication with the at least one processor. In some embodiments of the methods described above, each respective image in the plurality of images is resolved at a different wavelength of light by a respective optical detector in the plurality of optical detectors, each respective optical detector brought into optical communication with the objective lens by cycling the beam steering element through a plurality of operating modes.

In one aspect, the present disclosure provides a non-transitory computer readable storage medium storing at least one program for collecting co-axially aligned images of a subject at a plurality of narrowband wavelengths configured for execution by at least one processor of a computer system. In one embodiment, the at least one program includes instructions for: turning on a first illumination source configured to emit narrowband light having a first wavelength or first wavelength band; placing a beam steering element in a first operating mode in optical communication with a first optical detector configured to resolve narrowband light having the first wavelength or the first wavelength band; capturing an image of the subject illuminated by the light emitted by the first illumination source using the first optical detector; turning off the first illumination source; turning on a second illumination source configure to emit narrowband light having a second wavelength or a second wavelength band; placing the beam steering element in a second operating mode in optical communication with a second detector configured to resolve narrowband light having the second wavelength or the second wavelength band; capturing an image of the subject illuminated by the light emitted by the second illumination source using the second optical detector; and optionally repeating the fourth through seventh steps a first predetermined number of times to collect a second predetermined number of images at distinct wavelengths or wavelength bands, thereby collecting co-axially aligned images of the subject.

In one aspect, the present disclosure provides a method for directing an imager to acquire a hyperspectral/multispectral image of a tissue of a subject, the hyperspectral/multispectral image comprising a plurality of sub-images of the tissue of the subject, each respective sub-image in the plurality of sub-images acquired at a corresponding wavelength or wavelength band in a plurality of wavelengths or wavelength bands. In some embodiments of the devices and methods described above, the imager includes: a housing having an exterior and an interior; at least one light source disposed on the exterior of the housing; at least one objective lens attached to or within the housing, the at least one objective lens disposed in an optical communication path, the optical communication path comprising an originating end and a terminating end, where light from the at least one light source is first backscattered by a tissue of a subject and then passed from the originating end of the optical communication path, through the at least one objective lens, and to the terminating end of the optical communication path; a beam steering element within the interior of the housing, the beam steering element in optical communication with the terminating end of the optical communication path, the beam steering element characterized by a plurality of operating modes; a plurality of optical detectors offset from the optical communication path, each respective optical detector in the plurality of optical detectors in optical communication with a corresponding operating mode of the beam steering element; and a plurality of detector filters within the housing, each respective detector filter in the plurality of detector filters covering a corresponding optical detector in the plurality of optical detectors thereby filtering light received by the corresponding optical detector from the beam steering element so that each optical detector in the plurality of optical detectors is configured for recording a respective sub-image in the plurality of sub-images at the wavelength or wavelength band of the respective sub-image. In some embodiments of the methods described above, the method includes identifying a plurality of baseline exposure times, each respective baseline exposure time in the plurality of baseline exposure times representing an exposure time for resolving a respective sub-image, in the plurality of sub-images, of the tissue of the subject at the wavelength or wavelength band of the respective sub-image, wherein a first baseline exposure time for a first sub-image is different than a second baseline exposure time of a second sub-image in the plurality of sub-images. In some embodiments, the method further includes cycling the beam steering element through the plurality of operating modes, wherein the beam steering element is retained in each respective operating mode for the baseline exposure time corresponding to the wavelength or wavelength band collected by the optical filter corresponding to the respective operating mode so that a sub-image is recorded on the optical detector corresponding to the respective operating mode, thereby collecting the hyperspectral/multispectral image of the tissue.

In one aspect, the present disclosure provides a non-transitory computer readable storage medium storing one or more programs executable by a hyperspectral/multispectral imaging device with a central processing unit configured to execute the one or more programs and an optical acquisition subsystem configured to acquire a hyperspectral/multispectral image of a tissue of a subject, the hyperspectral/multispectral imaging device comprising: a housing having an exterior and an interior; at least one light source disposed on the exterior of the housing; at least one objective lens attached to or within the housing, the at least one objective lens disposed in an optical communication path, the optical communication path comprising an originating end and a terminating end, wherein light from the at least one light source is first backscattered by a tissue of a subject and then passed from the originating end of the optical communication path, through the at least one objective lens, and to the terminating end of the optical communication path; a beam steering element within the interior of the housing, the beam steering element in optical communication with the terminating end of the optical communication path, the beam steering element characterized by a plurality of operating modes; a plurality of optical detectors offset from the optical communication path, each respective optical detector in the plurality of optical detectors in optical communication with a corresponding operating mode of the beam steering element; and a plurality of detector filters within the housing, each respective detector filter in the plurality of detector filters covering a corresponding optical detector in the plurality of optical detectors thereby filtering light received by the corresponding optical detector from the beam steering element so that each optical detector in the plurality of optical detectors is configured for recording a respective sub-image in the plurality of sub-images at the wavelength or wavelength band of the respective sub-image. In some embodiments, the one or more programs comprising instructions for identifying a plurality of baseline exposure times, each respective baseline exposure time in the plurality of baseline exposure times representing an exposure time for resolving a respective sub-image, in the plurality of sub-images, of the tissue of the subject at the wavelength or wavelength band of the respective sub-image, wherein a first baseline exposure time for a first sub-image is different than a second baseline exposure time of a second sub-image in the plurality of sub-images and cycling the beam steering element through the plurality of operating modes, wherein the beam steering element is retained in each respective operating mode for the baseline exposure time corresponding to the wavelength or wavelength band collected by the optical filter corresponding to the respective operating mode so that a sub-image is recorded on the optical detector corresponding to the respective operating mode, thereby collecting the hyperspectral/multispectral image of the tissue.

In some embodiments of the methods and non-transitory computer readable storage medium described above, a baseline exposure time for a sub-image in the plurality of sub-images is determined by a factor affecting a baseline illumination of the tissue of the subject and a sensitivity of the corresponding optical detector in the optical acquisition subsystem used to acquire the sub-image at the wavelength or wavelength band corresponding to the sub-image.

In some embodiments of the methods and non-transitory computer readable storage medium described above, the factor is an amount of illumination of the tissue of the subject provided by an illumination subsystem of the hyperspectral/multispectral imaging device, an amount of ambient light, or a concentration of melanin in the tissue of the subject.

BRIEF DESCRIPTION OF THE DRAWINGS

FIG. 8A is a front elevational view of the first housing; FIG. 8B is a back elevational view thereof; FIG. 8C is a top plan view thereof; FIG. 8D is a bottom plan view thereof; FIG. 8E is a left side elevational view thereof; and FIG. 8F is a right side elevational view thereof.

FIG. 9A is a front elevational view of the second housing; FIG. 9B is a back elevational view thereof; FIG. 9C is a top plan view thereof; FIG. 9D is a bottom plan view thereof; FIG. 9E is a left side elevational view thereof; and FIG. 9F is a right side elevational view thereof.

FIG. 10A is a front elevational view of the second housing; FIG. 10B is a back elevational view thereof; FIG. 10C is a top plan view thereof; FIG. 10D is a bottom plan view thereof; FIG. 10E is a left side elevational view thereof; and FIG. 10F is a right side elevational view thereof.

DETAILED DESCRIPTION

I. Introduction

Figure 1:
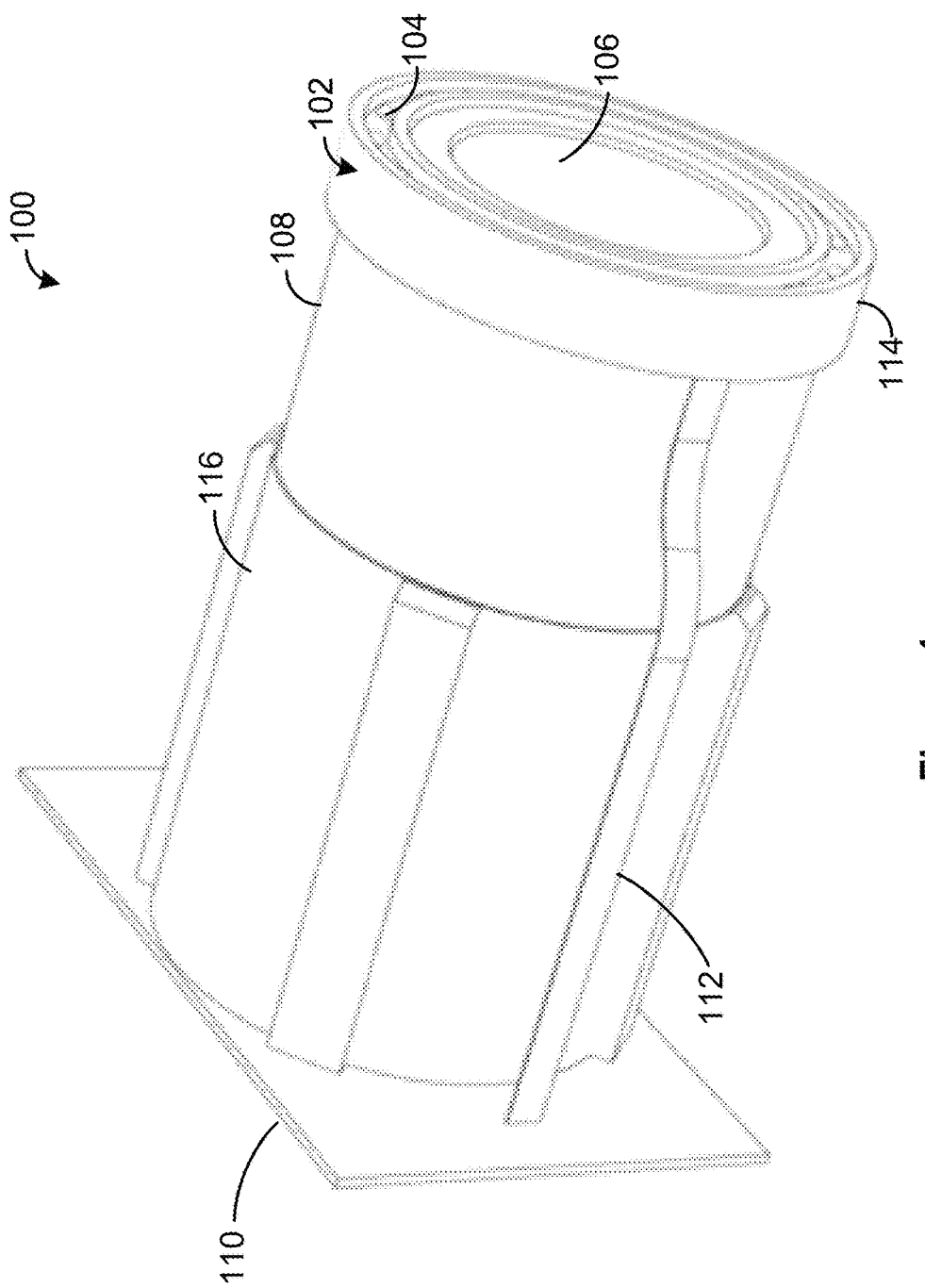
FIG. 1 is a schematic illustration of the internal hardware of a co-axial hyperspectral/multispectral camera, according to some embodiments.

Hyperspectral and multispectral imaging are related techniques in larger class of spectroscopy commonly referred to as spectral imaging or spectral analysis. Typically, hyperspectral imaging relates to the acquisition of a plurality of images, each image representing a narrow spectral band collected over a continuous spectral range, for example, 20 spectral bands having a FWHM bandwidth of 20 nm each, covering from 400 nm to 800 nm. In contrast, multispectral imaging relates to the acquisition of a plurality of images, each image representing a narrow spectral band collected over a discontinuous spectral range. For the purposes of the present disclosure, the terms "hyperspectral" and "multispectral" are used interchangeably and refer to a plurality of images, each image representing a narrow spectral band (having a FWHM bandwidth of between 10 nm and 30 nm, between 5 nm and 15 nm, between 5 nm and 50 nm, less than 100 nm, between 1 and 100 nm, etc.), whether collected over a continuous or discontinuous spectral range.

As used herein, the terms "narrow spectral range" or "narrowband" are used interchangeably and refer to a continuous span of wavelengths, typically consisting of a FWHM spectral band of no more than about 100 nm. In certain embodiments, narrowband radiation consists of a FWHM spectral band of no more than about 75 nm, 50 nm, 40 nm, 30 nm, 25 nm, 20 nm, 15 nm, 10 nm, 5 nm, 4 nm, 3 nm, 2 nm, or 1 nm.

Hyperspectral deals with imaging narrow spectral bands over a continuous spectral range, and produce the spectra of all pixels in the scene. So a sensor with only 20 bands can also be hyperspectral when it covers the range from 500 to 700 nm with 20 bands each 10 nm wide. (While a sensor with 20 discrete bands covering the visible spectrum, near-infrared, short-wavelength infrared, mid-wavelength infrared, and long-wavelength infrared would be considered multispectral.)

Among other aspects, the application provides methods and systems that enable the capture of co-axial hyperspectral/multispectral images using a beam steering element having a plurality of operating modes and a plurality of optical detectors, each of which is configured to resolve light at a specific wavelength(s). The architecture of the internal hardware of the hyperspectral/multispectral systems provided herein (e.g., beam steering element and optical detectors), provides several advantages over systems and methods of hyperspectral/multispectral imaging known in the art. For example, the systems and methods provided herein allow for true co-axial alignment of images captured at a range of wavelengths without the need for a tunable filter, shorter subject illumination times, shorter image exposure times, more rapid hyperspectral/multispectral imaging, lower power consumption, and lower manufacturing costs, to name a few benefits.

Specifically, the present application provides hyperspectral/multispectral systems and methods that use a beam steering element (e.g., a mirror or array of micromirrors) having a plurality of operating modes capable of directing light of different wavelengths to distinct optical detectors from a common point of origin, thus maintaining co-axial alignment between images captured by the respective optical detectors. In some embodiments, each of the optical detectors is covered by a filter, to select a specific wavelength of light. This allows for the resolution of images of an object at multiple wavelengths without the need for expensive optics, such as tunable filers (e.g., liquid crystal tunable filters). As opposed to imaging systems that rely on line scanning to capture images at separate wavelengths (e.g., systems employing a prism or diffraction grating), the systems described herein can capture true two-dimensional co-axial images by sequentially resolving images of the object at different wavelengths using respective optical detectors in a plurality of optical detectors.

In certain embodiments, very minor pixel field alignment between wavelength images may be necessary to account for edge effects and minor mechanical misalignment between the optical detectors and beam steering element. In some embodiments, the hyperspectral/multispectral imaging systems described herein will contain software operable by the central processing unit(s) 1308 to perform minor image alignment between digital images 1332 acquired by different optical detectors 206, for example, during post processing of the hyperspectral/multispectral data cube 1336. In other embodiments, minor alignment may be performed by an external device or server after the digital images 1332 and/or hyperspectral/multispectral data cube 1336 is transmitted from the imaging system.

Furthermore, in certain embodiments, some of the disclosed hyperspectral/multispectral have matching narrow band illumination sources and detector filters. The use of matching illumination and detection elements dramatically increases the signal-to-noise ratio of the resolved images (e.g., the amount of light having a desired wavelength as compared to the amount of light having undesired wavelengths). The signal-to-noise ratio of the resolved images can be further increased by including matching polarizers over corresponding illumination and detection elements.

Increasing the signal-to-noise ratio allows for shorter illumination and exposure times, thereby increasing the optical throughput of the system. Thus, the hyperspectral/multispectral imaging systems provided herein can effectively capture images of a target object, for example, at five different wavelengths in a single second. This is accomplished by sequentially illuminating the object with narrowband light sources of various wavelengths and capturing images of the object with optical detectors configured to resolve light of the respective broadband wavelengths Hyperspectral/multispectral systems that capture images at different wavelengths using detectors that are slightly offset from one another (e.g., at two or more detectors positioned next to each other at the end of an optical path) require extensive computational power to index and align the images with one another. Similarly, images captured using imaging systems that rely on co-boring of multiple objective lenses (e.g., where the center of each objective lens points to a common target), must be mathematically corrected so that information obtained from each objective lens transposes one-to-one. Advantageously, the imaging systems provided herein provide true co-axial aligned images, reducing the computation burden and thus increasing the speed at which hyperspectral/multispectral data can be processed.

Furthermore, the use of matching illumination and detection elements also eliminates wasted light in bands other than those desired for imaging (e.g., out of band light), thereby improving the efficiency of the imaging system. The increased efficiency provided by sequential illumination with narrowband radiation, the absence of tunable filters, and decreased processor requirements results in an imaging system with a low power requirement. Table 1 provides an estimated power budget, for one embodiment of a hyperspectral/multispectral camera, based on a state of the art mechanical/electrical elements. As shown in Table 1, in one embodiment, a hyperspectral/multispectral imaging device (e.g., a camera) can be designed to consume a maximum of from 4 to 8 watts of power, low enough to be battery powered. Accordingly, in one embodiment, the disclosure provides a hyperspectral/multispectral camera that is battery operated. In certain embodiments, the camera has a maximum power requirement of less than 15 watts, less than 10 watts, or less than 5 watts. In yet other embodiments, the camera has a maximum power requirement of less than 20 W, 19 W, 18 W, 17 W, 16 W, 15 W, 14 W, 13 W, 12 W, 11 W, 10 W, 9 W, 8 W, 7 W, 6 W, 5 W, or fewer watts. Of course, it is expected over time that more efficient mechanical/electrical elements will be designed, and such improved elements can be used to provide a more efficient hyperspectral/multispectral imaging devise as described herein.

TABLE 1

Estimated power budget for one embodiment of a hyperspectral/multispectral camera.

| Electrical/Mechanical Element | Power Requirement (Watts) |
| --- | --- |
| Digital processor | 2.0 to 3.5 |
| LED illumination | 1.0 to 2.5 |
| Camera electronics | 0.25 to 0.5 |
| Wireless network interface and associated electronics | 0.25 to 0.5 |
| Beam steering element control | 0.25 |
| Battery control and power conversion electronics | 0.25 to 0.5 |
| Maximum power requirement | 4 to 7.75 |

In one embodiment, the systems and methods provided herein are useful for hyperspectral/multispectral medical imaging and diagnostics. For example, a beam steering element and plurality of optical detectors can be mounted inside a camera housing, for easy manipulation by a healthcare professional.

In another embodiment, the systems and methods provided herein are useful for other hyperspectral/multispectral applications such as satellite imaging (e.g., for geological sensing of minerals, agricultural imaging, and military surveillance), remote chemical imaging, and environmental monitoring. For example, a beam steering element and plurality of optical detectors can be mounted inside a satellite or other telescopic apparatus for remote hyperspectral/multispectral imaging.

II. Systems for Hyperspectral/Multispectral Imaging

FIG. 1 shows a schematic illustration of the internal hardware 100 of a co-axial hyperspectral/multispectral camera, according to some embodiments. The camera includes an illumination subsystem 102 comprising a housing 114 for one or more light source(s) 104, which are controlled by a central processing unit (CPU; not shown). The lights are in electronic communication with a motherboard 110, housing the CPU, by way of a flex circuit or wire 112 that connects the illumination subsystem to the motherboard 110. The camera further includes a lens subsystem, comprising an objective lens 106, and optionally a complex lens assembly (not shown), which is mounted inside a chassis 108 that appropriately positions the complex lens assembly with respect to an optical communication path originating at the surface of a subject, and terminating at a beam steering element (not shown) situated in the interior of the camera assembly. An optional stray light shield 116 functions to decrease stray light and reflections within the internal camera assembly.

Figure 2A:
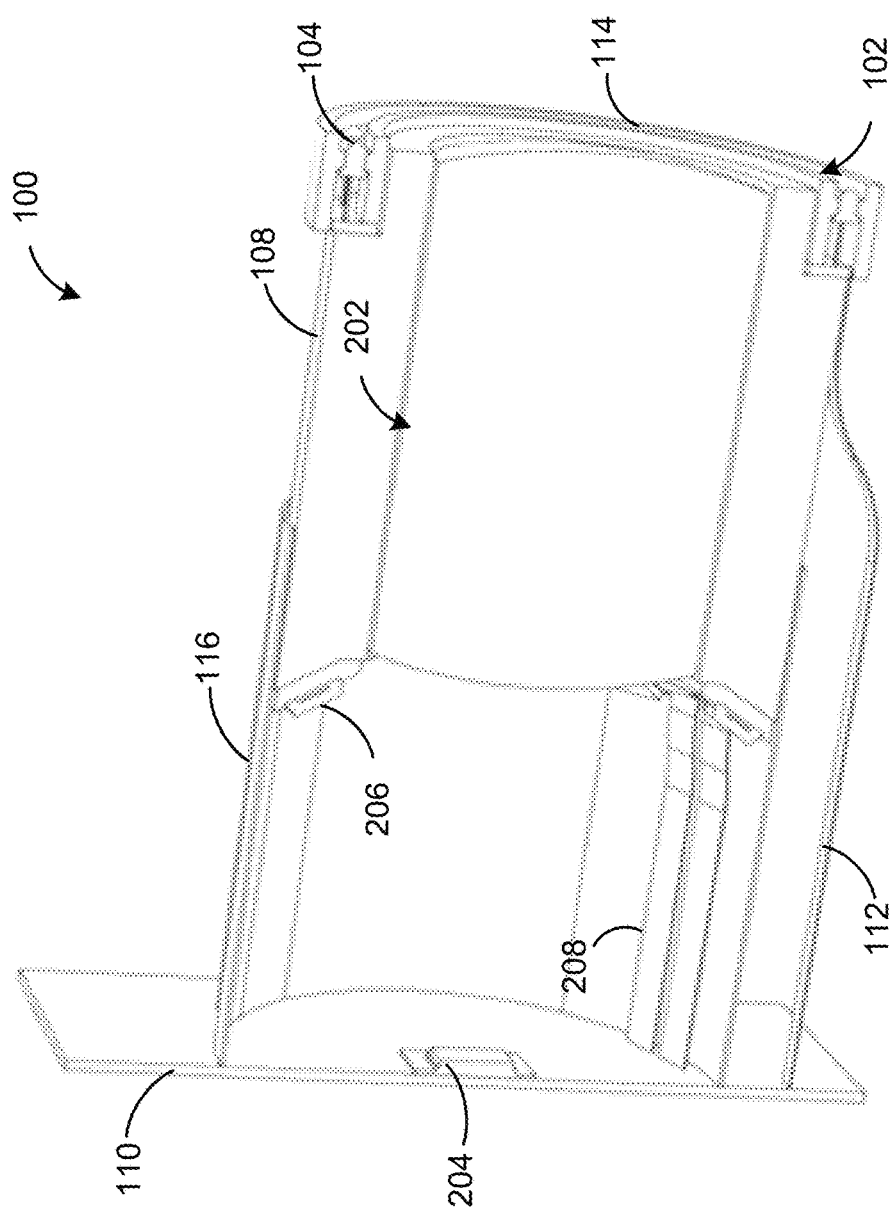
FIG. 2A is a schematic illustration of the internal hardware of a co-axial hyperspectral/multispectral camera, according to some embodiments. The illustration shows a cross-section down the barrel of the camera with a perspective view of the beam steering element 204.
Figure 2B:
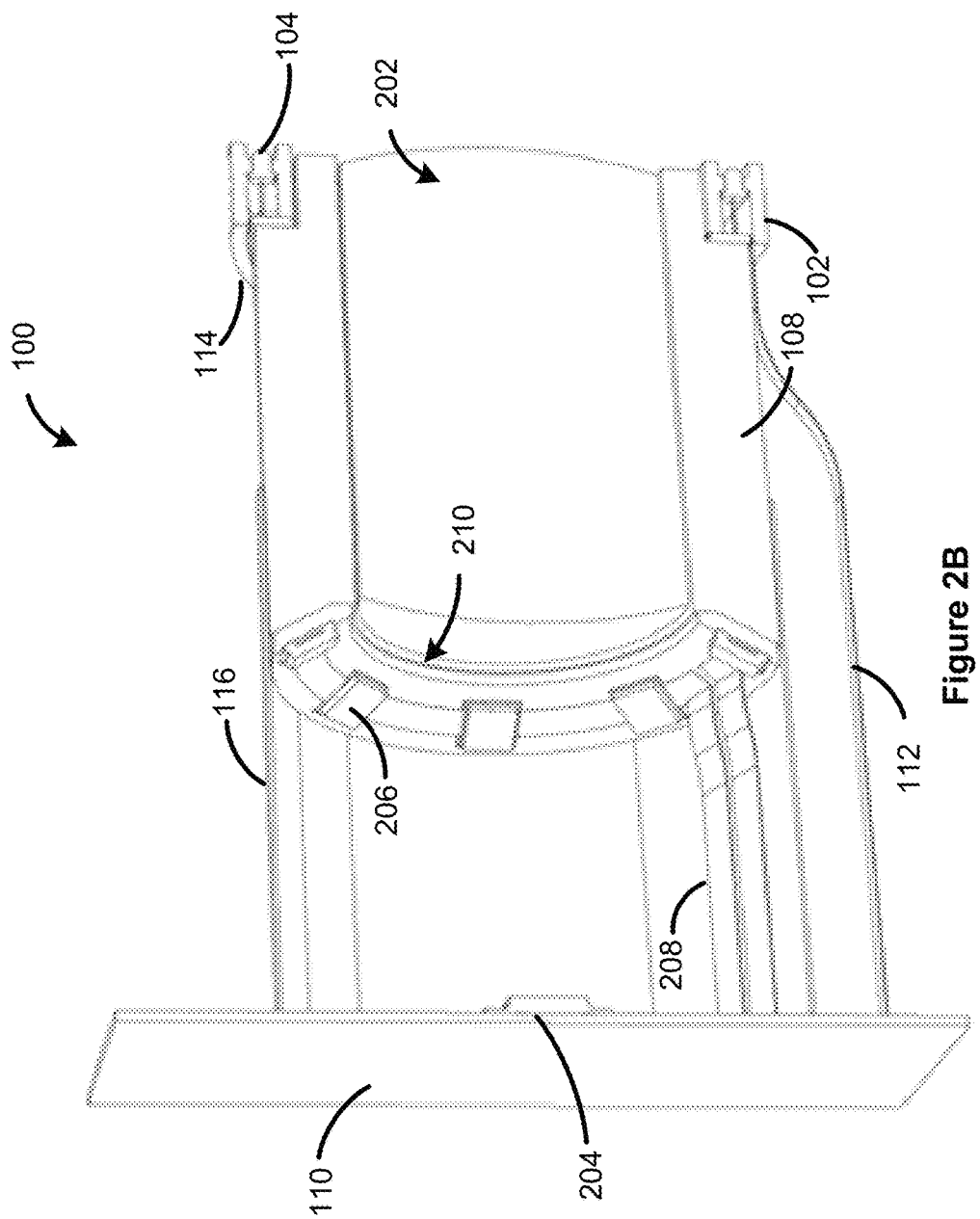
FIG. 2B is a schematic illustration of the internal hardware of a co-axial hyperspectral/multispectral camera, according to some embodiments. The illustration shows a cross-section down the barrel of the camera with a perspective view of the optical detectors 206.

FIGS. 2A and 2B show a cross-section down the barrel of the internal hardware 100 of a co-axial hyperspectral/multispectral camera, according to some embodiments. FIG. 2A provides a perspective view of the beam steering element 204, while FIG. 2B provides a perspective view of the imager subsystem 210. According to certain embodiments, the co-axial hyperspectral/multispectral camera includes: an illumination subsystem 102 containing one or more light sources 104; an objective lens assembly 202 housed in a chassis 108 that anchors the lens assembly with respect to other components of the optical assembly; an optional stray light shield 116; a beam steering element 204 in electrical communication, and optionally mounted on, a motherboard 110 in electrical communication with one or more CPU(s) (not shown); and an imager subsystem 210 comprising a plurality of optical detectors 206 in electrical communication with the motherboard 110 by way of a flex circuit or wire 208.

In one embodiment, an optical communication path is created when radiation emitted from one or more of the lights 104 of the illumination subsystem 102 illuminates a tissue of the subject (not shown) and is backscattered to an objective lens assembly 202, which focuses the light on a beam steering element 204 having a plurality of operating modes. When positioned in a respective operating mode, the beam steering element 204 reflects the light onto one of the plurality of optical detectors 206, which is configured to capture an image of the surface of the subject at one or more specific wavelengths.

Each optical detector 206 in the imager subsystem 210 is optionally covered by an optical filter (e.g., a detector filter), which allows light of a predetermined wavelength to pass through to the detector. In one embodiment, one or more of the light sources 104 is matched to a filter covering an optical detector 206, e.g., the light emits radiation at wavelength that is capable of passing through the corresponding filter. When respective light sources 104 in a plurality of light sources are matched to corresponding detector filters in a plurality of detector filters, the beam steering element 204 functions to direct radiation emitted by a respective light source 104 to the corresponding optical detector 206 covered by a matching filter. The beam steering element 204 is configured to have a plurality of operating modes, each of which directs light backscattered from the tissue of the subject to a different optical detector 206.

Figure 12:
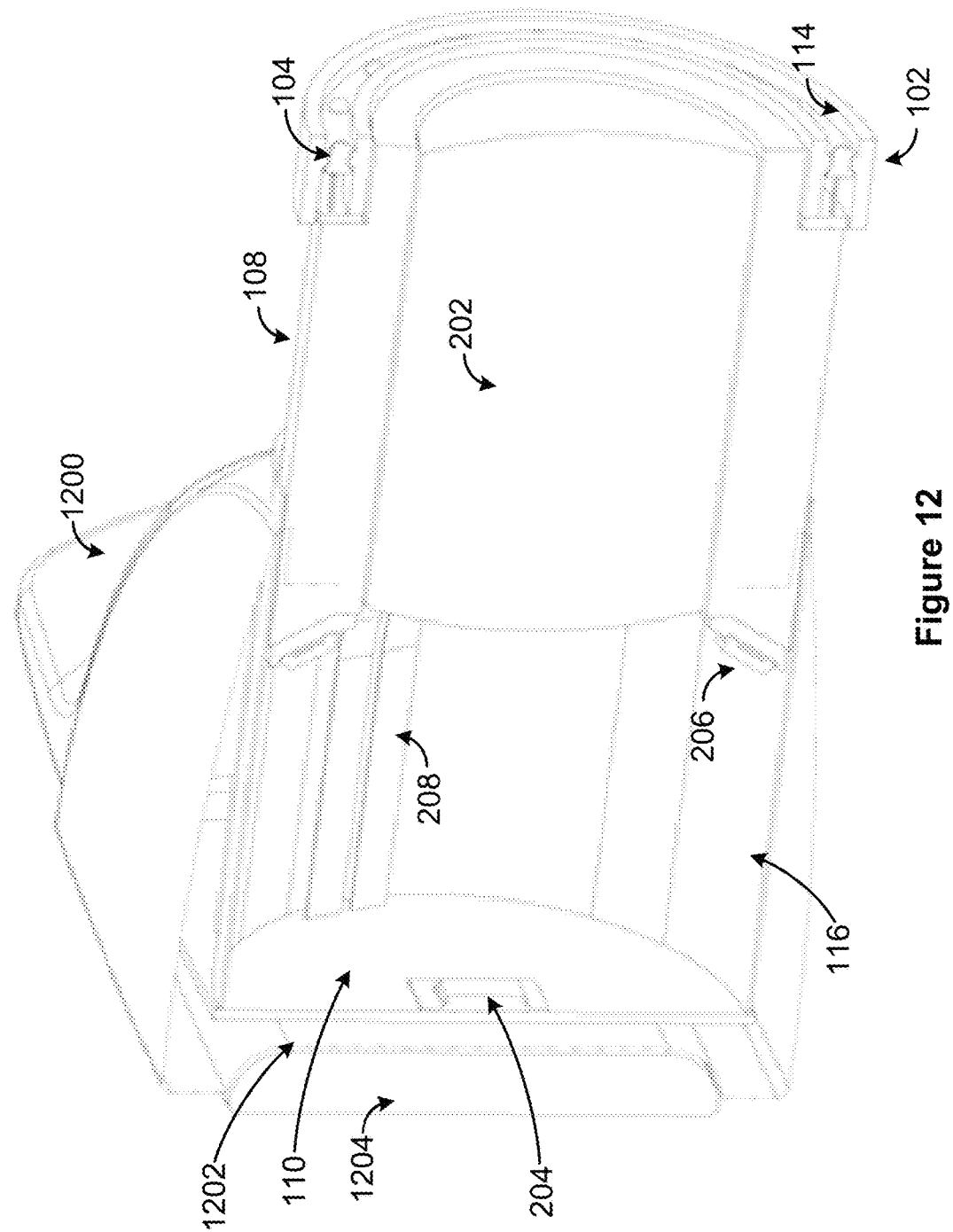
FIG. 12 is a schematic illustration of the internal hardware of a co-axial hyperspectral/multispectral camera mounted in a housing, according to some embodiments. The illustration shows a cross-section down the barrel of the camera with a perspective view of the beam steering element 204.

FIG. 12 shows the same cross-section as FIG. 2A of the internal hardware 100 of a co-axial hyperspectral/multispectral camera mounted in housing 1200, according to some embodiments. Optionally, housing 1200 includes dock 1202 for attaching portable device 1204 to housing 1200. Optionally, portable device 1204 contains a display, preferably a touch-screen display, for displaying images acquired by internal hardware 100 of a co-axial hyperspectral/multispectral camera.

Figure 3A:
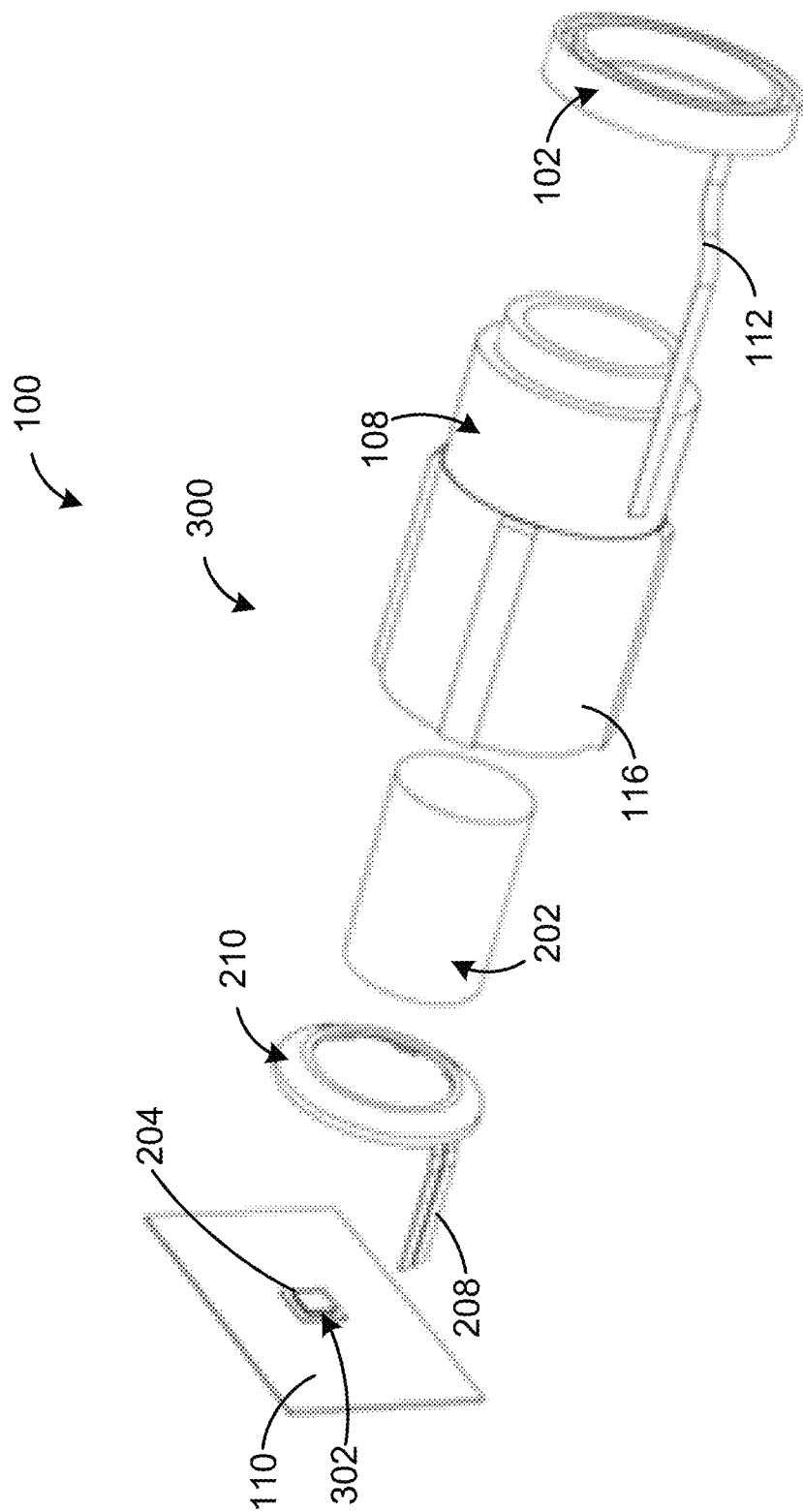
FIG. 3A is a schematic illustration of the internal hardware of a co-axial hyperspectral/multispectral camera, according to some embodiments. The illustration shows an exploded view of the components of the internal hardware with a perspective view of the beam steering element 204.
Figure 3B:
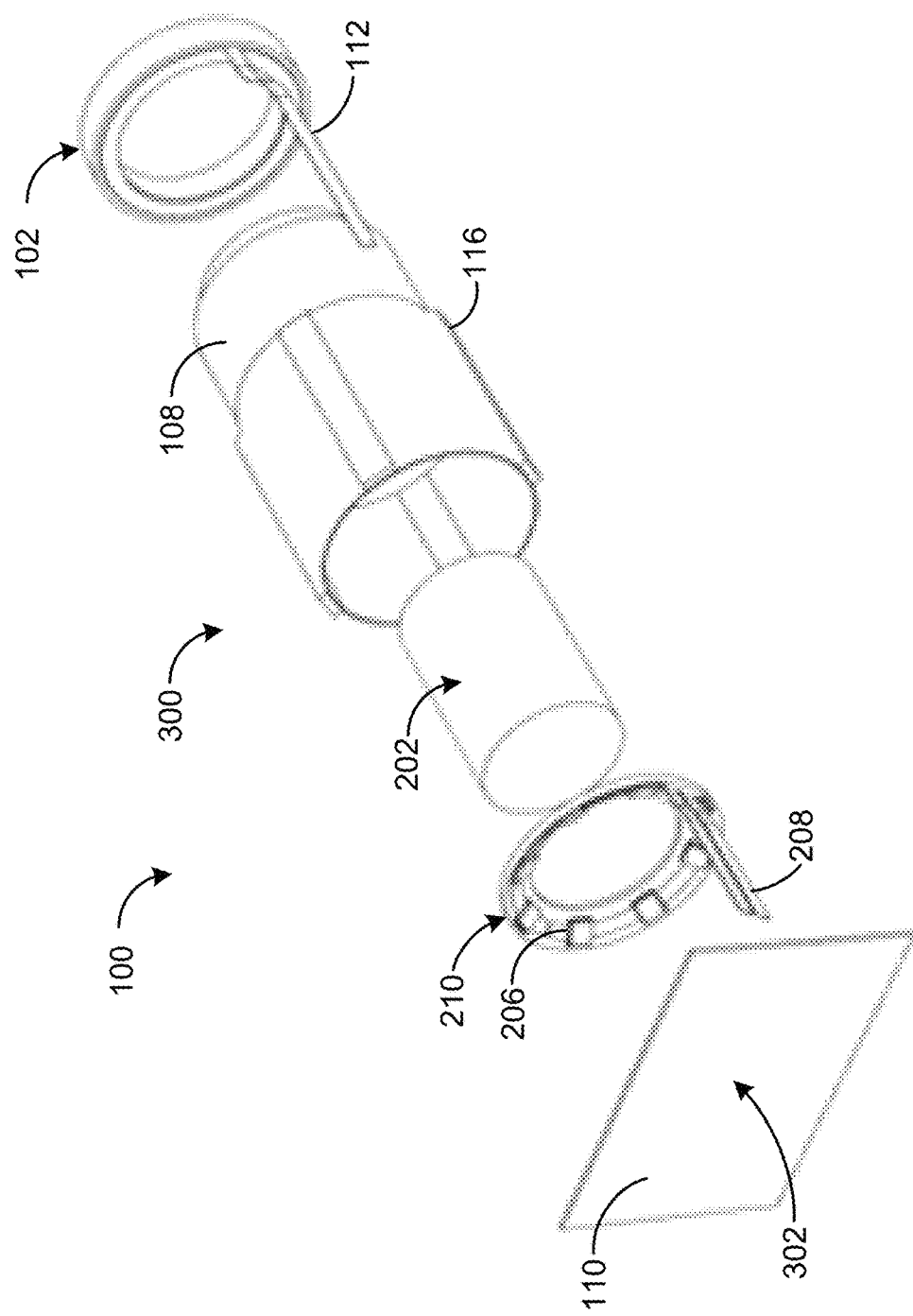
FIG. 3B is a schematic illustration of the internal hardware of a co-axial hyperspectral/multispectral camera, according to some embodiments. The illustration shows a cross-section down the barrel of the camera with a perspective view of the imager subsystem 210.

FIGS. 3A and 3B show exploded views of the internal hardware of a co-axial hyperspectral/multispectral camera, according to some embodiments. FIG. 3A provides a perspective view of the light directing subsystem 302, while FIG. 2B provides a perspective view of the imager subsystem 210. The exploded views show the various components of the illumination subsystem 102, lens subsystem 300, light directing subsystem 302, and imager subsystem 210.

Figure 4:
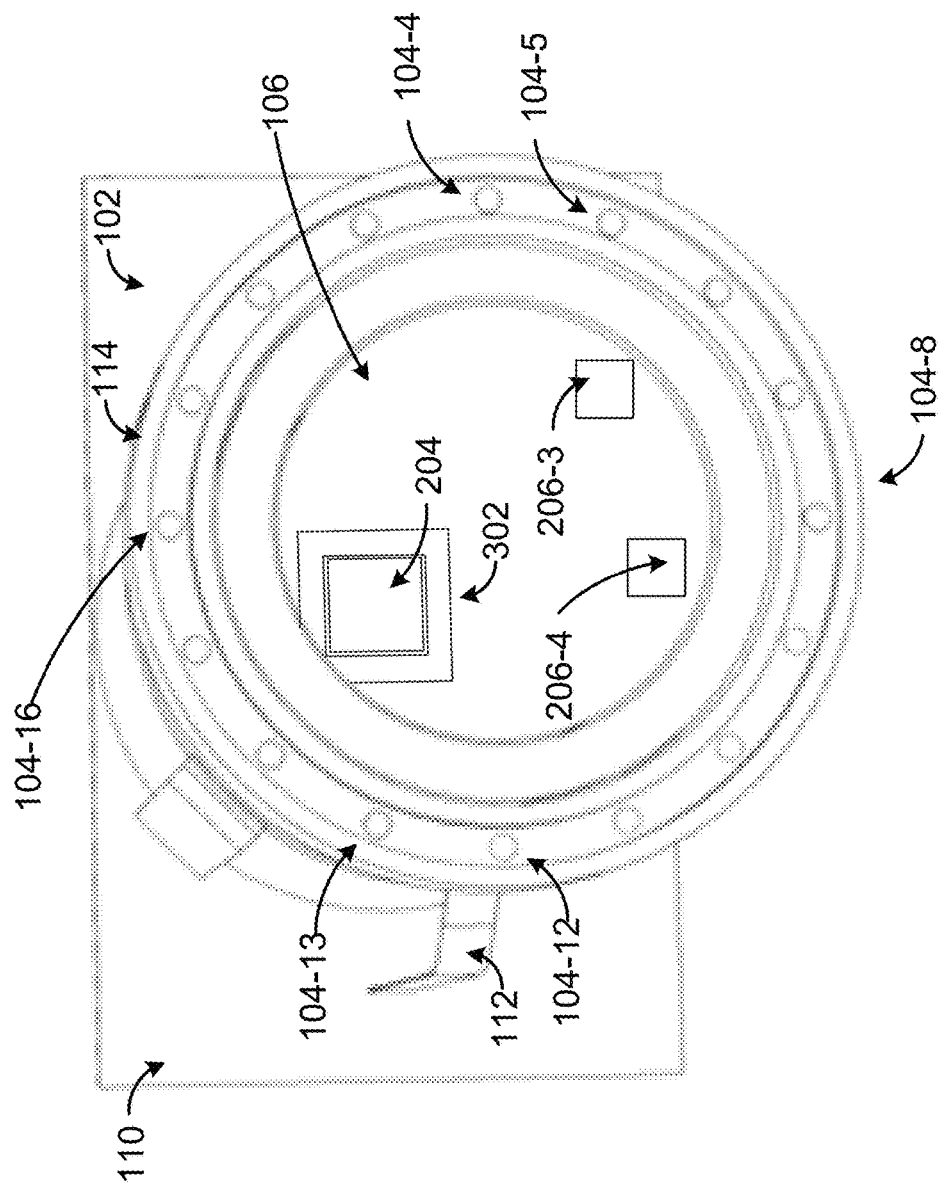
FIG. 4 is a schematic illustration of the internal hardware of a co-axial hyperspectral/multispectral camera, according to some embodiments. The illustration shows a view looking down the barrel of the camera.

FIG. 4 shows a view looking down the barrel of the lens subsystem of a co-axial hyperspectral/multispectral camera, according to some embodiments. The illumination subsystem comprises a plurality of lights 104 in a radial arrangement about the objective lens 106. Optionally, the lights 104 are arranged having radial or approximate radial symmetry with respect to the objective lens 106. The light directing subsystem 302, comprising the beam steering element 204 and optionally an actuator (not shown) for moving the beam steering element between various operating modes, is disposed at the distal end of the barrel of the camera. The beam steering element 204 is capable of switching between operating modes to reflect light to the various optical detectors 206 mounted on the backside of the imager subsystem 210.

Figure 5:
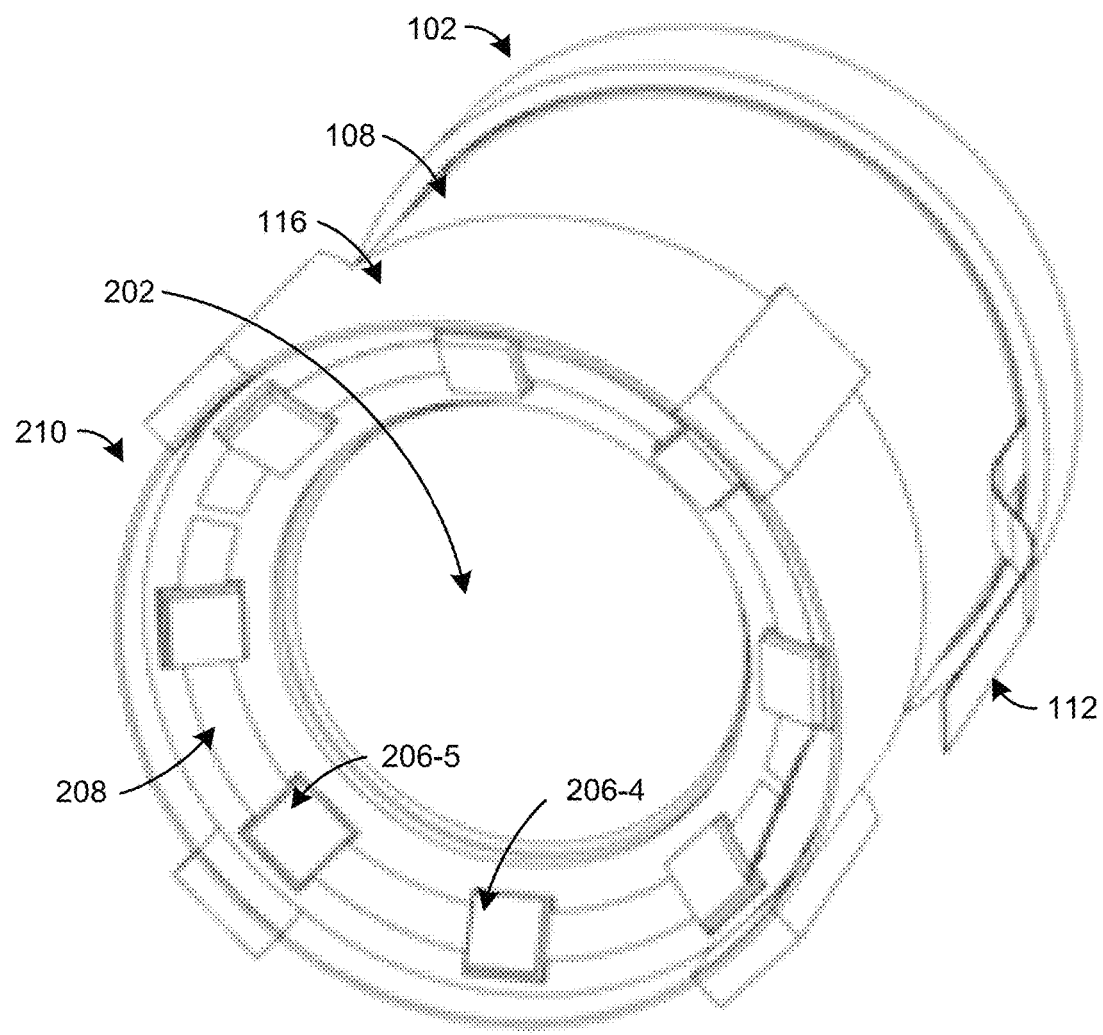
FIG. 5 is a schematic illustration of the internal hardware of a co-axial hyperspectral/multispectral camera, according to some embodiments. The illustration shows a cross-section through the barrel of the camera with a perspective view of the imager subsystem 210.

FIG. 5 illustrates a perspective view looking up the barrel of the lens subsystem of a co-axial hyperspectral/multispectral camera, according to some embodiments. The illustration shows a plurality of optical detectors 206 mounted on the back side of the imager subsystem 210, in a radial arrangement about the objective lens assembly 202. Optionally, the optical detectors 206 are arranged having radial or near radial symmetry with respect to the objective lens assembly 202. The optical detectors 206 are offset from an optical communication path originating at a surface of an object being imaged and terminating at the beam steering element 204, yet in optical communication with corresponding operating modes of the beam steering element 204.

Each of the subsystems 102, 300, 302, and 210 will now be described in greater detail.

A. Illumination Subsystem

Figure 6:
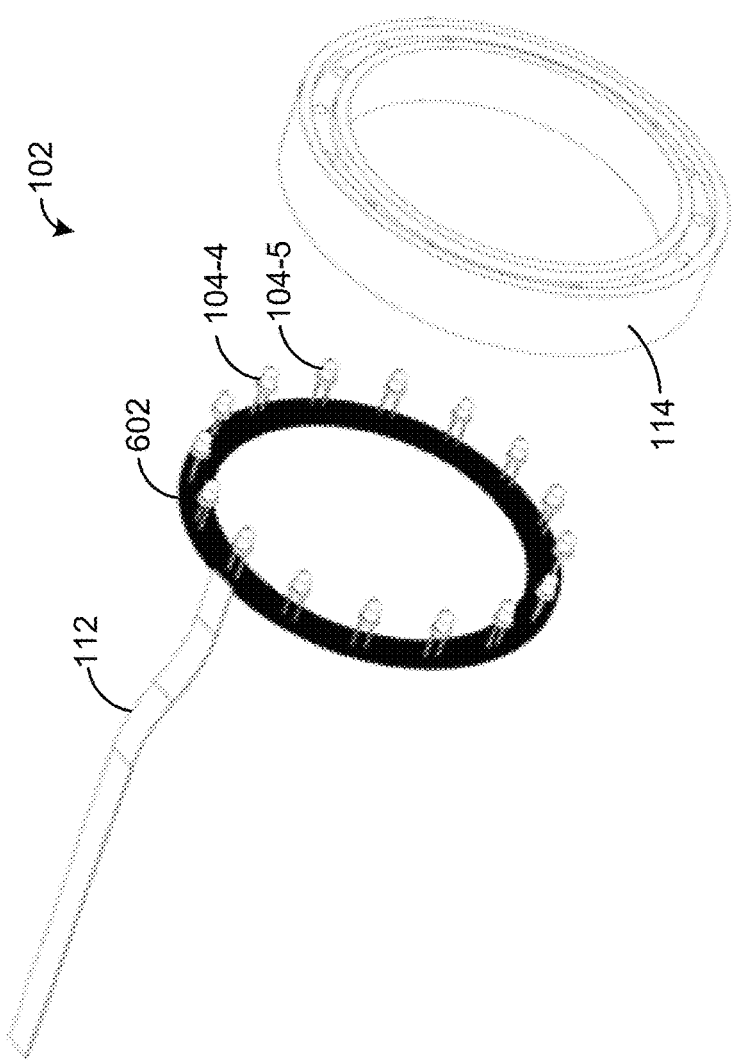
FIG. 6 is a schematic illustration of the illumination subsystem of a co-axial hyperspectral/multispectral camera, according to some embodiments. The illustration shows an exploded view of the components of the illumination subsystem.

FIG. 6 shows an exploded view of the illumination subsystem 102 of a co-axial hyperspectral/multi spectral camera, according to some embodiments. The illumination subsystem includes a plurality of lights 104 mounted on a printed circuit board (PCB; 602) in electrical communication with a CPU, the CPU optionally mounted or otherwise in electrical communication with a motherboard 110, by means of a flex circuit or wire 112. The lights 104 are disposed on the surface of the hyperspectral/multispectral imaging system (e.g., camera), for example, by being mounted in an illumination subsystem housing 114.

As described herein, whereas the lights may be completely contained within the camera housing (e.g., shielded from the external environment), they will be considered to be disposed on the exterior of the housing so long as they are in optical communication with the external environment. For example, in certain embodiments, lights disposed on the exterior of the camera housing may be behind one or more layers of glass, plastic, or film to protect the lights from the external environment. In addition, the one or more layers of glass, plastic, or film may have filtering, polarizing, homogenizing, or focusing properties.

In certain embodiments, one or more of the light sources 104 may be covered by any combination of a focusing lens, a homogenizer, a polarizer, and a wavelength filter. In one embodiment, different lights may be covered by different combinations of filtering elements. For example, in one embodiment, a plurality of lights 104 disposed on the surface of a hyperspectral/multispectral imaging system (e.g., a co-axial camera) includes one or more narrow-band light source (e.g., a mono-wavelength LED) for capturing images that will be assembled into a hyperspectral/multispectral data cube and at least one broad-band light source (e.g., a white light) for capturing color images used, e.g., to focus or otherwise position an image. In this example, the mono-wavelength light sources may be covered by a light homogenizer and/or light polarizer, as desired for uniform illumination of the subject and improved signal-to-noise ratio for the resolved image, while the broad-band light source need not be homogenized or polarized.

The illumination sources may be arranged in any fashion on the imaging system. In certain embodiments, lights 104 will be arranged in one or more concentric circles about the objective lens 106 of an imaging system. In certain embodiments including a plurality of narrowband lights 104, two or more lights 104 emitting radiation of the same wavelength(s) may be illuminated at the same time. In certain embodiments, the two or more lights emitting radiation of the same wavelength(s) are positioned with radial symmetry about the objective lens 106 to provide homogenous illumination of the target. In certain embodiments, where the imaging system includes a plurality of narrow-band illumination sources, one or more broadband illumination source(s) may also be included, for example, for use in capturing a broadband image of the object or subject. Since a broadband image of the object or subject may not necessarily be used in the analysis of collected hyperspectral/multispectral data, the broadband source(s) need not be positioned about or in radial symmetry with the objective lens.

For example, referring to FIG. 4, an imaging device (e.g., hyperspectral/multispectral camera) capable of illuminating an object at eight wavelengths can have two light sources (104-4 and 104-12), positioned symmetrically about the objective lens 106, which emit radiation having the same wavelength(s), e.g., two identical narrowband LEDs. Likewise, four lights (104-4, 104-8, 104-12, and 104-16), emitting radiation of the same wavelength(s), can be positioned symmetrically about the objective lens. In certain embodiments, the imaging system includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more light sources. In certain embodiments, the imaging system includes at least 2, 3, 4, 5, 6, 7, 8, 9, 10, or more lights emitting radiation at the same wavelength(s), preferably arranged in a symmetrical pattern about the objective lens.

In other embodiments, where the imaging system illuminates the object with broadband light, two or more lights 104, e.g., all of the lights, may be configured to emit broadband radiation. In certain embodiments, all of the broadband light sources 104 may be illuminated at the same time.

In yet other embodiments, where the imaging system illuminates the object with filtered light, two or more lights 104, e.g., all of the lights, may be configured to emit broadband radiation. The various lights 104 can then be covered by illumination filters rated for different wavelengths, which match filters covering the optical detectors 206.

In certain embodiments, the illumination filters are removable from the exterior of the housing. Likewise, in certain embodiments, the detector filters are removable from the interior of the housing. In this fashion, different illumination and/or detector filter sets can be provided for use in evaluating different medical conditions. For example, in some implementations, a user positions a first illuminator and/or detector filter set on the imaging system to aid in the evaluation of a first medical condition (e.g., ulcer formation) and a second illuminator and/or detector filter set on the imaging system to aid in the evaluation of a second medical condition (e.g., melanoma). In one example, the first filter set includes filters rated for wavelengths used, for example, to quantify oxyhemoglobin and deoxyhemoglobin levels, while the second filter set includes filters rated for wavelengths used, for example, to discriminate between melanoma and other pigmented legions (e.g., Spitz nevus, seborrheic keratosis, basal cell carcinoma, and melanocytic nevus; see, Nagaoka T. et al., Skin Res Technol. (2011) Aug. 31).

1. Light Sources

In various embodiments, light sources emitting radiation in the ultraviolet spectrum (wavelengths from about 10 nm to about 400 nm), visible spectrum (wavelengths from about 400 nm to about 760 nm), and/or near-infrared spectrum (wavelengths from about 760 nm to about 2000 nm) are used in the hyperspectral/multispectral imaging systems and methods provided herein.

The hyperspectral/multispectral imaging systems described herein will generally include at least one light source for illuminating a region of interest on a subject. In various examples, the light source includes a single broadband light source, a plurality of broadband light sources, a single narrowband light source, a plurality of narrowband light sources, or a combination of one or more broadband light source and one or more narrowband light source. Likewise, in various embodiments, the light source includes a plurality of coherent light sources, a single incoherent light source, a plurality of incoherent light sources, or a combination of one or more coherent and one or more incoherent light sources.

By "broadband" it is meant light that includes component wavelengths over a substantial portion of at least one band, e.g., over at least 20°/%, or at least 30%, or at least 40%, or at least 50%, or at least 60%, or at least 70%, or at least 80%, or at least 90%, or at least 95% of the band, or even the entire band, and optionally includes component wavelengths within one or more other bands. A "white light source" is considered to be broadband, because it extends over a substantial portion of at least the visible band. In certain embodiments, broadband light includes component wavelengths across at least 100 nm of the electromagnetic spectrum. In other embodiments, broadband light includes component wavelengths across at least 150 nm, 200 nm, 250 nm, 300 nm, 400 nm, 500 nm, 600 nm, 700 nm, 800 nm, or more of the electromagnetic spectrum.

By "narrowband" it is meant light that includes components over only a narrow spectral region, e.g., less than 20%, or less than 15%, or less than 10%, or less than 5°/%, or less than 2%, or less than 1%, or less than 0.5% of a single band. Narrowband light sources need not be confined to a single band, but can include wavelengths in multiple bands. A plurality of narrowband light sources may each individually generate light within only a small portion of a single band, but together may generate light that covers a substantial portion of one or more bands, e.g., may together constitute a broadband light source. In certain embodiments, broadband light includes component wavelengths across no more than 100 nm of the electromagnetic spectrum (e.g., has a spectral bandwidth of no more than 100 nm). In other embodiments, narrowband light has a spectral bandwidth of no more than 90 nm, 80 nm, 75 nm, 70 nm, 60 nm, 50 nm, 40 nm, 30 nm, 25 nm, 20 nm, 15 nm, 10 nm, 5 nm, or less of the electromagnetic spectrum.

As used herein, the "spectral bandwidth" of a light source refers to the span of component wavelengths having an intensity that is at least half of the maximum intensity, otherwise known as "full width at half maximum" (FWHM) spectral bandwidth. Many light emitting diodes (LEDs) emit radiation at more than a single discreet wavelength, and are thus narrowband emitters. Accordingly, a narrowband light source can be described as having a "characteristic wavelength" or "center wavelength," i.e., the wavelength emitted with the greatest intensity, as well as a characteristic spectral bandwidth, e.g., the span of wavelengths emitted with an intensity of at least half that of the characteristic wavelength.

By "coherent light source" it is meant a light source that emits electromagnetic radiation of a single wavelength in phase. Thus, a coherent light source is a type of narrowband light source with a spectral bandwidth of less than 1 nm. Non-limiting examples of coherent light sources include lasers and laser-type LEDs. Similarly, an incoherent light source emits electromagnetic radiation having a spectral bandwidth of more than 1 nm and/or is not in phase. In this regard, incoherent light can be either narrowband or broadband light, depending on the spectral bandwidth of the light.

Examples of suitable broadband light sources 104 include, without limitation, incandescent lights such as a halogen lamp, xenon lamp, a hydrargyrum medium-arc iodide lamp, and a broadband light emitting diode (LED). In some embodiments, a standard or custom filter is used to balance the light intensities at different wavelengths to raise the signal level of certain wavelength or to select for a narrowband of wavelengths. Broadband illumination of a subject is particularly useful when capturing a color image of the subject or when focusing the hyperspectral/multispectral imaging system.

Examples of suitable narrowband, incoherent light sources 104 include, without limitation, a narrow band light emitting diode (LED), a superluminescent diode (SLD) (see, Redding B., arVix: 1110.6860 (2011), the content of which is hereby incorporated herein by reference in its entirety for all purposes), a random laser, and a broadband light source covered by a narrow band-pass filter. Examples of suitable narrowband, coherent light sources 104 include, without limitation, lasers and laser-type light emitting diodes. While both coherent and incoherent narrowband light sources 104 can be used in the imaging systems described herein, coherent illumination is less well suited for full-field imaging due to speckle artifacts that corrupt image formation (see, Oliver, B. M., *Proc IEEE* 51, 220-221 (1963)). However, coherent illumination is particularly well suited for embodiments comprising a scanning detection device.

In one embodiment, light emitted from a light source 104 passes through an illumination lens, which focuses the light onto a target (e.g., the skin of a subject). In a related embodiment, light emitted from a light source 104 passes through an optical diffuser or light homogenizer, that modifies the focal properties of the light so that it illuminates selected regions of a target in a substantially uniformly fashion. That is, the intensity of light at one point in the region is substantially the same as the intensity of light at another point in the region. In other embodiments, the intensity of the light varies from one point within the region to the next. In certain embodiments, a light source 104 is covered by both an illumination lens and a homogenizer.

In certain embodiments, the light also passes through an optional illumination polarizer, which removes any light that does not have a selected polarization. The polarizer can be, for example, a polarizing beamsplitter or a thin film polarizer. The polarization can be selected, for example, by rotating the polarizer appropriately. When an illumination polarizer is placed in front of a light source 104, a matching detector polarizer should be placed in front of the corresponding optical detector 206 to depolarize the light prior to resolving an image of the backscattered polarized light.

a. Light Emitting Diodes (LEDs)

In a preferred embodiment, the illumination subsystem 102 comprises one or more light emitting diodes (LEDs; 104) for illuminating the surface of a patient. LEDs provide several advantages over other light sources for illuminating the surface of a subject. For example, because LEDs generate very little heat, illumination with LEDs does not affect the surface temperature of a subject's skin, which results in physiological changes that can alter hyperspectral/multispectral analysis. LEDs can be constructed to emit light having a narrow and defined spectral band, negating a requirement to filter the illumination light, improving the overall efficiency of the imaging system, improving the signal-to-noise ratio of detection at a desired wavelength, and decreasing the illumination and exposure times necessary to produce a high quality digital image of the target. LEDs reach maximum intensities very rapidly, for example a red LED can achieve full brightness in under a microsecond, allowing for faster cycling through a plurality of illumination wavelengths. LEDs have a long useful lifetime, as compared to incandescent and fluorescent light sources. LEDs can be manufactured to be very small (e.g., from about 2 mm to about 8 mm), allowing for many LEDs to be mounted in one or more concentric circles about an objective lens 106.

LEDs consist of a chip of semiconducting material doped with impurities, which create the formation of a p-n junction. Current applied across the semiconducting material readily flows from the p-side (anode) to the n-side (cathode), creating electromagnetic radiation (light) when an electron meets a hole and falls from the conduction band to the valence band. The wavelength of the emitted radiation is dependent on the size of the band gap formed between the conduction band and the valence band, and thus the semiconducting material used to form the LED. Non-limiting examples of semiconductor materials that can be used to produce an LED emitting light at a specific wavelength are provided in Table 2.

TABLE 2

Semiconducting materials used for narrowband LEDs.

| Color | Wavelength (nm) | Semiconductor Material |
|---|---|---|
| Infrared | $\lambda > 760$ | Gallium arsenide (GaAs) |
| | | Aluminium gallium arsenide (AlGaAs) |
| Red | $610 < \lambda < 760$ | Aluminium gallium arsenide (AlGaAs) |
| | | Gallium arsenide phosphide (GaAsP) |
| | | Aluminium gallium indium phosphide (AlGaInP) |
| | | Gallium(III) phosphide (GaP) |
| Orange | $590 < \lambda < 610$ | Gallium arsenide phosphide (GaAsP) |
| | | Aluminium gallium indium phosphide (AlGaInP) |
| | | Gallium(III) phosphide (GaP) |
| Yellow | $570 < \lambda < 590$ | Gallium arsenide phosphide (GaAsP) |
| | | Aluminium gallium indium phosphide (AlGaInP) |
| | | Gallium(III) phosphide (GaP) |
| Green | $500 < \lambda < 570$ | Indium gallium nitride (InGaN)/Gallium(III) nitride (GaN) |
| | | Gallium(III) phosphide (GaP) |
| | | Aluminium gallium indium phosphide (AlGaInP) |
| | | Aluminium gallium phosphide (AlGaP) |
| Blue | $450 < \lambda < 500$ | Zinc selenide (ZnSe) |
| | | Indium gallium nitride (InGaN) |
| | | Silicon carbide (SiC) as substrate |
| Violet | $400 < \lambda < 450$ | Indium gallium nitride (InGaN) |
| Ultraviolet | $\lambda < 400$ | Diamond (235 nm) |
| | | Boron nitride (215 nm) |
| | | Aluminium nitride (AlN) (210 nm) |
| | | Aluminium gallium nitride (AlGaN) |
| | | Aluminium gallium indium nitride (AlGaInN) - (down to 210 nm) |

In one embodiment, the LEDs 104 are packaged LEDs, such as the LUXEON® Rebel (Philips Lumileds Lighting). Other types of packaged LEDs may also be used, such as those manufactured by OSRAM (Ostar package), Luminus Devices (USA), or Tridonic (Austria). As defined herein, a packaged LED is an assembly of one or more LED die that contains electrical connections, such as wire bond connections or stud bumps, and possibly includes an optical element and thermal, mechanical, and electrical interfaces. The LEDs 104 may include a lens over the LED chips. Alternatively, LEDs without a lens may be used. LEDs without lenses may include protective layers, which may include phosphors. The phosphors can be applied as a dispersion in a binder, or applied as a separate plate.

The LED semiconductor chips are typically potted in a clear or colored molded plastic shell, which: facilitates mounting of the LED semiconductor chip in the illumination subsystem housing 114, provides structural protection for the semiconductor chip and associated electrical wiring, and acts as a refractive intermediary between the relatively high-index semiconductor and low-index open air, boosting the light emission from the semiconductor by acting as a diffusing lens, allowing light to be emitted at a much higher angle of incidence from the light cone than the bare chip is able to emit alone.

In certain embodiments, the hyperspectral/multispectral imaging systems provided herein include narrowband width LED lights. In one embodiment, the narrowband LED lights have a FWHM spectral bandwidth or less than about 100 nm, preferably less than about 50 nm, more preferably less than 25 nm. In one embodiment, the imaging system includes at least one LED source that emits radiation in the infrared, preferably near-infrared, spectrum. The use of near-infrared LED illumination in is commonly found in closed circuit security cameras.

For additional information on light emitting diodes, see, Schubert E. F., *Light Emitting Diodes*, Second Edition, Cambridge University Press (2006), the content of which is hereby incorporated herein by reference in its entirety for all purposes.

b. Specific Embodiments

In a first embodiment, the hyperspectral/multispectral imaging system includes a single broadband light source 104 used for illuminating a tissue on the subject. In order to acquire a plurality of images, where each respective image corresponds to the backscattering of a different wavelength of light from the tissue, each of the optical detectors 206 are covered by a narrow band-pass filter. In this embodiment, wavelengths of light over a large band that includes all the wavelengths of interest are used simultaneously to illuminate the tissue and detector filters are used as a means of wavelength selection, where the optical detectors are exposed to backscattered light either simultaneously or sequentially.

To acquire hyperspectral/multispectral data, in one corresponding embodiment, the imaging system illuminates a selected region (e.g., tissue) of the subject with the broadband light source 104, and light backscattered from the illuminated region of the subject is focused by the objective lens assembly 202 onto the beam steering element 204. While the selected region is illuminated, the imaging system's CPU 1308 cycles the beam steering element 204 through a plurality of operating modes, where each operating mode places the beam steering element 204 in optical communication with a corresponding optical detector 206. This directs the backscattered light sequentially to the corresponding optical detectors 206, each of which are covered by a different narrow band-pass filter, providing a series of co-axial digital images of the selected region at the wavelengths corresponding to the corresponding narrow band-pass filters.

In a second embodiment, the hyperspectral/multispectral imaging system includes a plurality of broadband light sources 104 used for illuminating a region (e.g., tissue) on the subject. Each of the broadband light sources 104 is covered by a narrow band-pass filter so that each light source illuminates the selected region with narrowband light. In this embodiment, each of the optical detectors 206 used to resolve images for assembly into a hyperspectral/multispectral data cube are covered by a narrow band-pass filter that corresponds with a narrow band-pass filter covering a respective light source. Light sources 104 and optical detectors 206 that are covered by identical or substantially similar filters and/or polarizers are termed "matching" elements herein.

In one corresponding embodiment, one wavelength at a time is used to illuminate the subject and backscattered light at that wavelength is detected using an optical detector 206 covered by a matching filter. That wavelength is then turned off and the same is done for the next selected wavelength, in a stepwise process to capture a co-axial hyperspectral/multispectral image (e.g., hyperspectral/multispectral data cube). In another embodiment, more than one wavelength of light is used to illuminate the subject at a time and backscattered light is resolved using matching filtered optical detectors 206, either simultaneously, nearly simultaneously, or sequentially.

To acquire hyperspectral/multispectral data in one corresponding embodiment, the light sources 104 are turned on and off in sequence, illuminating a selected region on a subject with one type of filtered light at a time. The operating modes of the beam steering element 204 are coordinated with the light sources such that when a light source 104 covered by a particular illumination filter is turned on, the beam steering element 204 is placed in optical communication with an optical detector 206 covered with a matching detector filter.

In a third embodiment, the hyperspectral/multispectral imaging system includes a plurality of narrowband light sources 104 used for illuminating a region of skin on the subject, preferably without wavelength illumination filters. In this embodiment, each of the optical detectors 206 used to resolve images for assembly into a hyperspectral/multispectral data cube are covered by a narrow band-pass filter matching the narrowband light emitted by a corresponding light source.

To acquire hyperspectral/multispectral data in one corresponding embodiment, the light sources 104 are turned on and off in sequence, illuminating a selected region on a subject with one wavelength at a time. The operating modes of the beam steering element 204 are coordinated with the light sources such that when a light source 104 emitting a first wavelength is turned on, the beam steering element 204 is placed in optical communication with an optical detector 206 covered with a matching detector filter.

The above embodiments, describing use of either broadband or narrowband illumination, are in no way limiting and include embodiments where the hyperspectral/multispectral imaging system includes a combination of both types of light sources 104. For example, in certain embodiments, where narrowband light sources 104 are used to illuminate a region of interest on a subject, a broadband light source may be present to provide illumination for, e.g., acquiring a color image of the selected region or focusing the system.

Although embodiments employing both simultaneous, near simultaneous, and sequential illumination are provided herein, sequential illumination and detection is preferred because it results in lower signal to noise performance. Strong narrowband illumination at a desired wavelength (in-band illumination) coupled with matching narrow band optical filters covering the optical detectors 206 simultaneously increases in-band illumination while decreasing out-of-band illumination (e.g., detection of non-desired wavelengths).

Furthermore, although illumination filters are present in several of the embodiments provided herein, the use of non-filtered light, particularly non-filtered, narrowband light, is preferred. By filtering a light source 104, unused light is generated by the hyperspectral/multispectral imaging system, which is inefficient and unnecessarily increases the power requirements of the system.

2. Focusing Lenses

In certain embodiments, an illumination lens is placed over one or more lights 104 disposed on the surface of a hyperspectral/multispectral imaging system to shape the light toward the target and focus it as a spot that is appropriate for the focal distance of the objective imaging lens. In certain embodiments, the focusing lens will also improve the uniformity of light directed onto the target. A diffuser may also be placed over one or more lights 104 to cause the incident illumination on the subject or object to be diffuse.

Illumination lenses are well known in the art. For example, U.S. Pat. No. 8,025,429, the content of which is hereby incorporated herein by reference in its entirety for all purposes, describes an optical lens which refracts light emitted by an LED illuminator twice, providing a more uniform beam of light with an elliptical shape. U.S. Patent Application Publication No. 2010/0165637, the content of which is hereby incorporated herein by reference in its entirety for all purposes, describes an optical lens adaptable for LED illuminators which employs shaping of the surface of the lens to distribute light in a highly controlled manner with minimum loss due to reflection. Similarly, Ding Y. et al., Optics Express, 16:17; 12958-12966 (2008), the content of which is hereby incorporated herein by reference in its entirety for all purposes, describes the use of freeform optical lenses designed based on Snell's law and energy conservation to provide shaped and uniform illumination from LED light sources.

3. Homogenizing Filters

In certain embodiments, a light homogenizer is placed over one or more lights 104 disposed on the surface of a hyperspectral/multispectral imaging system to provide uniform illumination of an area on a target object or subject. An exemplary light homogenizer that can be used are the light homogenizers disclosed in Agilent Technologies Application Brief I-003, *Light Guide Techniques Using LED Lamps*, Agilent Technologies (2001), the content of which is hereby incorporated herein by reference in its entirety for all purposes. The reference describes the use of light guides to direct and homogenize light emitted from LED lamps. Commercial LED light homogenizers are available, for example, from RPC Photonics (Rochester, N.Y.).

4. Polarizing Filters

In certain embodiments, polarizing lens is placed over one or more lights 104 disposed on the surface of a hyperspectral/multispectral imaging system to polarize light illuminating a target object or subject. Polarized illumination is advantageous because it eliminates surface reflection from the skin and helps to eliminate stray light reflection from off axis imaging directions. In some embodiments, when a polarizer is placed over an illumination source, a second polarizer is placed in front of a corresponding optical detector 206 to depolarize the light prior to resolution of an image by the detector. In certain embodiments, where multiple light sources on the imaging system are polarized, a polarizing lens is placed over the objective lens or otherwise upstream of the beam steering element, such that a single polarizer is used to depolarize the image. In other embodiments, individual polarizers are placed between the beam steering element and individual optical detectors. In certain embodiments, the detector polarizing lens is selected from a linear polarizer, a circular polarizer, and an elliptical polarizer.

U.S. Pat. No. 5,929,443 to Alfano et al., the content of which is hereby incorporated herein by reference in its entirety for all purposes, discloses a method and apparatus for the imaging of objects based on the polarization and depolarization of light. In one embodiment, a surface of a turbid medium is imaged by illuminating the surface of the turbid medium with light, whereby light is backscattered from the illuminated surface of the turbid medium, detecting a pair of complementary polarization components of the backscattered light, and forming an image of the illuminated surface using the pair of complementary polarization components. The illuminating light is preferably polarized (e.g., linearly polarized, circularly polarized, elliptically polarized), where, for example, the illuminating light is linearly polarized, the pair of complementary polarization components are preferably the parallel and perpendicular components to the polarized illuminating light, and the image is formed by subtracting the perpendicular component from the parallel component, by taking a ratio of the parallel and perpendicular components or by using some combination of a ratio and difference of the parallel and perpendicular components.

5. Illumination Wavelength Filters

In certain embodiments, where broadband lights are used to illuminate an object or subject, a wavelength filter is placed over the broadband light to increase the percentage of a desired wavelength of light. The illumination filter is matched to a corresponding detector filter, to increase the signal-to-noise ratio of an image captured at the desired wavelength. In certain embodiments, the illumination filter is selected from a bandpass filter, a longpass filter, and a shortpass filter.

As with light sources, filters can be described in terms of their spectral "bandpass," e.g., the span of component wavelengths allowed to pass through the filter. In some embodiments, the bandpass of a filter is defined as the span of component wavelengths at which the filter is at least half as transparent as compared to the characteristic or center wavelength (FWHM). For example, the spectral bandpass of a filter that is 100% transparent with respect to at least one component wavelength is the span of consecutive component wavelengths at which the filter is at least 50% transparent. In certain embodiments, the bandpass of a filter can be equivalently expressed in terms of the component wavelengths (e.g., 450-480 nm) or as the width of the bandpass at the central wavelength (e.g., 30 nm at 465 nm or ±15 nm at 465 nm).

A bandpass filter can also be described in terms of its "characteristic wavelength," e.g., the wavelength at which the filter is most transparent, or its "center wavelength," e.g., the component wavelength at the midpoint of the spectral bandpass. In certain embodiments, the bandpass filter is characterized by both its characteristic or center wavelength and its spectral bandwidth. For example, a bandpass filter with a center wavelength of 340±2 nm, a FWHM bandwidth of 10±2, and a peak transmission (e.g., the maximum percentage transmission within the passband) of 50%, allows at least 25% of each component light having a wavelength from 330±4 nm to 350±4 nm to pass through.

In specific embodiments, the illumination wavelength filter is a bandpass filter, e.g., a filter that allows only radiation having a wavelength in a certain range to pass, while blocking passage of other wavelengths. In certain embodiments, the FWHM spectral bandpass of an illumination filter (e.g., the size of the passband transmitted through the filter) is no more than about 100 nm, preferably no more than about 50 nm, more preferably no more than about 25 nm. In yet other embodiments, the FWHM spectral bandwidth of the filter is no more than 250 nm, 200 nm, 200 nm, 175 nm, 150 nm, 150 nm, 125 nm, 100 nm, 90 nm, 80 nm, 75 nm, 70 nm, 65 nm, 60 nm, 55 nm, 50 nm, 45 nm, 40 nm, 35 nm, 30 nm, 25 nm, 20 nm, 15 nm, 10 nm, 9 nm, 8 nm, 7 nm, 6 nm, 5 nm, 4 nm, 3 nm, 2 nm, or 1 nm.

In certain embodiments, the bandpass filter is a narrow pass filter. In specific embodiments, the narrow pass filter has a FWHM spectral bandwidth of no more than 25 nm, 24 nm, 23 nm, 22 nm, 21 nm, 20 nm, 19 nm, 18 nm, 17 nm, 16 nm, 15 nm, 14 nm, 13 nm, 12 nm, 11 nm, 10 nm, 9 nm, 8 nm, 7 nm, 6 nm, 5 nm, 4 nm, 3 nm, 2 nm, or 1 nm.

In some embodiments, the plurality of bandpass illumination filters have central wavelengths that are separated by at least 10 nm, or at least 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, or more.

In some embodiments, the hyperspectral/multi spectral imaging system comprises a matching set of illumination bandpass filters and detector bandpass filters. In some embodiments, respective illumination and detector bandpass filters having the same or substantially similar central or characteristic wavelengths and spectral bandpasses are used to provide in-band illumination and imaging. As described herein, in-band illumination and imaging substantially reduces background noise while decreasing the required illumination and detector exposure times.

B. Lens Subsystem

Light backscattered from the object or subject passes through an objective lens 106 or objective lens assembly 202, which focuses the light on the beam steering element 204. In certain embodiments, the lens 106 may comprise a simple convex lens. In other embodiments, the lens subsystem will include a compound lens. The compound lens can be a fixed focus lens or a variable focus lens.

A fixed focus lens refers to a lens whose focus is set at the time of manufacture. Typically, the focus of a fixed focus lens will be set to the hyperfocal distance, which s a distance beyond which all objects can be brought into an acceptable focus. To obtain a short minimal focal distance, the aperture and the focal length of a fixed focus lens are reduced, so that the hyperfocal distance is small. This allows the depth of field to extend from infinity to a short distance. Because a fixed focus lens requires no moving parts, no electrical power is required to operate the lens. This is advantageous for building a low power hyperspectral/multispectral camera, especially one that operates on battery power. The disadvantage of a fixed focus lens is that it cannot produce images that are as sharp as those obtained using a variable focus lens.

A variable focus lens, also known as a zoom lens, refers to a compound lens assembly that can be manipulated to change the focal length. Variable focus is achieved by moving one or more lens relative to one or more additional lenses present in the lens assembly. Because of the complexity of a variable focus lens, as compared to fixed focus lens, variable focus lenses are more expensive to manufacture. However, the image quality obtainable by a variable focus lens is higher than that of a fixed focus lens. Variable focus lenses can be parfocal or varifocal. A parfocal lens, also referred to as a true focus lens, maintains focus when the focal length is changes, whereas a varifocal lens losses focus during zooming.

In some embodiments, a variable focus lenses is a manual focus lens, e.g., one that requires the user to focus an image. Manual focus lenses can be designed to be controlled by rotating the barrel of a lens assembly, causing lenses within the lens assembly to move on tracks, or by instructing motors within the camera to move the lenses, for example with control buttons or input on a touch screen.

Figure 13:
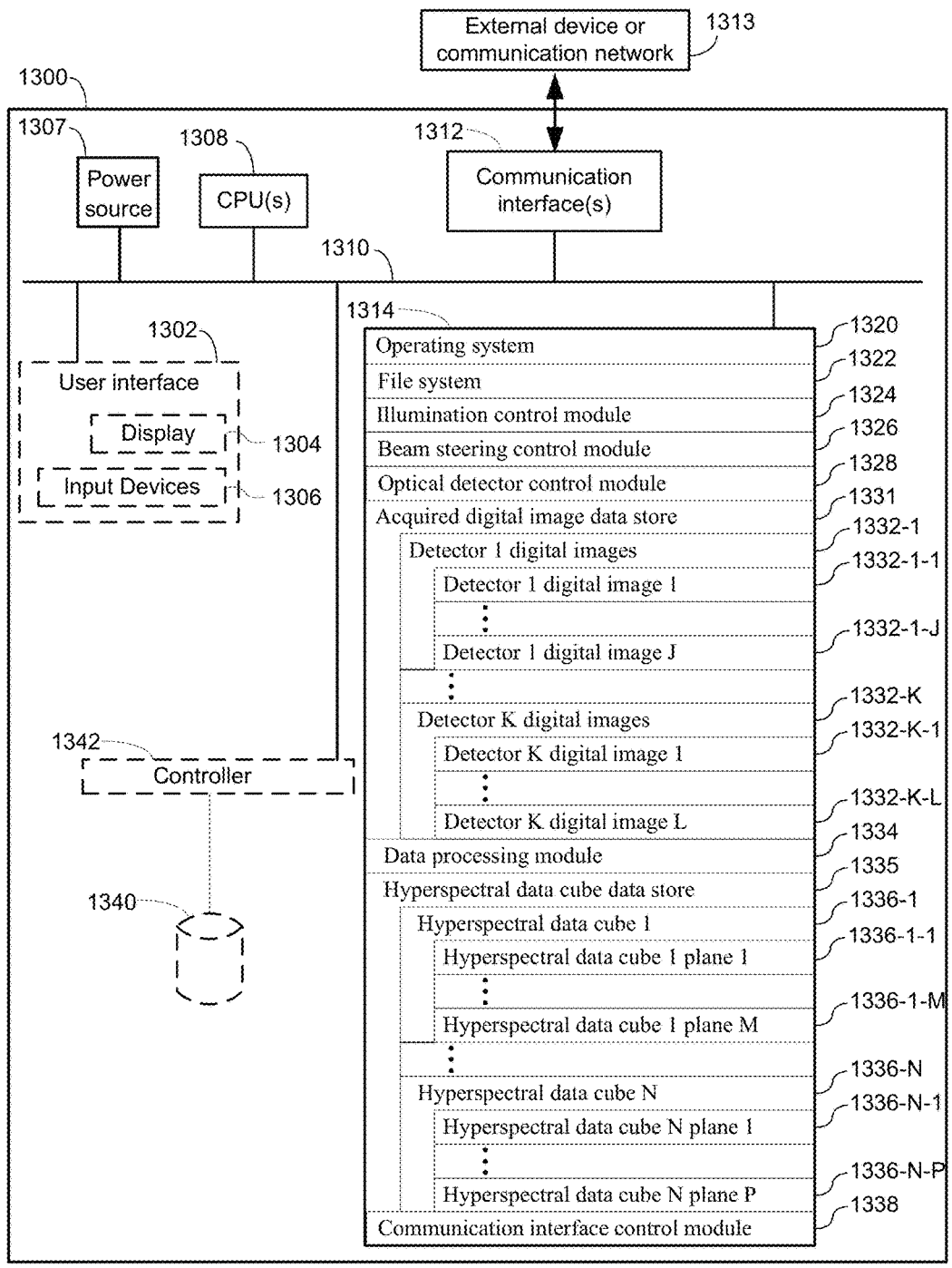
FIG. 13 schematically illustrates a processing subsystem for a co-axial hyperspectral/multispectral system, according to some embodiments.

In other embodiments, the variable focus lens is an autofocus lens, one that is focused electronically by a sensor, control system, and motor mounted within the camera. Referring to FIG. 13, an autofocus lens can be controlled by a lens software module stored in the system memory 1314 of the processor subsystem 1300, which provides instructions to a motor mounted within the housing of the camera to move one or more focusing lenses within the object lens assembly 202 to achieve a desired focus.

In yet other embodiments, a hyperspectral/multispectral variable focus lens has settings for both automatic and manual focus adjustment modes. For example, U.S. Pat. No. 5,675,441, the content of which is hereby incorporated herein by reference in its entirety for all purposes, describes a focusing lens control apparatus that has an electric motor connected to a focusing lens in electrical communication with an automatic focus adjustment control, as well as a manual operation device which operates the motor mechanically in a manual operation mode.

C. Light Directing Subsystem

Figure 15:
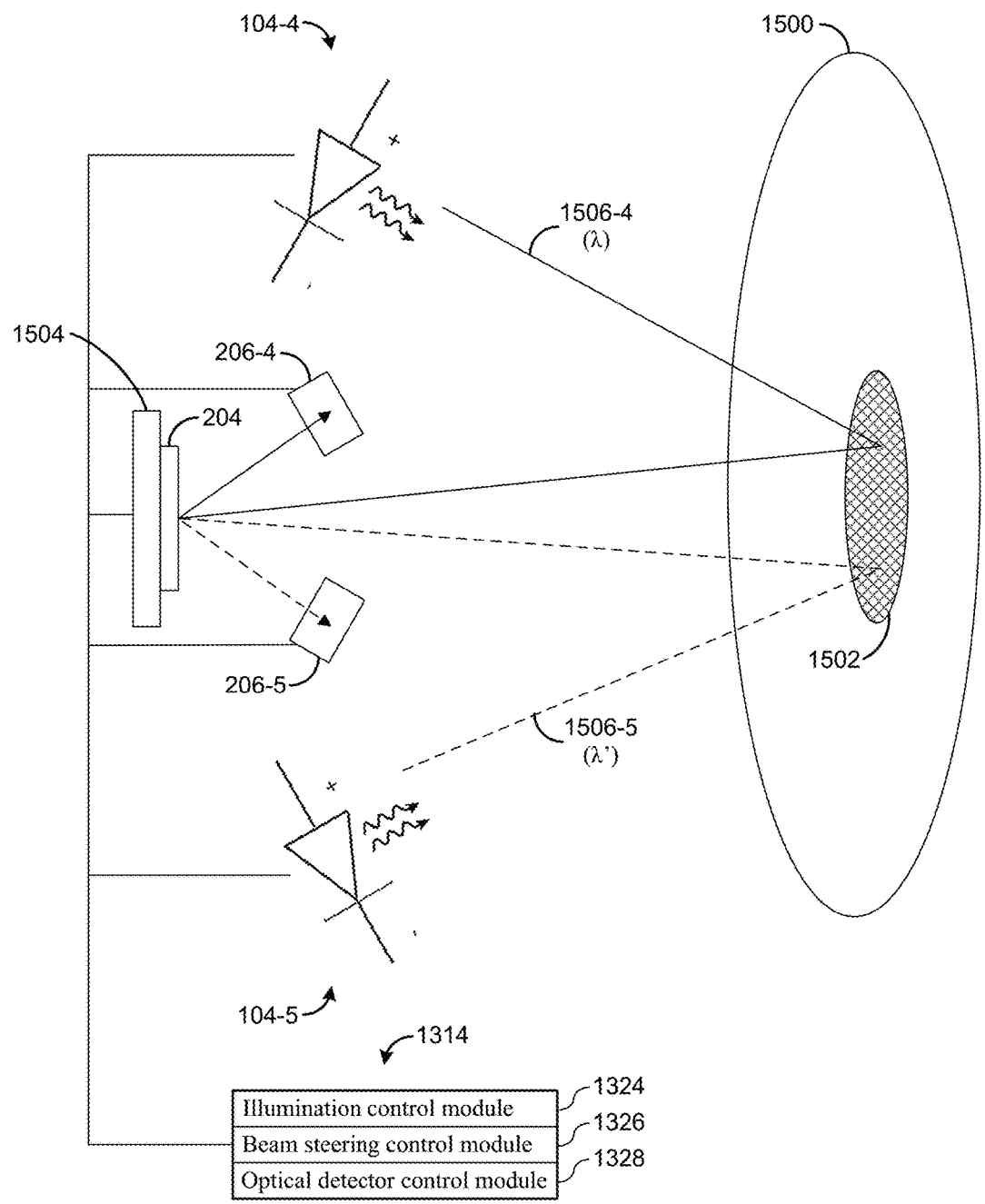
FIG. 15 is a schematic illustration of the light path for a captured hyperspectral/multispectral image, according to some embodiments.

Referring to FIG. 15, light 1506 having a first wavelength ($\lambda$), emitted from a light source 104, reflects or backscatters from a region of interest (1502; ROI) on an object or subject 1500. The light 1506 passes through the objective lens assembly (not shown) and is directed by a beam steering element 204, positioned in a first operating mode in a plurality of operating modes, towards an optical detector 206 configured to resolve light of the first wavelength ($\lambda$). In certain embodiments, the beam steering element is positioned in its respective operating modes through the use of an actuator 1504 capable of adjust tip and tilt angles of the beam steering element.

In certain embodiments, the actuator 1504 is a tip-tilt actuator that rotates the beam steering element 204 on two-axes. Through the movement of the actuator 1504, the beam steering element 204 is placed in optical communication with respective optical detectors 206. In certain embodiments, the actuator 1504 is a MEMS actuator, e.g., a comb type MEMS actuator (see, U.S. Pat. No. 7,295,726 to Milanovic et al., the content of which is hereby incorporated by reference in its entirety for all purposes) or a tip-tilt-piston MEMS actuator (see, Milanovic et al., IEEE Journal of Selected Topics in Quantum Electronics, Vol. 10, No. 3, May/June 2004:462-471, the content of which is hereby incorporated by reference in its entirety for all purposes).

In some embodiments, the actuator 1504 is a gimbal device capable of tilting off of the vertical and horizontal axes. For example, Texas Instruments (Dallas, Tex.) manufactures dual-axis analog MEMS pointing mirrors (e.g., the TALP1000B) comprising a single-surfaced gimbaled mirror that can be integrated into a hyperspectral/multispectral imaging system described herein for precise light steering. In certain embodiments, the mirror is constructed of single crystal silicon, preferably having no grain boundaries. In certain embodiments, the mirrored surface is gold coated. In certain embodiments, the MEMS device is electromagnetically driven, allowing operation at low-voltage and low-power.

In some embodiments, the mirror is a micromirror or array thereof. In certain embodiments, the surface of the micromirror is no more than 0.01 mm$^2$, 0.02 mm$^2$, 0.03 mm$^2$, 0.04 mm$^2$, 0.05 mm$^2$, 0.06 mm$^2$, 0.07 mm$^2$, 0.08 mm$^2$, 0.09 mm$^2$, 0.1 mm$^2$, 0.2 mm$^2$, 0.3 mm$^2$, 0.4 mm$^2$, 0.5 mm$^2$, 0.6 mm$^2$, 0.7 mm$^2$, 0.8 mm$^2$, 0.9 mm$^2$, or 1.0 mm$^2$. In other embodiments, the surface of the mirror is at least 1 mm$^2$, 2 mm$^2$, 3 mm$^2$, 4 mm$^2$, 5 mm$^2$, 6 mm$^2$, 7 mm$^2$, 8 mm$^2$, 9 mm$^2$, 10 mm$^2$, 11 mm$^2$, 12 mm$^2$, 13 mm$^2$, 14 mm$^2$, 15 mm$^2$, 16 mm$^2$, 17 mm$^2$, 18 mm$^2$, 19 mm, 20 mm$^2$, 21 mm$^2$, 22 mm$^2$, 23 mm$^2$, 24 mm$^2$, 25 mm$^2$, 30 mm$^2$, 35 mm$^2$, 40 mm$^2$, 45 mm$^2$, 50 mm$^2$, or larger.

In some embodiments, control modules, stored in the system memory 1314 control: the illumination, via an illumination control module 1324, the direction of the beam towards one or more optical detectors 206 via a beam steering control module 1326, and the image exposure time and optical detectors themselves via an optical detector control module 1328. The beam steering control module 1326 directs actuator 1504 to place the beam steering element 204 in various operating modes, each of which is in optical communication with one of the optical detectors 206.

For example, to collect images of an object 1500 for hyperspectral/multispectral analysis at two different wavelengths, λ and λ', the illumination control module 1324 turns on a first light 104-4, emitting light 1506-4 at a first wavelength (λ), illuminating a region of interest (ROI) 1502 on the subject 1500. Reflected or backscattered light 1506-4 from the subject 1500 enters the objective lens or assembly thereof (not shown) and hits the beam steering element 204, placed in a first operating mode by an actuator 1504 controlled by the beam steering control module 1326, which redirects the light onto an optical detector 206-4 configured to resolve light of wavelength λ. The illumination control module 1324 then turns off the first light 206-4 and turns on a second light 206-5, emitting light 506-5 at a second wavelength (λ'), illuminating the ROI 1502. Simultaneously, the beam steering control module 1328 instructs the actuator 1504 to place the beam steering element 204 in a second operating mode, which is in optical communication with a second optical detector 206-5 configured to resolve light of wavelength λ'. Thus, when reflected or backscattered light 1506-5 hits the beam steering element 204, the light 1506-5 is redirected onto the second optical detector 206-5.

The beam steering element 204 can be one or more reflective elements capable of redirecting the incident beam in one or more directions toward the detector(s). In some embodiments, the beam steering element 204 is an element that reflects light in one or more directions (e.g., a mirror element). In a particular embodiment the beam steering element is a plain mirror capable of reflecting light over a wide range of wavelengths. In another particular embodiment, the beam steering element is an array of mirrors, for example an array of micromirrors.

In one embodiment, the beam steering element consists of more than one element and is capable of simultaneously directing lights of different wavelengths in different directions. In specific embodiments, the beam steering element includes a first hot mirror and a second mirror positioned behind the hot mirror. The hot mirror is suitably coated to reflect light above or below a certain wavelength, while being transparent to light with lower or higher wavelengths, respectively.

For example, in some embodiments a hot mirror is coated to reflect infrared radiation, while allowing visible light to pass through. By orienting the hot mirror in a first operating mode, infrared light is reflected towards a first optical detector configured to resolve the infrared light. At the same time, visible light passes through the hot mirror and is reflected by a second mirror placed in an operating mode in communication with a second optical detector configured to resolve the visible light.

Accordingly, in certain embodiments, a hyperspectral/multispectral imaging system concurrently illuminates an ROI 1502 with a first light source 104-4 emitting infrared radiation 1506-4 and a second light source 104-5 emitting visible light 1506-5. Reflected or backscattered infrared 1506-4 and visible 1506-5 light passing through the objective lens or system thereof (not shown) is projected onto the hot mirror (not shown), which reflects the infrared light 1506-4 onto a first optical detector 206-) configured to resolve the infrared light 1506-4. The visible light 1506-5 passes through the hot mirror and is reflected by a second mirror (not shown) placed in optical communication with a second optical detector 206-5 configured to resolve the visible light.

In certain embodiments, the beam steering element is a chip comprising a micro electromechanical system (MEMS). The MEMS chip generally includes a two-dimensional array of tiltable mirrors which may be separately controlled. U.S. Pat. No. 6,097,859 to Solgaard et al., the content of which is hereby incorporated herein by reference in its entirety for all purposes, describes the functional configuration of such a MEMS wavelength selective switch (WSS), which incorporates a wavelength from an incoming fiber and is capable of switching wavelength(s) to any one of multiple outgoing fibers. The entire switching array of several hundred micro electromechanical system (MEMS) mirrors can be fabricated on a chip having dimension of less than one centimeter by techniques well developed in the semiconductor integrated circuit industry.

In some embodiments, the MEMS device is a digital light processing (DLP) technology, for example, a digital micromirror device (DMD) chip. A DMD chip consists of hundreds to hundreds of thousands of micromirrors arranged in a rectangular array. In certain embodiments, each of the mirrors on a DMD chip will correspond one-to-one with a pixel resolved by an optical detector. The mirrors in a DMD array are individually rotatable ±10-12 degrees about a single axis, allowing for a first and a second operating mode. DMDs used in light projectors operate each micromirror individually, with the two operating modes corresponding to a first "on" state, in which light is projected out through an aperture, and a second "off" state, in which light is diverted elsewhere internal to the projector, for example, into a heat sink. Commercial DMD chips are sold, for example, by Texas Instruments (Dallas, Tex.).

In one embodiment, the two rotatable states of a DMD mirror are each in optical communication with two optical detectors, respectively. Accordingly, two images, collected at two different wavelengths of light, can be collected simultaneously by either toggling a micromirror between its two rotatable states, or by positioning alternating micromirrors in optical communication with different optical detectors. In some embodiments, the DMD chip is further positioned on an actuator having a plurality of operating modes. Thus, when the actuator is in a first operating mode, the DMD mirrors can be in optical communication with a first or a second optical detector, while in a second operating mode, the DMD mirrors can be in optical communication with a third or a fourth optical detector.

In certain embodiments, the use of a MEMS chip having a two-dimensional array of tiltable mirrors allows for line scanning at one or more wavelengths simultaneously. A scanning device refers to line scanning (row or column scanner) or scanning the beam across the field of view of a detector. In certain embodiments, the imaging system line scans to a plurality of small optical detectors (e.g., a single pixel sensor or photocell) so as to further decrease the size and power consumption of the device.

In other embodiments, a scanning mirror is used for line scanning across a field of view. The scanning mirror reflects light from one row of an ROI toward an optical detector, which captures the image. After obtaining light from one row, the scanning mirror then rotates or otherwise moves in order to obtain light from a different row. The scanning mirror continues this rotation until light has been sequentially obtained from each row of the ROI. Mechanisms other than scan mirrors can be used for line scanning of an ROI, such as the focal plane scanner described in Yang et al., "A CCD Camera-based Hyperspectral Imaging System of Stationary and Airborne Applications," Geocarto International, Vol. 18, No. 2, June 2003, the content of which is hereby incorporated herein by reference in its entirety for all purposes.

D. Imager Subsystem

Figure 7:
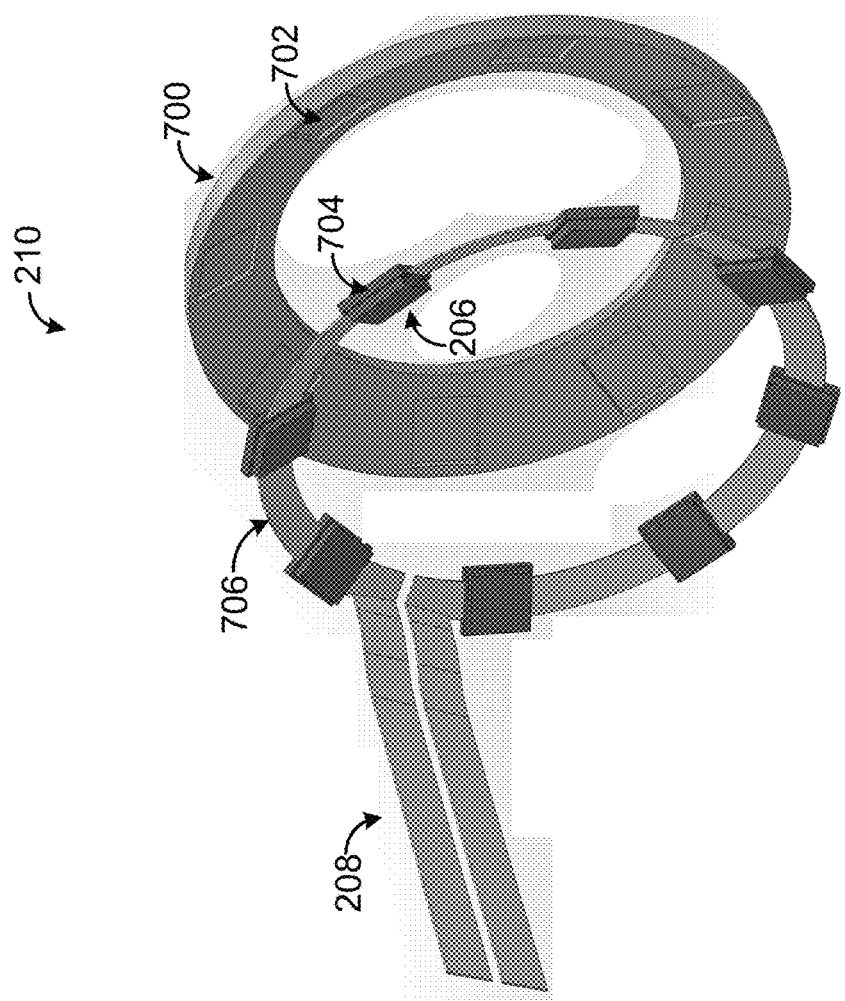
FIG. 7 is a schematic illustration of the imager subsystem of a co-axial hyperspectral/multispectral camera, according to some embodiments. The illustration shows an exploded view of the components of the imager subsystem.
Figure 8A:
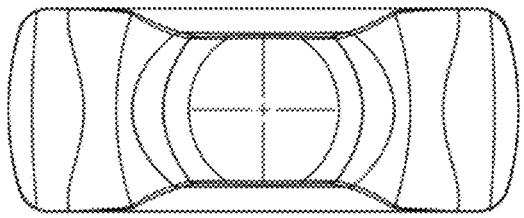
FIGS. 8A-8F are a series of illustrations of a first housing for a co-axial hyperspectral/multispectral camera, according to some embodiments.
Figure 8B:
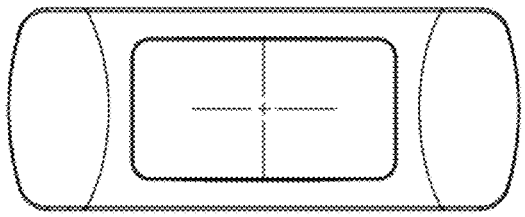
Figure 8C:
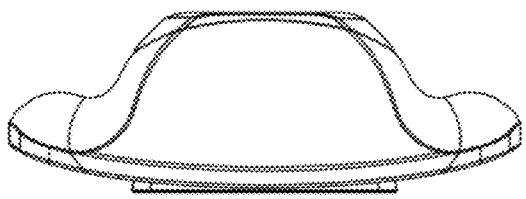
Figure 8D:
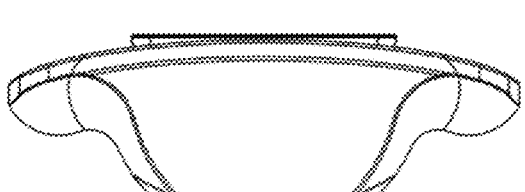
Figure 8E:
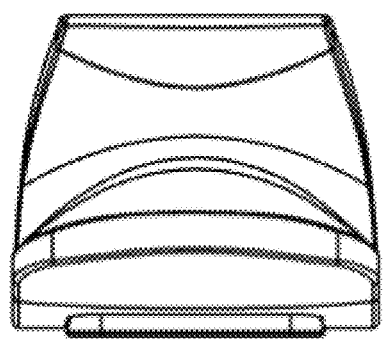
Figure 8F:
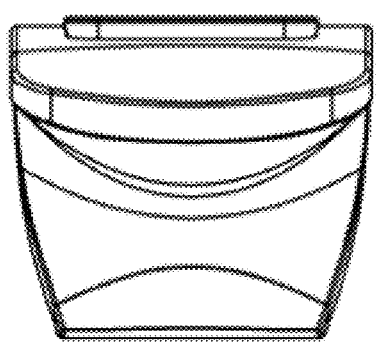
Figure 9A:
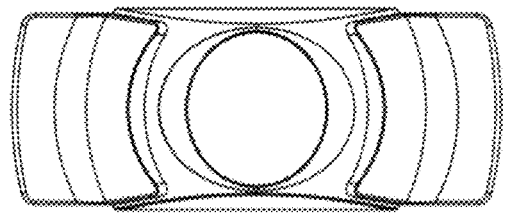
FIGS. 9A-9F are a series of illustrations of a second housing for a co-axial hyperspectral/multispectral camera, according to some embodiments.
Figure 9B:
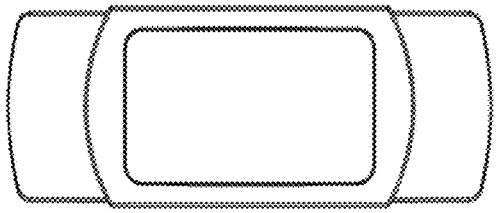
Figure 9C:
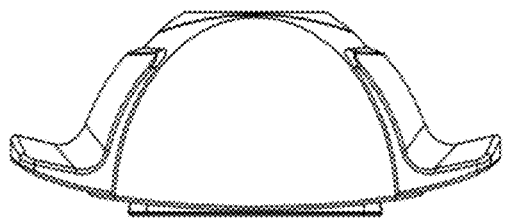
Figure 9D:
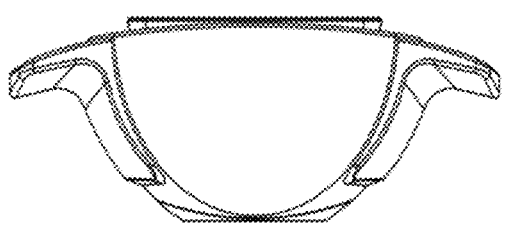
Figure 9E:
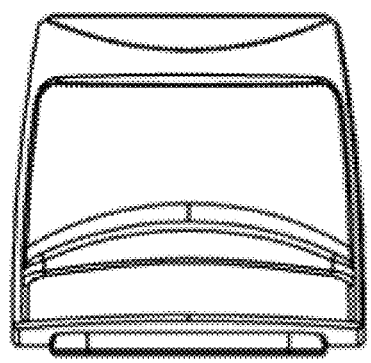
Figure 9F:
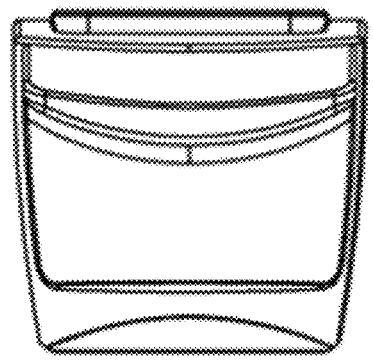
Figure 10A:
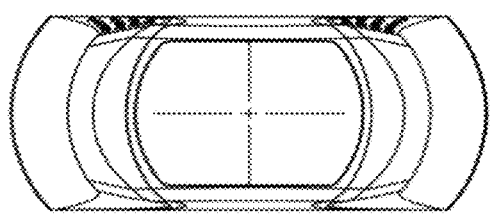
FIGS. 10A-10F are a series of illustration of a third housing for a co-axial hyperspectral/multispectral camera, according to some embodiments.
Figure 10B:
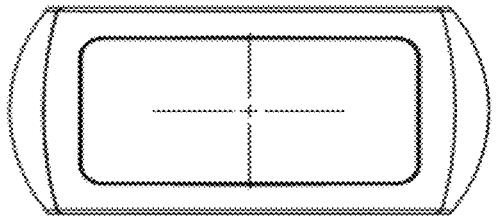
Figure 10C:
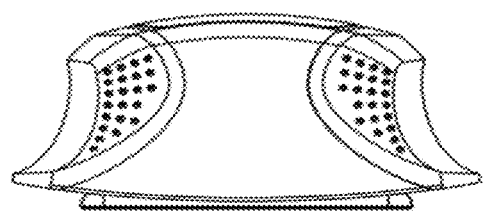
Figure 10D:
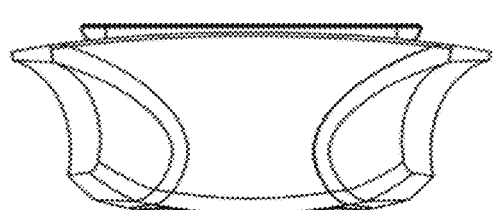
Figure 10E:
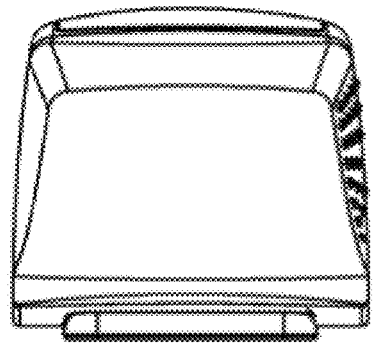
Figure 10F:
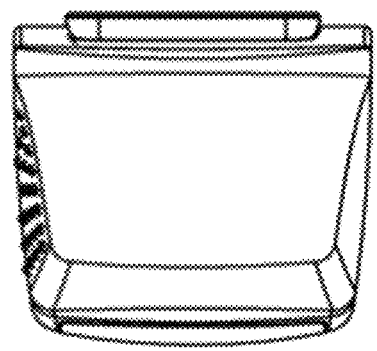
Figure 11A:
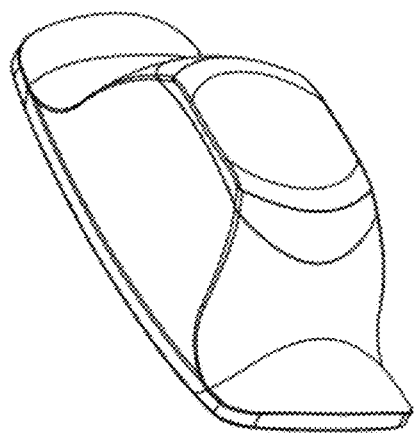
FIGS. 11A and 11B are perspective views of a first housing for a co-axial hyperspectral/multispectral camera, according to some embodiments.
Figure 11B:
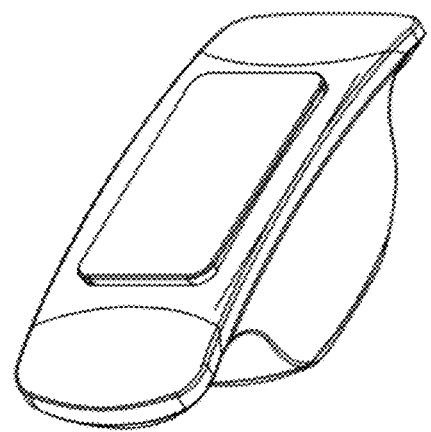
Figure 11C:
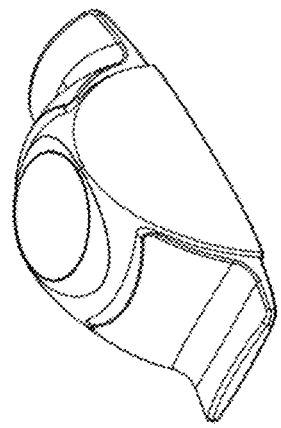
FIGS. 11C and 11D are perspective views of a second housing for a co-axial hyperspectral/multispectral camera, according to some embodiments.
Figure 11D:
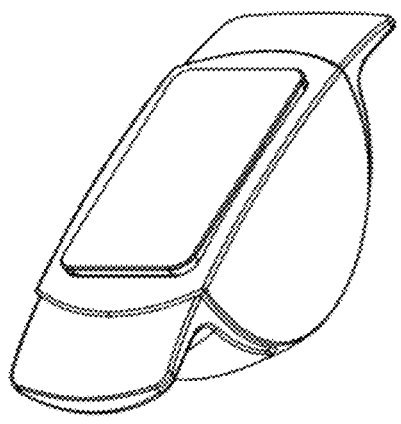
Figure 11E:
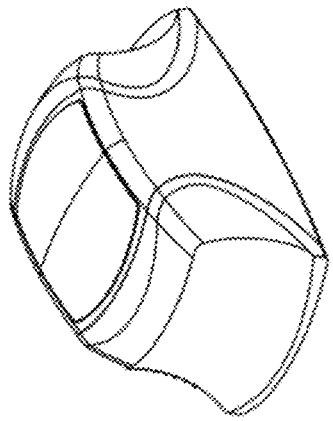
FIGS. 11E and 11F are perspective views of a third housing for a co-axial hyperspectral/multispectral camera, according to some embodiments.
Figure 11F:
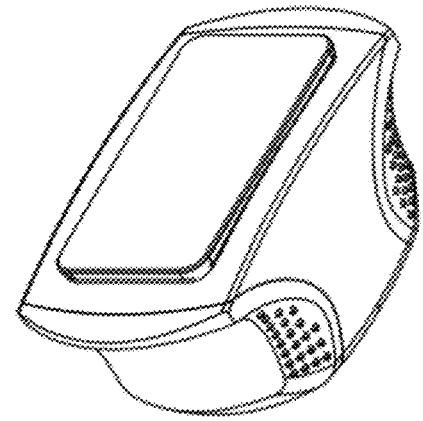

FIG. 7 shows an exploded view of the imager subsystem 210 of a co-axial hyperspectral/multispectral camera, according to some embodiments. The imager subsystem includes a plurality of optical detectors 206 mounted on a rigid flex printed circuit assembly 706 via rigid printed circuit board (PCB) islands 704 in electrical communication with a CPU (note shown), the CPU optionally mounted or otherwise in electrical communication with a motherboard (not shown), by means of a flex circuit or wire 208. The flex circuit-PCB island assembly is affixed onto a molded or machined fixture 700, optionally having individual slots 702 for mounting the respective PCB islands 704, to provide optical alignment with the various operating modes of the beam steering element 204, rigid mounting, and to provide vibration and shock resistance.

The optical detectors 206 are arranged at a fixed distance from the beam steering element 204 and thus the objective lens 106 or objective lens assembly 202. In certain embodiments, all of the optical detectors 206 in the imager subassembly 210 are arranged at the same fixed distance from the beam steering element 204. The distance between the optical detector 206 and objective lens 106 or objective lens assembly 202, together with the size of the sensor elements that make up the optical detector 206, determines (in part) the spectral resolution of the imager subsystem. The spectral resolution, which is the width (e.g., FWHM) of the component wavelengths collected by the optical detectors, is configured, e.g., by covering the optical detector 206 with an objective filter, so as to be sufficiently small to capture spectral features of medical conditions of interest.

The sensed intensity of component wavelengths depends on many factors, including the light source intensity, the sensor element sensitivity at each particular component wavelength, the reflectance or transmittance of different sensor components such as filters, polarizers, and lenses, and the exposure time of the sensor element to the component wavelength. These factors are selected such that the imager subsystem 210 is capable of sufficiently determining the intensity of component wavelengths that can distinguish the spectral features of medical conditions of interest.

1. Detector Wavelength Filters

In certain embodiments, wavelength filters are placed over the plurality of optical detectors to increase the percentage of a desired wavelength or spectral band of light reaching the optical detector. The detector filter is matched to a corresponding illumination filter, to increase the signal-to-noise ratio of an image captured at the desired wavelength. In certain embodiments, the detector filter is selected from a bandpass filter, a longpass filter, and a shortpass filter.

In specific embodiments, the illumination wavelength filter is a bandpass filter, e.g., a filter that allows only radiation having a wavelength in a certain range to pass, while blocking passage of other wavelengths. In certain embodiments, the FWHM spectral bandpass of an illumination filter (e.g., the size of the passband transmitted through the filter) is no more than about 100 nm, preferably no more than about 50 nm, more preferably no more than about 25 nm. In yet other embodiments, the FWHM spectral bandwidth of the filter is no more than 250 nm, 200 nm, 200 nm, 175 nm, 150 nm, 150 nm, 125 nm, 100 nm, 90 nm, 80 nm, 75 nm, 70 nm, 65 nm, 60 nm, 55 nm, 50 nm, 45 nm, 40 nm, 35 nm, 30 nm, 25 nm, 20 nm, 15 nm, 10 nm, 9 nm, 8 nm, 7 nm, 6 nm, 5 nm, 4 nm, 3 nm, 2 nm, or 1 nm.

In certain embodiments, the bandpass filter is a narrow pass filter. In specific embodiments, the narrow pass filter has a FWHM spectral bandwidth of no more than 25 nm, 24 nm, 23 nm, 22 nm, 21 nm, 20 nm, 19 nm, 18 nm, 17 nm, 16 nm, 15 nm, 14 nm, 13 nm, 12 nm, 11 nm, 10 nm, 9 nm, 8 nm, 7 nm, 6 nm, 5 nm, 4 nm, 3 nm, 2 nm, or 1 nm.

In some embodiments, the plurality of bandpass illumination filters have central wavelengths that are separated by at least 10 nm, or at least 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, or more.

2. Detector Polarizing Filters

In certain embodiments, polarizing lenses (polarizers) are placed over one or more of the plurality of optical detectors 206 to de-polarize light backscattered from a tissue of a patient. In some embodiments, a detector polarizing lens is matched to a corresponding illumination polarizing lens, to increase the signal-to-noise ratio of an image captured at the desired wavelength. In certain embodiments, the detector polarizing lens is selected from a linear polarizer, a circular polarizer, and an elliptical polarizer.

3. Optical Detectors

The optical detector may consist of one pixel or a multiplicity of pixels such as a mega pixel array sensor. Suitable optical detectors are well known in the art, and include without limitation, a charge-coupled device (CCD), a complementary metal-oxide-semiconductor (CMOS), a focal plane array, and a photo-cell. Focal plane arrays and photo-cells are particularly well suited for a line scanning device, in which the image of the ROI is scanned to one or more detectors simultaneously in rows and columns to create an image pixel-by-pixel.

Examples of CCD in accordance with the present disclosure include, but are not limited to a Si CCD, InGaAs, and HgCdTe detectors. A suitable spectral range in some embodiments is 0.3 microns to 1 micron, 0.4 micron to 1 micron, 1 micron to 1.7 microns, or 1.3 microns to 2.5 microns. In some embodiments the detector contains between 320 and 1600 spatial pixels. In other embodiments, the CCD has more or less spatial pixels. In some embodiments, the detector has a field of view between 14 degrees and 18.4 degrees. In some embodiments the CCD samples at a rate of between 3 nm and 10 nm.

In typical embodiments, the optical detectors are covered by detector filters, typically pass-band filters, configured for a wavelength of interest. Optionally, one or more optical detectors mounted in the imaging system is not be covered by a filter and can be used to acquire a broadband image of the subject, used to focus an image of the subject, and/or used to zoom in or out on a ROI.

4. Optimization of Exposure Time

Many advantages of the hyperspectral/multispectral imaging systems and methods described herein are derived, at least in part, from the use of in-band illumination and detection across multiple wavelengths/spectral band in co-axial alignment. For example, in-band illumination allows for greater signal-to-noise ratio and reduced exposure times, which in turn results in lower power consumption, reduced misalignment due to movement of the subject, and reduced computational burden when processing the resulting hyperspectral/multispectral data cubes.

These advantages can be further enhanced by minimizing the exposure time (e.g., shutter speed) needed to provide a suitable signal-to-noise ratio at each wavelength imaged. The minimum exposure time needed to resolve a suitable image at each wavelength will depend upon, at least, the sensitivity of the optical detector for the particular wavelength, the characteristics and intensity of ambient light present when acquiring images, and the concentration of melanin in the skin/tissue being imaged.

In one embodiment, the hyperspectral/multispectral imaging systems described herein advantageously reduces the total amount of time required to collect a complete hyperspectral/multispectral imaging by determining the specific exposure time needed to resolve each sub-image of the hyperspectral/multispectral image. Each of the sub-images is collected at a different wavelength or wavelength band and, because of this, the amount of time needed to resolve each sub-image will vary as a function of wavelength. In some embodiments, this variance is advantageously taken into account so that sub-images that require less time, because of their acquisition wavelengths or wavelength bands, are allotted shorter exposure times whereas sub-images that require more time because of their acquisition wavelengths or wavelength bands, are allotted shorter exposure times. This novel improvement affords a faster overall exposure time because each of the sub-images in the hyperspectral/multispectral image is only allocated an amount of time needed for full exposure, rather than a "one size fits all" exposure time. In a specific embodiment, non-transitory instructions encoded by the imager in non-transient memory determine the minimal exposure time required for image acquisition at each wavelength or each wavelength band used by the hyperspectral/multispectral imaging system.

In the hyperspectral/multispectral systems and methods described herein, the exposure time used for image acquisition is the time period in which an optical detector 206 is actively resolving light received from the beam steering element 204. Accordingly, exposure time can be manipulated by controlling the amount of time the beam steering element is in optical communication with the particular optical detector, controlling the time an optical detector 206 is actively resolving light, or a combination thereof.

One aspect provides a non-transitory computer readable storage medium storing one or more programs executable by a hyperspectral/multispectral imaging device with a central processing unit configured to execute the one or more programs and an optical acquisition subsystem configured to acquire a hyperspectral/multispectral image of a tissue of a subject. The hyperspectral/multispectral imaging device comprises a housing having an exterior and an interior and at least one light source attached to the housing (e.g., disposed on the exterior of the housing. The hyperspectral/multispectral imaging device further comprises at least one objective lens attached to or within the housing, the at least one objective lens disposed in an optical communication path, the optical communication path comprising an originating end and a terminating end. Light from the at least one light source is (i) first backscattered by a tissue of a subject and (ii) then passed from the originating end of the optical communication path, through the at least one objective lens, and to the terminating end of the optical communication path. The hyperspectral/multispectral imaging device further comprises a beam steering element within the interior of the housing, the beam steering element in optical communication with the terminating end of the optical communication path, the beam steering element characterized by a plurality of operating modes. The hyperspectral/multispectral imaging device further comprises a plurality of optical detectors offset from the optical communication path, each respective optical detector in the plurality of optical detectors in optical communication with a corresponding operating mode of the beam steering element. The hyperspectral/multispectral imaging device further comprises a plurality of detector filters within the housing, each respective detector filter in the plurality of detector filters covering a corresponding optical detector in the plurality of optical detectors thereby filtering light received by the corresponding optical detector from the beam steering element so that each optical detector in the plurality of optical detectors is configured for recording a respective sub-image in the plurality of sub-images at the wavelength or wavelength band of the respective sub-image. The one or more programs comprising instructions for identifying a plurality of baseline exposure times, each respective baseline exposure time in the plurality of baseline exposure times representing an exposure time for resolving a respective sub-image, in the plurality of sub-images, of the tissue of the subject at the wavelength or wavelength band of the respective sub-image. A first baseline exposure time for a first sub-image is different than a second baseline exposure time of a second sub-image in the plurality of sub-images. The one or more programs further comprise instructions for cycling the beam steering element through the plurality of operating modes, where the beam steering element is retained in each respective operating mode for the baseline exposure time corresponding to the wavelength or wavelength band collected by the optical filter corresponding to the respective operating mode so that a sub-image is recorded on the optical detector corresponding to the respective operating mode, thereby collecting the hyperspectral/multi spectral image of the tissue.

Figure 17:
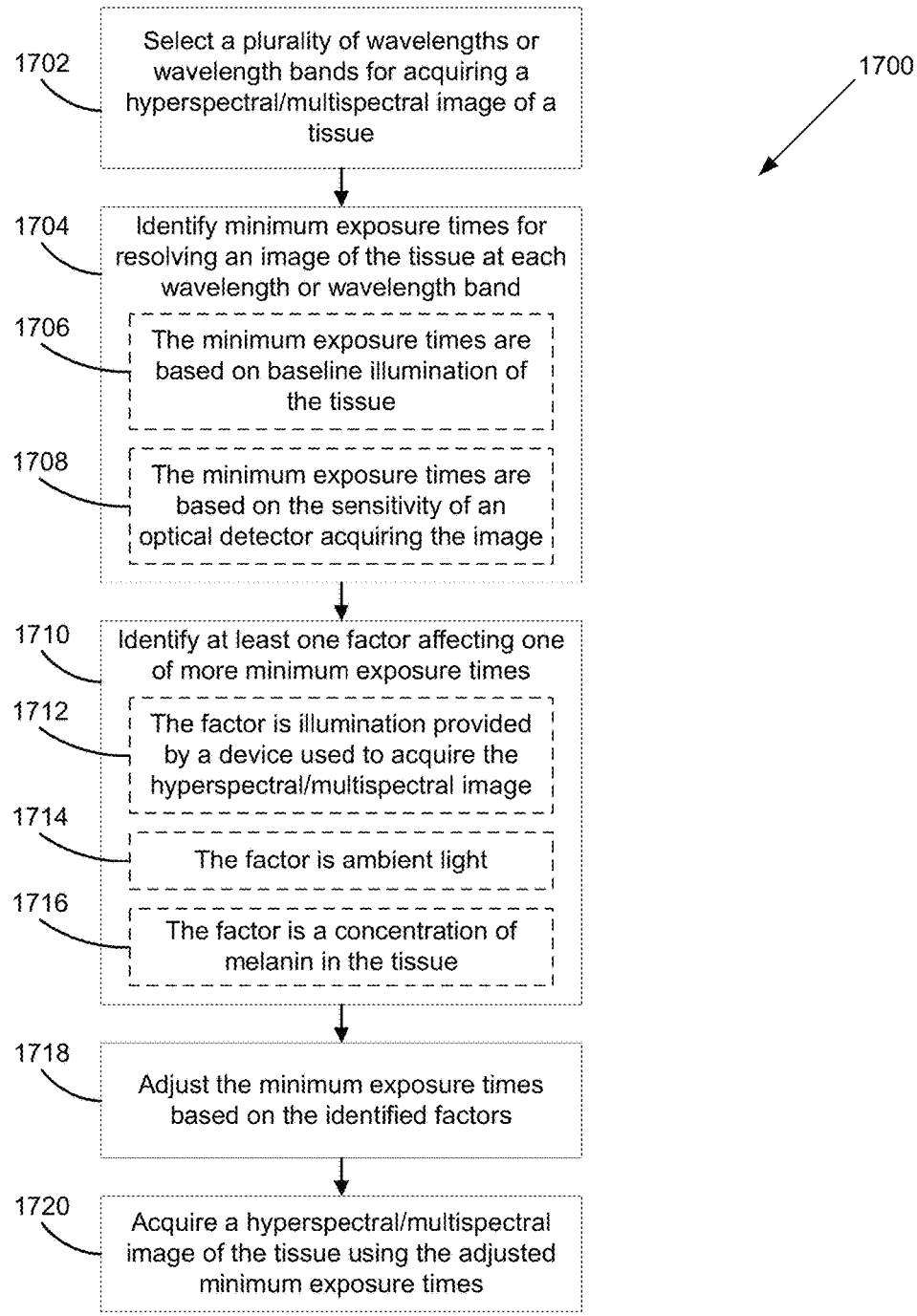
FIG. 17 is a schematic illustration of instructions for optimizing exposure times and collecting a hyperspectral/multispectral image, according to some embodiments.

Referring to FIG. 17, in one embodiment, a method (1700) is provided for acquiring a hyperspectral/multispectral image of a tissue of a patient, the method comprising selecting (1702) a plurality of wavelengths or discrete wavelength bands for acquiring a hyperspectral/multispectral image of a tissue; identifying (1704) minimum exposure times for resolving an image of the tissue at each wavelength or discrete wavelength band; identifying (1710) at least one factor affecting one of more minimum exposure times; adjusting (1718) the minimum exposure times based on the identified factors; and acquiring a hyperspectral/multispectral image of the tissue using the adjusted minimum exposure times.

In some embodiments, the minimum exposure times are based on baseline illumination of the tissue and/or the sensitivity of an optical detector acquiring the image.

In some embodiments, the factor affecting the minimal exposure time is one or more of illumination provided by a device used to acquire the hyperspectral/multispectral image, ambient light, and concentration of melanin in the tissue.

E. Processor Subsystem

FIG. 13 schematically illustrates an exemplary embodiment of the processor subsystem 1300. The processor subsystem 1300 includes one or more central processing units (CPU) 1308, an optional main non-volatile storage unit 1340, for example a memory card, for storing software and data, the storage unit 1340 optionally controlled by storage controller 1342, and a system memory 1314 for storing system control programs, data, and application programs, including programs and data loaded from the non-volatile storage unit 1340. The processor subsystem 1300 optionally includes a user interface 1302 including one or more input devices 1306 (e.g., a touch screen, buttons, or switches) and/or a display 1304, although in certain embodiments, the hyperspectral/multispectral imaging system may be controlled by an external device such as a handheld device, laptop computer, or desktop computer. The processor subsystem 1300 includes one or more communication interfaces 1312 for connecting to any wired or wireless external device (e.g., a handheld device, laptop computer, or desktop computer) or communication network (e.g., a wide area network such as the Internet) 1313. The processor subsystem 1300 includes a power source 1307 to power the aforementioned elements and an internal bus 1310 for interconnecting the aforementioned elements of the system. The communication bus 1310 may include circuitry (sometimes called a chipset) that interconnects and controls communications between system components.

In some embodiments, the processor subsystem 1300 communicates with a communication network 1313, thereby enabling the processor subsystem 1300 to transmit and/or receive data between mobile communication devices over the communication network, particularly one involving a wireless link, such as cellular, WiFi, ZigBee, BluTooth, IEEE 802.11b, 802.11a, 802.11g, or 802.11n, etc. The communication network can be any suitable communication network configured to support data transmissions. Suitable communication networks include, but are not limited to, cellular networks, wide area networks (WANs), local area networks (LANs), the Internet, IEEE 802.11b, 802.11a, 802.11g, or 802.11n wireless networks, landline, cable line, fiber-optic line, etc. The imaging system, depending on an embodiment or desired functionality, can work completely offline by virtue of its own computing power, on a network by sending raw or partially processed data, or both simultaneously.

Memory 1314 includes high-speed random access memory, such as DRAM, SRAM, DDR RAM, or other random access solid state memory devices; and typically includes non-volatile memory flash memory devices, or other non-transitory solid state storage devices. Memory 1314 optionally includes one or more storage devices remotely located from the CPU(s) 1308. Memory 1314, or alternately the non-transitory memory device(s) within memory 1314, comprises a non-transitory computer readable storage medium.

In some embodiments, operation of the processor subsystem 1300 is controlled primarily by an operating system 1320, which is executed by a central processing unit 1308. The operating system 1320 can be stored in a system memory 1314. In some embodiments, processor subsystem 1300 is not controlled by an operating system.

In some embodiments, the system memory 1314 includes one or more of a file system 1322 for controlling access to the various files and data structures described herein, an illumination software control module 1324 for controlling the light source(s) described herein, a beam steering software control module 1326 for controlling the operating modes of the beam steering element, an optical detector software control module 1328 for controlling the optical detectors and reading digital images acquired thereby, a digital image data store 1331 for storing digital images 1332 acquire by the optical detectors, a data processing software module 1334 for manipulating an acquired image or set of images, a hyperspectral/multispectral data cube data store 1335 for storing hyperspectral/multispectral data cubes 1336 assembled from a plurality of hyperspectral/multispectral data planes, and a communication interface software control module 1338 for controlling the communication interface 1312 that connects to an external device (e.g., a handheld device, laptop computer, or desktop computer) and/or communication network (e.g., a wide area network such as the Internet.

The acquired digital images 1332 and hyperspectral/multispectral data cubes 1336 can be stored in a storage module in the system memory 1314, and do not need to be concurrently present, depending on which stages of the analysis the processor subsystem 1300 has performed. In fact, in some embodiments, prior to imaging a subject and after communicating acquired digital images or processed data files thereof, the hyperspectral/multispectral imaging system contains neither acquired digital images 1332 nor hyperspectral data cubes 1336. In other embodiments, after imaging a subject and after communicating acquired digital images or processed data files thereof, the hyperspectral/multispectral imaging system retains acquired digital images 1332 and/or hyperspectral data cubes 1336 for a period of time (e.g., until storage space is needed, for a predetermined amount of time, etc.).

In some embodiments, the programs or software modules identified above correspond to sets of instructions for performing a function described above. The sets of instructions can be executed by one or more processors, e.g., a CPU(s) 1308. The above identified software modules or programs (e.g., sets of instructions) need not be implemented as separate software programs, procedures, or modules, and thus various subsets of these programs or modules may be combined or otherwise re-arranged in various embodiments. In some embodiments, a memory 1314 stores a subset of the modules and data structures identified above. Furthermore, a memory 1314 may store additional modules and data structures not described above.

The system memory 1314 optionally also includes one or more of the following software modules, which are not illustrated in FIG. 13: a spectral library which includes profiles for a plurality of medical conditions, a spectral analyzer software module to compare measured hyperspectral/multispectral data to a spectral library, control modules for additional sensors; information acquired by one or more additional sensors, an image constructor software module for generating a hyperspectral/multispectral image, a hyperspectral/multispectral image assembled based on a hyperspectral/multispectral data cube and optionally fused with information acquired by an additional sensor, a fusion software control module for integrating data acquired by an additional sensor into a hyperspectral/multispectral data cube, and a display software control module for controlling a built-in display.

While examining a subject and/or viewing hyperspectral/multispectral images of the subject, a physician can optionally provide input to processor subsystem 1300 that modifies one or more parameters upon which a hyperspectral/multispectral image and/or diagnostic output is based. In some embodiments, this input is provided using input device 1306. Among other things, the processor subsystem 1300 can be instructed to modify the spectral portion selected by a spectral analyzer (e.g., to modify a threshold of analytical sensitivity) or to modify the appearance of the image generated by an image constructor (e.g., to switch from an intensity map to a topological rendering).

Likewise, the processor subsystem 1300 can be instructed to communicate instructions to the imager subsystem 210 to modify the sensing properties of one of the optical detectors (e.g., an exposure setting, a frame rate, an integration rate, or a wavelength to be detected). Other parameters can also be modified. For example, the processor subsystem 1300 can be instructed to obtain a wide-view image of the subject for screening purposes, or to obtain a close-in image of a particular region of interest.

In some embodiments, processor subsystem 1300 does not include a controller 1342 or memory 1340. In some such embodiments, memory 1314 and CPU 1308 are, in fact, one or more application-specific integrated circuit chips (ASICs). For example, in some embodiments, an ASIC includes the instructions of illumination control module 1324, beam steering control module 1326, optical detector control module 1328, data processing module 1334 and/or communication interface control module 1338. In some embodiments, the ASIC further includes storage space for the acquired digital image data store 1331 and the digital images 1332 stored therein and/or the hyperspectral/multispectral data cube data store 1335 and the hyperspectral/multispectral data cubes 1336 stored therein.

1. Spectral Analyzer

In some embodiments, memory 1314 include a spectral library and spectral analyzer for comparing hyperspectral/multispectral data acquired by the imaging system to known spectral patterns associated with various medical conditions. In other embodiments, analysis of the acquired hyperspectral/multispectral data is performed on an external device such as a handheld device, tablet computer, laptop computer, desktop computer, an external server, for example in a cloud computing environment.

In some embodiments, a spectral library includes profiles for a plurality of medical conditions, each of which contain a set of spectral characteristics unique to the medical condition. A spectral analyzer uses the spectral characteristics to determine the probability or likelihood that a region of the subject corresponding to a measured hyperspectral/multispectral data cube is inflicted with the medical condition. In some embodiments, each profile includes additional information about the condition, e.g., information about whether the condition is malignant or benign, options for treatment, etc. In some embodiments, each profile includes biological information, e.g., information that is used to modify the detection conditions for subjects of different skin types. In some embodiments, the spectral library is stored in a single database. In other embodiments, such data is instead stored in a plurality of databases that may or may not all be hosted by the same computer, e.g., on two or more computers addressable by wide area network. In some embodiments, the spectral library is electronically stored in a non-volatile storage unit 1340 and recalled using a storage controller 1342 when needed.

In some embodiments, a spectral analyzer analyzes a particular spectra derived from a hyperspectral/multispectral data cube, the spectra having pre-defined spectral ranges (e.g., spectral ranges specific for a particular medical condition), by comparing the spectral characteristics of a predetermined medical condition to the subject's spectra within the defined spectral ranges. Performing such a comparison only within defined spectral ranges can both improve the accuracy of the characterization and reduce the computational power needed to perform such a characterization.

The spectral characteristics of a medical condition, such as ischemia or an ulcer, can be determined, for example, by first identifying an actual condition of that type on another subject, for example using conventional visual examination, and then obtaining the wavelength-dependent backscattering $R_{MC}(\lambda)$ of a representative region of the skin affected by the medical condition. The backscattering of the affected skin $R_{MC}(\lambda)$ can then be spectrally compared to the wavelength-dependent backscattering of that subject's normal skin in the same area of the lesion, $R_{NS}(\lambda)$, by normalizing the backscattering of the affected skin against the backscattering of normal skin as follows:

$$R_{MC,N}(\lambda)=R_{MC}(\lambda)/R_{NS}(\lambda),$$

where $R_{MC,N}(\lambda)$ is the normalized backscattering of the affected skin. In other embodiments, $R_{MC,N}(\lambda)$ is instead determined by taking the difference between $R_{MC}(\lambda)$ and $R_{NS}(\lambda)$, or by calculating $R_{MC,N}(\lambda)=[R_{MC}(\lambda)-R_{NS}(\lambda)]/[R_{MC}(\lambda)+R_{NS}(\lambda)]$. Other types of normalization are possible. Note that if there are multiple representative regions of affected skin, there will be as many normalized backscatterings of the affected skin. These normalized backscatterings can be averaged together, thus accounting for the natural spectral variation among different regions of the affected skin. Note also that because of the natural variation in characteristics of normal skin among individuals, as well the potential variation in characteristics of a particular type of affected skin among individuals, it can be useful to base the model of the normalized affected skin backscattering $R_{MC,N}(\lambda)$ on the average of the backscatterings $R_{MC}(\lambda)$ of many different affected skin samples of the same type, as well as on the average of the backscatterings $R_{NS}(\lambda)$ of many different types of normal skin (e.g., by obtaining $R_{MC,N}(\lambda)$ for many different subjects having that medical condition, and averaging the results across the different subjects).

In one embodiment, in order to determine whether the subject has the type of medical condition characterized by $R_{MC,N}(\lambda)$, the spectral analyzer obtains the skin reflectance of each region, $R_{region}(\lambda)$, from a measured hyperspectral cube or data plane (1336). The spectral analyzer then normalizes the backscattering $R_{region}(\lambda)$ from that region against the wavelength-dependent backscattering of the subject's normal skin in the same area, $R_{NS,Subject}(\lambda)$, as follows:

$$R_{region,N}(\lambda)=R_{region}(\lambda)/R_{NS,Subject}(\lambda),$$

where $R_{region}(\lambda)$ is the normalized backscattering of the region. Other types of normalization are possible.

In some embodiments, the spectral analyzer analyzes the subjects' spectra by comparing $R_{region,N}(\lambda)$ to $R_{MC,N}(\lambda)$. In one simple example, the comparison is done by taking the ratio $R_{region,N}(\lambda)/R_{MC,N}(\lambda)$, or the difference $R_{MC,N}(\lambda)-R_{region,N}(\lambda)$. The magnitude of the ratio or difference indicates whether any region has spectral characteristics that match that of affected skin. However, while ratios and differences are simple calculations, the result of such a calculation is complex and requires further analysis before a diagnosis can be made. Specifically, the ratio or subtraction of two spectra, each of which has many peaks, generates a calculated spectrum that also has many peaks. Some peaks in the calculated spectrum may be particularly strong (e.g., if the subject has the medical condition characterized by $R_{MC,N}(\lambda)$), but other peaks may also be present (e.g., due to noise, or due to some particular characteristic of the subject). A physician in the examination room would typically find significantly more utility in a simple "yes/no" answer as to whether the subject has a medical condition, than he would in a complex spectrum. One method of obtaining a "yes/no" answer is to calculate whether a peak in the calculated spectrum has a magnitude that is above or below a predetermined threshold and is present at a wavelength that would be expected for that medical condition.

Another way to obtain a "yes/no" answer is to treat $R_{region,N}(\lambda)$ and $R_{MC,N}(\lambda)$ as vectors, and to determine the "angle" between the vectors. The angle represents the degree of overlap between the vectors, and thus represents how likely it is that the subject has the medical condition. If the angle is smaller than a threshold value, the subject is deemed have the medical condition; if the angle does not exceed a threshold value, the subject is deemed not to have the medical condition. Alternately, based on the value of the angle between the vectors, a probability that the subject has the medical condition can be determined.

In one embodiment, a spectral library may comprise a personalized database of spectral information that is collected for a particular subject. The personalized database can then be used to monitor changes in the subject over time. Changes over time in the spectral characteristics of a region on the subject can be used to provide information, for example, on the progression or regression of a medical condition, the efficacy of treatment, and the appearance of a new medical condition (e.g., the formation of an ulcer). The provided information can be used to inform the medical treatment of the subject. For further details, see U.S. Patent Publication No. 2009/0326383, the content of which is hereby incorporated herein by reference in its entirety for all purposes.

In certain embodiments, the spectral analyzer includes a trained data analysis algorithm for identifying a region on the subject's skin of biological interest using an image obtained by the apparatus and/or for determining a portion of a hyperspectral/multispectral data cube that contains information about a biological insult in the subject's skin. A wide variety of pattern classification techniques and/or statistical techniques can be used in accordance with the present disclosure to help in the analysis. For instance, such pattern classification techniques and/or statistical techniques can be used to (i) assist in identifying a medical condition of a subject, (ii) assist in characterizing a medical condition of a subject, and (iii) assist in analyzing the progression of a medical condition of a subject (e.g., detect changes in tissue composition or a wound on the skin of a patient over time). For further details, see U.S. Patent Publication No. 2009/0326383, the content of which is hereby incorporated herein by reference in its entirety for all purposes.

Pattern classification is used to mine a spectral library to identify and characterize medical conditions (e.g., ischemia, an ulcer, diabetes, etc.) that are characterized by observable hyperspectral/multispectral signatures. In some examples, the hyperspectral/multispectral signatures are values of specific pixels in an image of a subject's skin, patterns of values of specific groups of pixels in an image of a subject's skin, values of specific measured wavelengths or any other form of observable data that is directly present in the spectral data and/or that can be derived from the spectral data taken of a subject's skin. In some embodiments, pattern classification techniques such as artificial intelligence are used to analyze hyperspectral/multispectral data cubes, the output of other sensors or cameras, and/or hyperspectral/multispectral images themselves (which may or may not be fused with other information), further details, see: U.S. Patent Publication No. 2009/0326383; National Research Council; Panel on Discriminant Analysis Classification and Clustering, Discriminant Analysis and Clustering, Washington, D.C.: National Academy Press; and Dudoit et al., JASA 97; 77-87 (2002), the contents of which are hereby incorporated herein by reference in their entireties, for all purposes.

Relevant algorithms for decision rules include, but are not limited to: discriminant analysis including linear, logistic, and more flexible discrimination techniques (see, e.g., Gnanadesikan, 1977. *Methods for Statistical Data Analysis of Multivariate Observations*, New York: Wiley 1977; tree-based algorithms such as classification and regression trees (CART) and variants (see, e.g., Breiman, 1984, *Classification and Regression Trees*, Belmont, Calif.: Wadsworth International Group); generalized additive models (see, e.g., Tibshirani, 1990, *Generalized Additive Models*, London: Chapman and Hall); neural networks (see, e.g., Neal, 1996, *Bayesian Learning for Neural Networks*, New York: Springer-Verlag; and Insua, 1998, Feedforward neural networks for nonparametric regression In: *Practical Nonparametric and Semiparametric Bayesian Statistics*, pp. 181-194, New York: Springer), the contents of which are hereby incorporated herein by reference in their entireties, for all purposes. Other suitable data analysis algorithms for decision rules include, but are not limited to, logistic regression, or a nonparametric algorithm that detects differences in the distribution of feature values (e.g., a Wilcoxon Signed Rank Test (unadjusted and adjusted)).

Additional suitable data analysis algorithms are known in the art, some of which are reviewed in Hastie et al., (2001, The Elements of Statistical Learning, Springer-Verlag, New York, Chapter 9, the content of which is hereby incorporated herein by reference in its entirety for all purposes). Examples of data analysis algorithms include, but are not limited to: Classification and Regression Tree (CART), Multiple Additive Regression Tree (MART), Prediction Analysis for Microarrays (PAM), and Random Forest analysis. Such algorithms classify complex spectra and/or other information in order to distinguish subjects as normal or as having a particular medical condition. Other examples of data analysis algorithms include, but are not limited to, ANOVA and nonparametric equivalents, linear discriminant analysis, logistic regression analysis, nearest neighbor classifier analysis, neural networks, principal component analysis, quadratic discriminant analysis, regression classifiers and support vector machines. Such algorithms may be used to construct a decision rule and/or increase the speed and efficiency of the application of the decision rule and to avoid investigator bias, one of ordinary skill in the art will realize that computer-based algorithms are not required to carry out the disclosed methods.

In specific embodiments, suitable data analysis algorithms operable by the central processing unit(s) 1308 of the hyperspectral/multispectral imaging systems described herein, or by external devices or servers, are used, for example, to detect the location and/or severity of diabetic foot ulcers or pressure ulcers. In some embodiments, suitable data analysis algorithms are used to predict the possible formation of diabetic foot ulcers or pressure ulcers. Non-limiting examples of suitable data analysis algorithms for these purposes are found in Yudovsky D. et al., J Diabetes Sci Technol. (2010) Sep. 1; 4(5):1099-113; Yudovsky D. et al., J Biomed Opt. (2011) February; 16(2):026009, and Yudovsky D. et al., J Biophotonics (2011) August; 4(7-8): 565-76, the contents of which are hereby incorporated herein by reference in their entireties for all purposes.

For additional information on the use of trained data analysis algorithms for the analysis of hyperspectral/multispectral data, see, for example, U.S. Patent Publication Nos. 2009/0326383 and 2003/0215791, and U.S. Pat. Nos. 7,282,723 and 7,219,086, the contents of which are hereby incorporated herein by reference in their entireties for all purposes.

F. Display Subsystem

In certain embodiments, the hyperspectral/multispectral imaging system comprises a display 1304 which receives an image (e.g., a color image, mono-wavelength image, or hyperspectral/multispectral image) from a display control module, and displays the image. Optionally, the display subsystem also displays a legend that contains additional information. For example, the legend can display information indicating the probability that a region has a particular medical condition, a category of the condition, a probable age of the condition, the boundary of the condition, information about treatment of the condition, information indicating possible new areas of interest for examination, and/or information indicating possible new information that could be useful to obtain a diagnosis, e.g., another test or another spectral area that could be analyzed.

In one embodiment, a housing display is built into the housing of a hyperspectral/multispectral imaging system. In an example of such an embodiment, a video display in electronic communication with the processor 1308 is mounted on the back-side of a co-axial camera, as described herein. In a particular embodiment, the housing display is a touchscreen display that is used to manipulate the displayed image and/or control the hyperspectral/multi spectral system.

In another embodiment, the communication interface 1312 comprises a docking station for a mobile device having a mobile device display. A mobile device, such as a smart phone, a personal digital assistant (PDA), an enterprise digital assistant, a tablet computer, an IPOD, a digital camera, or a portable music player, can be connected to the docking station, effectively mounting the mobile device display onto the hyperspectral/multispectral imaging system (e.g., camera). Optionally, the mobile device is used to manipulate the displayed image and/or control the hyperspectral/multispectral system.

In yet another embodiment, the processor subsystem 1300 is configured to be in wired or wireless communication with an external display, for example, on a handheld device, tablet computer, laptop computer, desktop computer, television, IPOD, or projector unit, on which the image is displayed. Optionally, a user interface on the external device is used to manipulate the displayed image and/or control the hyperspectral/multispectral system.

In one embodiment, an image can be displayed in real time on the display. The real-time image can be used, for example, to focus an image of the subject, to select an appropriate region of interest, and to zoom the image of the subject in or out. In one embodiment, the real-time image of the subject is a color image captured by an optical detector that is not covered by a detector filter. In these embodiments, the imager subsystem comprises an optical detector dedicated to capturing true color images of a subject. In another embodiment, the real-time image of the subject is a mono-wavelength, or narrow-band (e.g., 10-50 nm), image captured by an optical detector covered by a detector filter. In these embodiments, any optical detector covered by a detector filter in the imager subsystem may be used for: (i) resolving digital images of the subject for integration into a hyperspectral/multi spectral data cube; and (ii) resolving narrow-band images for focusing, or otherwise manipulating the optical properties of the imaging system.

In some embodiments, a hyperspectral/multispectral image constructed from data collected by the imaging system is displayed on an internal housing display, mounted housing display, or external display. Assembled hyperspectral/multispectral data (e.g., present in a hyperspectral/multispectral data cube) is used to create a two-dimensional representation of the imaged object or subject, based on one or more parameters. An image constructor module, stored in the imaging system memory or in an external device, constructs an image based on, for example, an analyzed spectra. Specifically, the image constructor creates a representation of information within the spectra. In one example, the image constructor constructs a two-dimensional intensity map in which the spatially-varying intensity of one or more particular wavelengths (or wavelength ranges) within the spectra is represented by a corresponding spatially varying intensity of a visible marker.

In certain embodiments, the image constructor fuses a hyperspectral image with information obtained from one or more additional sensors. Non-limiting examples of suitable image fusion methods include: band overlay, high-pass filtering method, intensity hue-saturation, principle component analysis, and discrete wavelet transform. For further details on exemplary image fusion techniques, see U.S. Patent Publication No. 2009/0326383, the content of which is hereby incorporated herein by reference in its entirety for all purposes.

1. Touchscreen Displays

In one embodiment, the display subsystem includes a touchscreen video display that can be manipulated by the user, for example, to focus an image, zoom in or out within an image, select a region of an image for further analysis, change the contrast of the image, change a parameter of a hyperspectral/multispectral image (e.g., the mode, spectral bands represented, artificial coloring, etc.). In a specific embodiment, the display subsystem comprises a touchscreen overlaying a second video display, such as an LCD display, the touchscreen and second video display having their own circuitry and patterns.

Touchscreens use various technologies to sense touch from a finger or stylus, such as resistive, capacitive, infrared, and acoustic sensors. Resistive sensors rely on touch to cause two resistive elements overlaying the display to contact one another completing a resistive circuit, while capacitive sensors rely on the capacitance of a finger changing the capacitance detected by an array of elements overlaying the display device. Infrared and acoustic touchscreens similarly rely on a finger or stylus to interrupt infrared or acoustic waves across the screen, indicating the presence and position of a touch.

Capacitive and resistive touchscreens often use transparent conductors such as indium tin oxide (ITO) or transparent conductive polymers such as PEDOT to form an array over the display image, so that the display image can be seen through the conductive elements used to sense touch. The size, shape, and pattern of circuitry have an effect on the accuracy of the touchscreen, as well as on the visibility of the circuitry overlaying the display. Although a single layer of most suitable conductive elements is difficult to see when overlaying a display, multiple layers can be visible to a user, and some materials such as fine line metal elements are not transparent but rely on their small size to avoid being seen by users.

For additional information on the use of touchscreen displays, see, for example, U.S. Pat. Nos. 7,190,348, 7,663,607, and 7,843,516 and U.S. Patent Publication Nos. 2008/0062139, 2009/0046070, 2011/0102361, 2011/0095996, the contents of which are hereby incorporated herein by reference in their entireties for all purposes.

G. Additional Elements

In some embodiments, the hyperspectral/multispectral imaging system is mountable on a tripod or other fixed structure. In some embodiments, the tripod is a fixed sensor tripod or a fixed sensor tripod on wheels. In some embodiments, the hyperspectral sensor is mountable on a mobile or fixed rack. For example, in some embodiments, a mobile hyperspectral/multispectral imaging device may be mounted on a rack or other permanent fixture in an examination room.

III. Overview of Methods

Figure 14:
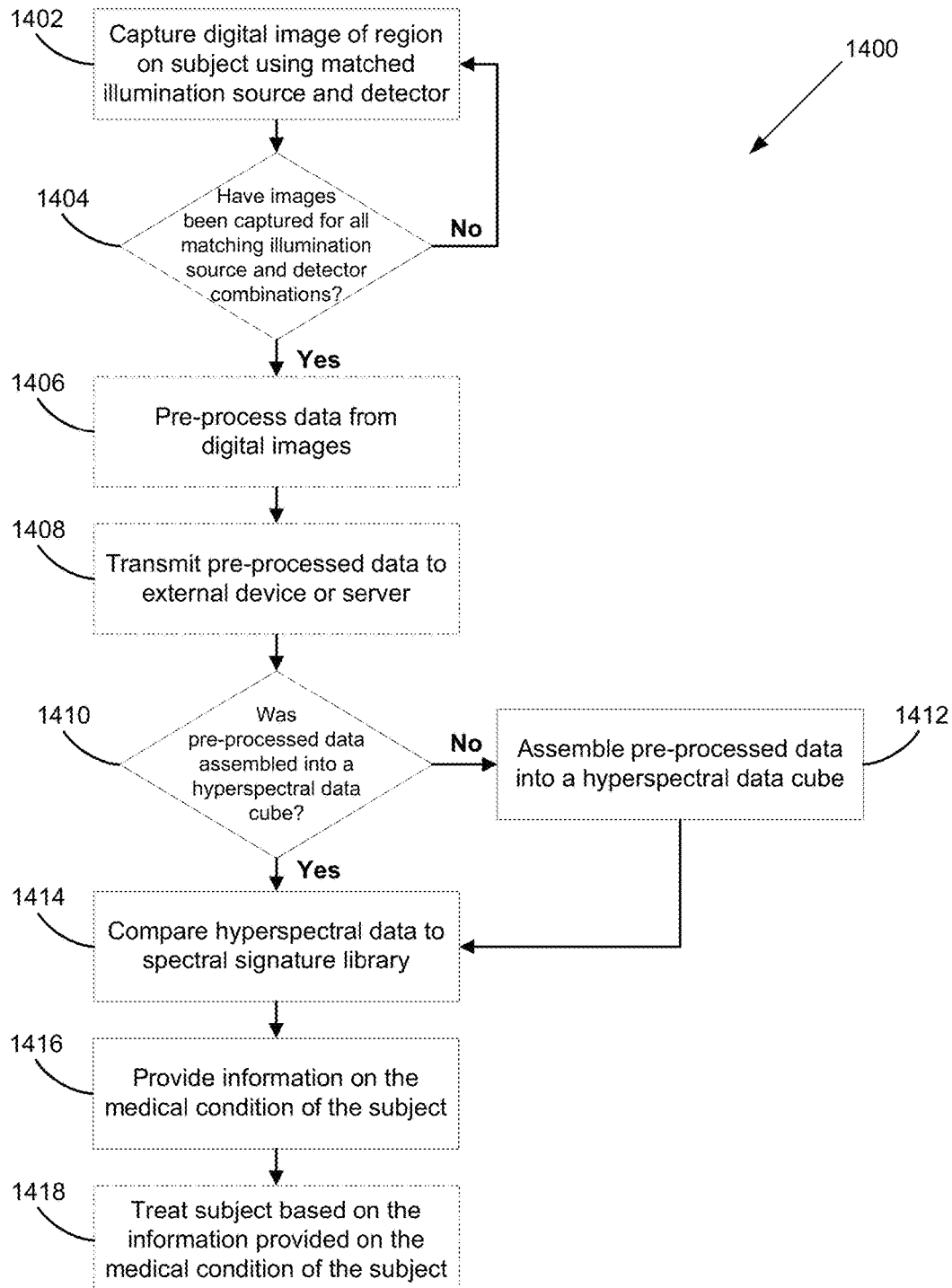
FIG. 14 illustrates a method for providing information regarding the medical condition of a subject and optionally treating the subject accordingly, according to some embodiments.

FIG. 14 illustrates an overview of a method (1400) for providing information on the medical condition of a subject, using hyperspectral/multispectral imaging. First, a digital image of an ROI on a subject is captured (1402) at a first wavelength using a first matching illumination source and optical detector included in a hyperspectral/multispectral imaging system as described herein. In some embodiments, the particular area of the subject comprises several different contiguous or non-contiguous regions of the subject's skin. As described in greater detail herein, in some embodiments, this image is obtained by illuminating an ROI with a first narrowband light source disposed on the imaging system and directing light backscattered from the ROI to a first optical detector configured to resolve the narrowband light (e.g., an optical detector covered by a filter matching the narrowband illumination source) using a beam steering element positioned in a first operating mode in optical communication with the first optical detector.

At step 1404, a determination is made as to whether images have been captured for all matching illumination source and detector combinations. If not 1404—No, an additional image of the ROI is captured (e.g., at a second wavelength using a second matching illumination source and optical detector). Additional digital images are collected at unique narrowband wavelengths in this manner until images of the ROI have been obtained at all desired wavelengths 1404—Yes. The quantity and identity of required images resolved at unique wavelengths depends upon the medical condition(s) being evaluated. In certain embodiments, for example, where an ischemic condition is being evaluated by measuring oxyhemoglobin and deoxyhemoglobin levels at an ROI, as little as three wavelengths are required for the analysis. In other embodiments, for example, where potentially cancerous skin legions are being discriminated from other pigmented legions, many more images may be required (see, Nagaoka T. et al., supra).

Optionally, data contained with the acquired digital images is then pre-processed (1406) by a central processing unit (CPU) present in the hyperspectral/multispectral imaging system. The digital images may be processed, for example, to adjust the brightness of the acquired digital image(s), adjust the contrast of the acquired digital image(s), remove an artifact from the acquired digital image(s), crop the acquired digital image(s), processing one or more sub-pixels of the acquired digital image(s), compress the size of the acquired digital image(s), assemble a plurality of acquired digital images into a spectral hypercube, transform a spectral hypercube assembled from the plurality of acquired digital images, format data contained within the acquired digital image(s), and/or encrypt data contained within the acquired digital image.

The processed data and/or raw unprocessed digital images are then transmitted to an external device or server in step 1408 for further analysis. Due to the extensive computational power required for the analysis of hyperspectral/multispectral data sets, it is desirable to perform as much of the computation on an external device or server, for example, to free up the CPU in the imaging system for image acquisition and/or to lower the computational requirements of the imaging system, especially in a handheld camera embodiment running on battery power. Non-limiting examples of external devices suitable for processing hyperspectral/multispectral data include: handheld devices such as smart phone, personal digital assistants (PDA), IPHONES, enterprise digital assistants, tablet computers, desktop computers, laptop computers, servers containing multiple CPUs, and cloud computing environments. In certain embodiments, processing and analysis is broken-up between multiple devices. For example, in one embodiment, a hyperspectral/multispectral imaging system transmits processed or unprocessed digital images to a handheld device (e.g., a smart phone). The smart phone may perform additional processing steps and/or initial analysis of the data and then transmit intermediate data files to a second device or server, for example, a cloud computing environment, to perform computationally taxing analysis.

In step 1410, the external device or server determines whether the data were transmitted in a format suitable for hyperspectral/multispectral analysis, e.g., a pre-assembled spectral data cube. If the data are not present in a suitable format 1410—No, the external device or server format the data accordingly in step 1412, for example, by assembling the data into a spectral data cube. Measurements from the plurality of digital images may be processed according to methods such as clustering analysis, principal component analysis or any analytic methods that are suitable for processing such measurements. In some embodiments, the measurements are normalized before any analytical processing is performed.

If the external device or server determines the data transmitted in a format suitable for hyperspectral/multispectral analysis (1410—Yes) or after upon appropriate formatting, 1412, the hyperspectral/multispectral data is compared, in step 1414, to one or more spectral signatures in a library of spectral signatures in which each spectral signature in the library corresponds to one or more spectral characteristics of a medical condition. In some embodiments, a medical condition is identified when the comparison results in identification of a spectral signature from the spectral signature library that most resembles a spectrum in the measured hyperspectral/multispectral data. Results from such a comparison can be represented by a similarity metric, such as a ratio or a similarity matrix.

Examples of similarity metrics are reviewed in McGill et al., 1979, "An evaluation of factors affecting document ranking by information retrieval systems," Project report, Syracuse University School of Information Studies, the content of which is hereby incorporated herein by reference in its entirety for all purposes. In particular, Table 2 of McGill et al list 67 different exemplary similarity metrics that can be used to compare measurements from one or more of the plurality of regions with a spectral signature in a library of spectral signatures. If the similarity metrics is above a certain value, the corresponding region will be identified as the suspect region. For example, a region can be identified as a suspect region when the similarity metric between the region and a spectral signature for a medical condition is, e.g., a ratio of 0.4 or above, 0.5 or above, 0.6 or above, 0.7 or above, 0.8 or above, 0.9 or above, where 1.0 represents complete identity between the region and the spectral signature of the medical condition. It will be understood by one of skill of the art that the threshold for the similarity metric can differ with respect to the type of tissues under analysis. For example, it may be more difficult obtaining signals for a certain type of tissues such that the signal to noise ratio for the particular tissue may be low; thus ultimately resulting in a low similarity metrics value. In some embodiments, measurements of a plurality of regions are resolved into spectra where each spectrum corresponds to a different region. The spectrum corresponding to a particular region is then compared to a signature spectrum corresponding to a medical condition. The signature spectrum is obtained by taking measurements of a region that is known to have the medical condition. It will be understood by one of skill in the art that any suitable analytical methods can be used for obtaining the spectral signature of the medical condition.

To compute a similarity metric (e.g., a correlation coefficient) between measurements from the ROI with one or more spectral signatures in a library of spectral signatures, any number of techniques can be used. For example, a plurality of features can be calculated from the measurements of a region in the plurality of regions. These same features can be calculated from the spectral signatures. One example of the feature is an observed or recorded intensity at a particular wavelength. Another example of a feature is the ratio of one observed or recorded intensity at one particular wavelength divided by another observed or recorded intensity at another particular wavelength. Another example of a feature is some mathematical function of two or more observed or recorded intensities at unique wavelengths. Exemplary mathematical functions include, but are not limited to, monomial and polynomial functions (e.g., binomial functions, quadratic functions, trinomial function, etc.) of any degree greater than zero (e.g., the linear function f(x)=a*(x)+b given above where the value $\lfloor a^*(x) \rfloor$ is taken for a*(x)), rational functions $$\left( e.g., R(x) = \frac{a_n x^n + a_{n-1} x^{n-1} + \ldots + a_1 x + a_o}{b_n x^n + b_{n-1} x^{n-1} + \ldots + b_1 x + b_o} \right),$$

exponential functions (e.g., exponential decay or exponential growth), power functions (e.g., $f(x) = ax^p$, where a and p are real numbers), power series (e.g., a power series on variable x), or any combination thereof. In this way, five or more, ten or more, twenty or more, or one hundred or more features can be calculated from each hyperspectral image. The values of these features can then be used as the basis for computing a similarity between such images.

In some embodiments, additional information collected from the ROI on the subject is used to assist in the identification of a medical condition. In certain embodiments, the additional data is integrated with the hyperspectral/multi-spectral data measured from the plurality of images acquired of the ROI and the integrated data is compared to a library of spectral signatures containing integrated spectral and non-spectral signatures. In other embodiments, the additional data is analyzed separately from the hyperspectral/multispectral data, for example compared to a separate library of like signatures, for further characterize or confirm a particular medical condition. Additional data can be collected using any combination of sensor, for example, a LIDAR sensor, a thermal imaging sensor, a millimeter-wave (microwave) sensor, a color sensor, an X-ray sensor, a UV sensor, a NIR sensor, a SWIR sensor, a MWIR sensor, and a LWIR sensor. In certain embodiments, the additional sensor is integrated into the hyperspectral/multispectral imaging system. In other embodiments, the additional data is collected using a separate device. Exemplary methods for collecting, integrating, and processing additional data in conjunction with hyperspectral/multispectral data are provided in U.S. Patent Application Publication No. 2009/0326383 to Barnes et al., the content of which is hereby incorporated herein by reference in its entirety for all purposes.

After a spectral signature associated with a medical condition is identified in the measured hyperspectral/multispectral data (1414), information on the medical condition is provided to a healthcare professional (1416). This information can be, for example, information that provides or aids in providing a diagnosis for the patient, information that provides a likelihood for a particular diagnosis, information that provides or aids in providing a prognosis for disease progression, information that provides or aids in providing a prognosis for a particular treatment course, information that provides or aids in providing an optimal treatment course, where more than one treatment course is available, and information that provides a likelihood of remission or disease-free survival after treatment.

Based on the information provided, a medical professional (e.g., a physician) can optionally design and/or implement a treatment plan. For example, if the subject is diagnosed with a cancerous lesion that is not readily apparent to the naked eye but that has boundaries observable in the hyperspectral/multi spectral medical image, the treatment plan may call for the excision of the lesion based on the boundaries shown in the hyperspectral/multispectral medical image.

In some embodiments, hyperspectral/multispectral images of a subject, or ROI thereof, are taken at a single time point, to evaluate the subject at that particular point in time. In other embodiments, multiple hyperspectral/multispectral images of a subject, or ROI thereof, are taken over a period of time, for example, separated by a minute, hour, day, week, month, year, or decade, to monitor, for example, the overall health of the subject, progression of a medical condition (e.g., progression of a disease), regression of a medical condition, the efficacy of a treatment plan, or to proactively monitor the subject for a medical condition.

For example, in one embodiment, the feet of a subject diagnosed with diabetes are periodically imaged by hyperspectral/multispectral techniques described herein to monitor for initial signs of the formation of a diabetic foot ulcer, which occur in fifteen percent of all diabepatients (Brem and Tomic-Canic, J Clin Invest. 2007 May; 117(5):1219-22). In varying embodiments, the patient's feet are imaged at least once a week, at least once a month, at least once every three months, at least once every six months, or at least once a year.

IV. Application of Hyperspectral/Mulispectral Medical Imaging

In some embodiments, the present disclosure provides systems and methods for hyperspectral/multispectral medical imaging. These methods are based on distinguishing the different interactions that occur between light at different wavelengths and components of the human body, especially components located in or just under the skin. For example, it is well known that deoxyhemoglobin absorbs a greater amount of light at 700 nm than does water, while water absorbs a much greater amount of light at 1200 nm, as compared to deoxyhemoglobin. By measuring the absorbance of a two-component system consisting of deoxyhemoglobin and water at 700 nm and 1200 nm, the individual contribution of deoxyhemoglobin and water to the absorption of the system, and thus the concentrations of both components, can readily be determined. By extension, the individual components of more complex systems (e.g., human skin) can be determined by measuring the absorption of a plurality of wavelengths of light reflected or backscattered off of the system.

The particular interactions between the various wavelengths of light measured by hyperspectral/multispectral imaging and each individual component of the system (e.g., skin) produces hyperspectral/multispectral signature, when the data is constructed into a hyperspectral/multispectral data cube. Specifically, different regions (e.g., different ROI on a single subject or different ROI from different subjects) interact differently with the light depending on the presence of, for example, a medical condition in the region, the physiological structure of the region, and/or the presence of a chemical in the region. For example, fat, skin, blood, and flesh all interact with various wavelengths of light differently from one another. Similarly, a given type of cancerous lesion interacts with various wavelengths of light differently from normal skin, from non-cancerous lesions, and from other types of cancerous lesions. Likewise, a given chemical that is present (e.g., in the blood, or on the skin) interacts with various wavelengths of light differently from other types of chemicals. Thus, the light obtained from each illuminated region of a subject has a spectral signature based on the characteristics of the region, which signature contains medical information about that region.

For example, the structure of skin, while complex, can be approximated as two separate and structurally different layers, namely the epidermis and dermis. These two layers have very different scattering and absorption properties due to differences of composition. The epidermis is the outer layer of skin. It has specialized cells called melanocytes that produce melanin pigments. Light is primarily absorbed in the epidermis, while scattering in the epidermis is considered negligible. For further details, see G. H. Findlay, "Blue Skin," British Journal of Dermatology 83(1), 127-134 (1970), the content of which is incorporated herein by reference in its entirety for all purposes.

The dermis has a dense collection of collagen fibers and blood vessels, and its optical properties are very different from that of the epidermis. Absorption of light of a bloodless dermis is negligible. However, blood-born pigments like oxy- and deoxy-hemoglobin and water are major absorbers of light in the dermis. Scattering by the collagen fibers and absorption due to chromophores in the dermis determine the depth of penetration of light through skin.

Light used to illuminate the surface of a subject will penetrate into the skin. The extent to which the light penetrates will depend upon the wavelength of the particular radiation. For example, with respect to visible light, the longer the wavelength, the farther the light will penetrate into the skin. For example, only about 32% of 400 nm violet light penetrates into the dermis of human skin, while greater than 85% of 700 nm red light penetrates into the dermis or beyond (see, Capinera J. L., *Encyclopedia of Entomology*, $2^{nd}$ Edition, Springer Science (2008) at page 2854, the content of which is hereby incorporated herein by reference in its entirety for all purposes). For purposes of the present disclosure, when referring to "illuminating a tissue," "reflecting light off of the surface," and the like, it is meant that radiation of a suitable wavelength for detection is backscattered from a tissue of a subject, regardless of the distance into the subject the light travels. For example, certain wavelengths of infra-red radiation penetrate below the surface of the skin, thus illuminating the tissue below the surface of the subject.

Briefly, light from the illuminator(s) on the systems described herein penetrates the subject's superficial tissue and photons scatter in the tissue, bouncing inside the tissue many times. Some photons are absorbed by oxygenated hemoglobin molecules at a known profile across the spectrum of light. Likewise for photons absorbed by de-oxygenated hemoglobin molecules. The images resolved by the optical detectors consist of the photons of light that scatter back through the skin to the lens subsystem. In this fashion, the images represent the light that is not absorbed by the various chromophores in the tissue or lost to scattering within the tissue. In some embodiments, light from the illuminators that does not penetrate the surface of the tissue is eliminated by use of polarizers. Likewise, some photons bounce off the surface of the skin into air, like sunlight reflecting off a lake.

Accordingly, different wavelengths of light may be used to examine different depths of a subject's skin tissue. Generally, high frequency, short-wavelength visible light is useful for investigating elements present in the epidermis, while lower frequency, long-wavelength visible light is useful for investigating both the epidermis and dermis. Furthermore, certain infra-red wavelengths are useful for investigating the epidermis, dermis, and subcutaneous tissues.

In the visible and near-infrared (VNIR) spectral range and at low intensity irradiance, and when thermal effects are negligible, major light-tissue interactions include reflection, refraction, scattering and absorption. For normal collimated incident radiation, the regular reflection of the skin at the air-tissue interface is typically only around 4%-7% in the 250-3000 nanometer (nm) wavelength range. For further details, see R. R. Anderson and J. A. Parrish, "The optics of human skin," Journal of Investigative Dermatology 77(1), 13-19 (1981), the content of which is hereby incorporated by reference in its entirety for all purposes. When neglecting the air-tissue interface reflection and assuming total diffusion of incident light after the stratum corneum layer, the steady state VNIR skin reflectance can be modeled as the light that first survives the absorption of the epidermis, then reflects back toward the epidermis layer due the isotropic scattering in the dermis layer, and then finally emerges out of the skin after going through the epidermis layer again.

Using a two-layer optical model of skin, the overall backscattering can be modeled as:

$$R(\lambda) = T_E^2(\lambda) R_D(\lambda)$$

where $T_E(\lambda)$ is the transmittance of epidermis and $R_D(\lambda)$ is the reflectance of dermis. The transmittance due to the epidermis is squared because the light passes through it twice before emerging out of skin. Assuming the absorption of the epidermis is mainly due to the melanin concentration, the transmittance of the epidermis can be modeled as:

$$T_E(\lambda) = \exp(d_E c_m m(\lambda))$$

where $d_E$ is the depth of the epidermis, cm is the melanin concentration and $m(\lambda)$ is the absorption coefficient function for melanin. For further details, see S. L. Jacques, "Skin optics," Oregon Medical Laser Center News Etc. (1988), the content of which is hereby incorporated herein by reference in its entirety for all purposes. For additional information on modeling reflectance, backscattering, transmittance, absorption, and internal scattering of skin, see, U.S. Patent Application Publication No. 2009/0326383 to Barnes et al., the content of which is hereby incorporated herein by reference in its entirety for all purposes.

The value of a tissue's (e.g., skin) backscattering as a function of wavelength, $R(\lambda)$, can be used to obtain medical information about the tissue and its underlying structures. For example, when skin cancers like basal cell carcinoma (BCC), squamous cell carcinoma (SCC), and malignant melanoma (MM) grow in the skin, the molecular structure of the affected skin changes. Malignant melanoma is a cancer that begins in the melanocytes present in the epidermis layer. For further details, see "Melanoma Skin Cancer," American Cancer Society (2005), the content of which is hereby incorporated herein by reference in its entirety for all purposes. Most melanoma cells produce melanin that in turn changes the backscattering characteristics as a function of wavelength $R(\lambda)$ of the affected skin. Squamous and basal cells are also present in the epidermis layer. The outermost layer of the epidermis is called the stratum corneum. Below it are layers of squamous cells. The lowest part of the epidermis, the basal layer, is formed by basal cells. Both squamous and basal cell carcinomas produce certain viral proteins that interact with the growth-regulating proteins of normal skin cells. The abnormal cell growth then changes the epidermis optical scattering characteristics and consequently the skin backscattering properties as a function of wavelength $R(\lambda)$. Thus, information about different skin conditions (e.g., normal skin, benign skin lesions and skin cancers) can be obtained by characterizing the backscattering $R(\lambda)$ from the tissue.

Accordingly, the systems and methods described herein can be used to diagnose and characterize a wide variety of medical conditions. In one embodiment, the concentration of one or more skin or blood component is determined in order to evaluate a medical condition in a patient. Non-limiting examples of components useful for medical evaluation include: deoxyhemoglobin levels, oxyhemoglobin levels, total hemoglobin levels, oxygen saturation, oxygen perfusion, hydration levels, total hematocrit levels, melanin levels, collagen levels, and bilirubin levels. Likewise, the pattern, gradient, or change over time of a skin or blood component can be used to provide information on the medical condition of the patient.

Non-limiting examples of conditions that can be evaluated by hyperspectral/multispectral imaging, include: tissue ischemia, ulcer formation, ulcer progression, venous stasis, venous ulcer disease, infection, shock, cardiac decompensation, respiratory insufficiency, hypovolemia, the progression of diabetes, congestive heart failure, sepsis, dehydration, hemorrhage, hypertension, exposure to a chemical or biological agent, and an inflammatory response.

In one embodiment, the systems and methods described herein are used to evaluate tissue oximetery and correspondingly, medical conditions relating to patient health derived from oxygen measurements in the superficial vasculature. In certain embodiments, the systems and methods described herein allow for the measurement of oxygenated hemoglobin, deoxygenated hemoglobin, oxygen saturation, and oxygen perfusion. Processing of these data provide information to assist a physician with, for example, diagnosis, prognosis, assignment of treatment, assignment of surgery, and the execution of surgery for conditions such as critical limb ischemia, diabetic foot ulcers, pressure ulcers, peripheral vascular disease, surgical tissue health, etc.

In one embodiment, the systems and methods described herein are used to evaluate diabetic and pressure ulcers. Development of a diabetic foot ulcer is commonly a result of a break in the barrier between the dermis of the skin and the subcutaneous fat that cushions the foot during ambulation. This rupture can lead to increased pressure on the dermis, resulting in tissue ischemia and eventual death, and ultimately manifesting in the form of an ulcer (Frykberg R. G. et al., Diabetes Care 1998; 21(10): 1714-9). Measurement of oxyhemoglobin, deoxyhemoglobin, and/or oxygen saturation levels by hyperspectral/multispectral imaging can provide medical information regarding, for example: a likelihood of ulcer formation at an ROI, diagnosis of an ulcer, identification of boundaries for an ulcer, progression or regression of ulcer formation, a prognosis for healing of an ulcer, the likelihood of amputation resulting from an ulcer. Further information on hyperspectral/multispectral methods for the detection and characterization of ulcers, e.g., diabetic foot ulcers, are found in U.S. Patent Application Publication No. 2007/0038042, and Nouvong A. et al., Diabetes Care. 2009 November; 32(11):2056-61, the contents of which are hereby incorporated herein by reference in their entireties for all purposes.

In one embodiment, the systems and methods described herein are used to evaluate shock in a subject. Clinical presentation of shock is variable from subject to subject. While common indicators for a state of shock include low blood pressure, decreased urine output, and confusion, these symptoms do not manifest in all subjects (Tintinalli J. E., "Emergency Medicine: A Comprehensive Study Guide," New York: McGraw-Hill Companies. pp. 165-172). However, it was found that changes in cutaneous oxygen saturation, an underlying cause of shock, present as pronounced hyperspectral mottling patterns in subjects experiencing hemorrhagic shock (U.S. Patent Application Publication No. 2007/0024946). Accordingly, measurement of oxyhemoglobin, deoxyhemoglobin, and/or oxygen saturation levels by hyperspectral/multispectral imaging can provide medical information regarding, for example: a likelihood of a subject entering a state of shock, diagnosis of a state of shock, progression or regression of a state of shock, and a prognosis for the recovery from a state of shock. In certain embodiments, the shock is hemorrhagic shock, hypovolemic shock, cardiogenic shock, septic shock, anaphylactic shock, or neurogenic shock. Methods for the detection and characterization of shock are found in U.S. Patent Application Publication No. 2007/0024946, the content of which is hereby incorporated herein by reference in its entirety for all purposes.

Further examples of medical conditions that may be diagnosed and/or characterized by the methods and systems of the present disclosure include, but are not limited to: abrasion, alopecia, atrophy, av malformation, battle sign, bullae, burrow, basal cell carcinoma, burn, candidal diaper dermatitis, cat-scratch disease, contact dermatitis, cutaneous larva migrans, cutis marmorata, dermatoma, ecchymosis, ephelides, erythema infectiosum, erythema multiforme, eschar, excoriation, fifth disease, folliculitis, graft vs. host disease, guttate, guttate psoriasis, hand, foot and mouth disease, Henoch-Schonlein purpura, herpes simplex, hives, id reaction, impetigo, insect bite, juvenile rheumatoid arthritis, Kawasaki disease, keloids, keratosis pilaris, Koebner phenomenon, Langerhans cell histiocytosis, leukemia, lichen striatus, lichenification, livedo reticularis, lymphangitis, measles, meningococcemia, molluscum contagiosum, neurofibromatosis, nevus, poison ivy dermatitis, psoriasis, scabies, scarlet fever, scar, seborrheic dermatitis, serum sickness, Shagreen plaque, Stevens-Johnson syndrome, strawberry tongue, swimmers' itch, telangiectasia, tinea capitis, tinea corporis, tuberous sclerosis, urticaria, varicella, varicella zoster, wheal, xanthoma, zosteriform, basal cell carcinoma, squamous cell carcinoma, malignant melanoma, dermatofibrosarcoma protuberans, Merkel cell carcinoma, and Kaposi's sarcoma.

Other examples of medical conditions include, but are not limited to: tissue viability (e.g., whether tissue is dead or living, and/or whether it is predicted to remain living); tissue ischemia; malignant cells or tissues (e.g., delineating malignant from benign tumors, dysplasias, precancerous tissue, metastasis); tissue infection and/or inflammation; and/or the presence of pathogens (e.g., bacterial or viral counts). Some embodiments include differentiating different types of tissue from each other, for example, differentiating bone from flesh, skin, and/or vasculature. Some embodiments exclude the characterization of vasculature.

In yet other embodiments, the systems and methods provided herein can be used during surgery, for example to determine surgical margins, evaluate the appropriateness of surgical margins before or after a resection, evaluate or monitor tissue viability in near-real time or real-time, or to assist in image-guided surgery. For more information on the use of hyperspectral/multispectral imaging during surgery, see, Holzer M. S. et al., J Urol. 2011 August; 186(2):400-4; Gibbs-Strauss S. L. et al., Mol Imaging. 2011 April; 10(2): 91-101; and Panasyuk S. V. et al., Cancer Biol Ther. 2007 March; 6(3):439-46, the contents of which are hereby incorporated herein by reference in their entirety for all purposes.

For more information on the use of hyperspectral/multispectral imaging in medical assessments, see, for example: Chin J. A. et al., J Vasc Surg. 2011 December; 54(6): 1679-88; Khaodhiar L. et al., Diabetes Care 2007; 30:903-910; Zuzak K. J. et al., Anal Chem. 2002 May 1; 74(9): 2021-8; Uhr J. W. et al., Transl Res. 2012 May; 159(5):366-75; Chin M. S. et al., J Biomed Opt. 2012 February; 17(2):026010; Liu Z. et al., Sensors (Basel). 2012; 12(1): 162-74; Zuzak K. J. et al., Anal Chem. 2011 Oct. 1; 83(19):7424-30; Palmer G. M. et al., J Biomed Opt. 2010 November-December; 15(6):066021; Jafari-Saraf and Gordon, Ann Vasc Surg. 2010 August; 24(6):741-6; Akbari H. et al., IEEE Trans Biomed Eng. 2010 August; 57(8):2011-7; Akbari H. et al., Conf Proc IEEE Eng Med Biol Soc. 2009:1461-4; Akbari H. et al., Conf Proc IEEE Eng Med Biol Soc. 2008:1238-41; Chang S. K. et al., Clin Cancer Res. 2008 Jul. 1; 14(13):4146-53; Siddiqi A. M. et al., Cancer. 2008 Feb. 25; 114(1):13-21; Liu Z. et al., Appl Opt. 2007 Dec. 1; 46(34):8328-34; Zhi L. et al., Comput Med Imaging Graph. 2007 December; 31(8):672-8; Khaodhiar L. et al., Diabetes Care. 2007 April; 30(4):903-10; Ferris D. G. et al., J Low Genit Tract Dis. 2001 April; 5(2):65-72; Greenman R. L. et al., Lancet. 2005 Nov. 12; 366(9498):1711-7; Sorg B. S. et al., J Biomed Opt. 2005 July-August; 10(4):44004; Gillies R. et al., and Diabetes Technol Ther. 2003; 5(5):847-55, the contents of which are hereby incorporated herein by reference in their entirety for all purposes.

V. Additional Embodiments

The present disclosure is based, at least in part, on an arrangement of optical elements in a hyperspectral/multispectral imaging system that allow for true co-axial imaging of multiple wavelengths. While the methods and systems for co-axial hyperspectral/multispectral imaging provided herein are particularly well suited for medical imaging and diagnostics, other fields may also benefit from the particular arrangement of optical element described herein.

In one embodiment, the present disclosure provides a hyperspectral/multispectral imaging system for remote sensing. For example, an imaging system comprising an high power objective lens, beam steering element having a plurality of operating modes, and a plurality of optical detectors, most or all of which are covered by an appropriate filter, can be mounted within a satellite. The hyperspectral/multispectral satellite can then be used in, for example: geological surveying, e.g., in the mining and oil industries to search for oil seeps (Ellis J., "Searching for oil seeps and oil-impacted soil with hyperspectral imagery", Earth Observation Magazine, January 2001) or pockets of other mineral resources; agricultural surveying, e.g., monitoring of crops or identification of suitable soil; surveillance, e.g., in military reconnaissance; chemical imaging, e.g., for detecting harmful or toxic agents or chemical emissions; and environmental monitoring; e.g., monitoring levels of chemicals in the atmosphere and sub-atmospheric regions.

Additionally, the low maximum power requirements of the hyperspectral/multispectral imaging systems described herein make these devices well suited for other portable applications. For example, as a handheld device used on the battlefield to quickly determine the status of a wounded soldier or detect the presence of a chemical agent. For additional information on the use of hyperspectral/multispectral imaging for triage or other battlefield embodiments, see, U.S. Patent Publication No. 2007/0024946, the content of which is hereby incorporated by reference in its entirety for all purposes.

In another embodiment, a portable hyperspectral/multispectral device, as described herein, can be used to detect harmful emissions, identify chemical spills, or otherwise identify unsafe working conditions, e.g., at a factory, refinery, or chemical plant. In certain embodiments, a hyperspectral/multispectral imaging system may be affixed on a wall, ceiling, post, etc., at a plant or factory to continuously monitor conditions of the atmosphere for safe working conditions.

In another embodiment, a portable hyperspectral/multispectral device, as described herein, can be used for forensic analysis. In some embodiments, the hyperspectral/multispectral methods and systems provided herein can be used, for example: to determine the time of death based on change in cellular chemistry analyzed by the imager; evaluate the proximity of a gunshot based on residue left on target; determine the severity of blunt trauma; determine whether oxygen deprivation occurred pre- or post-mortem; evaluate drug status; identify the location and composition of body fluids present at a crime scene; determine if an injury is old or new; make field assessments; locate evidence and provide in-situ evaluation (e.g., the identification of brass casings over a large area); determine the location of man-made objects; evaluate machined surfaces having varying polarization and spectral responses, analyze bodily fluids spread over a large area; identify a point of impact; evaluate an entire incident scene (as opposed to sampling of individual points within the scene), identify different hairs for DNA analysis; locate and separate out of hairs in a carpet; and analyze chemical residues present on a surface or subject (e.g., gun powder). For additional information on the use of hyperspectral/multispectral imaging in forensics, see U.S.

Pat. No. 6,640,132 to Freeman and Hopmeier, the content of which is hereby incorporated herein by reference in its entirety for all purposes.

Aspects of the disclosed methodologies can be implemented as a computer program product that includes a computer program mechanism embedded in a non-transitory computer-readable storage medium. Further, any of the methods disclosed herein can be implemented in one or more computers or other forms of apparatus. Further still, any of the methods disclosed herein can be implemented in one or more computer program products. Some embodiments disclosed herein provide a computer program product that encodes any or all of the methods disclosed herein. Such methods can be stored on a CD-ROM, DVD, magnetic disk storage product, or any other computer-readable data or program storage product. Such methods can also be embedded in permanent storage, such as ROM, one or more programmable chips, or one or more application specific integrated circuits (ASICs). Such permanent storage can be localized in a server, 802.11 access point, 802.11 wireless bridge/station, repeater, router, handheld mobile device, laptop computer, desktop computer, or other electronic devices.

Some embodiments provide a computer program product that contains any or all of the program modules shown FIG. 13. These program modules can be stored on a CD-ROM, DVD, magnetic disk storage product, or any other computer-readable data or program storage product. The program modules can also be embedded in permanent storage, such as ROM, one or more programmable chips, or one or more application specific integrated circuits (ASICs). Such permanent storage can be localized in a server, 802.11 access point, 802.11 wireless bridge/station, repeater, router, mobile phone, or other electronic devices.

Figure 16:
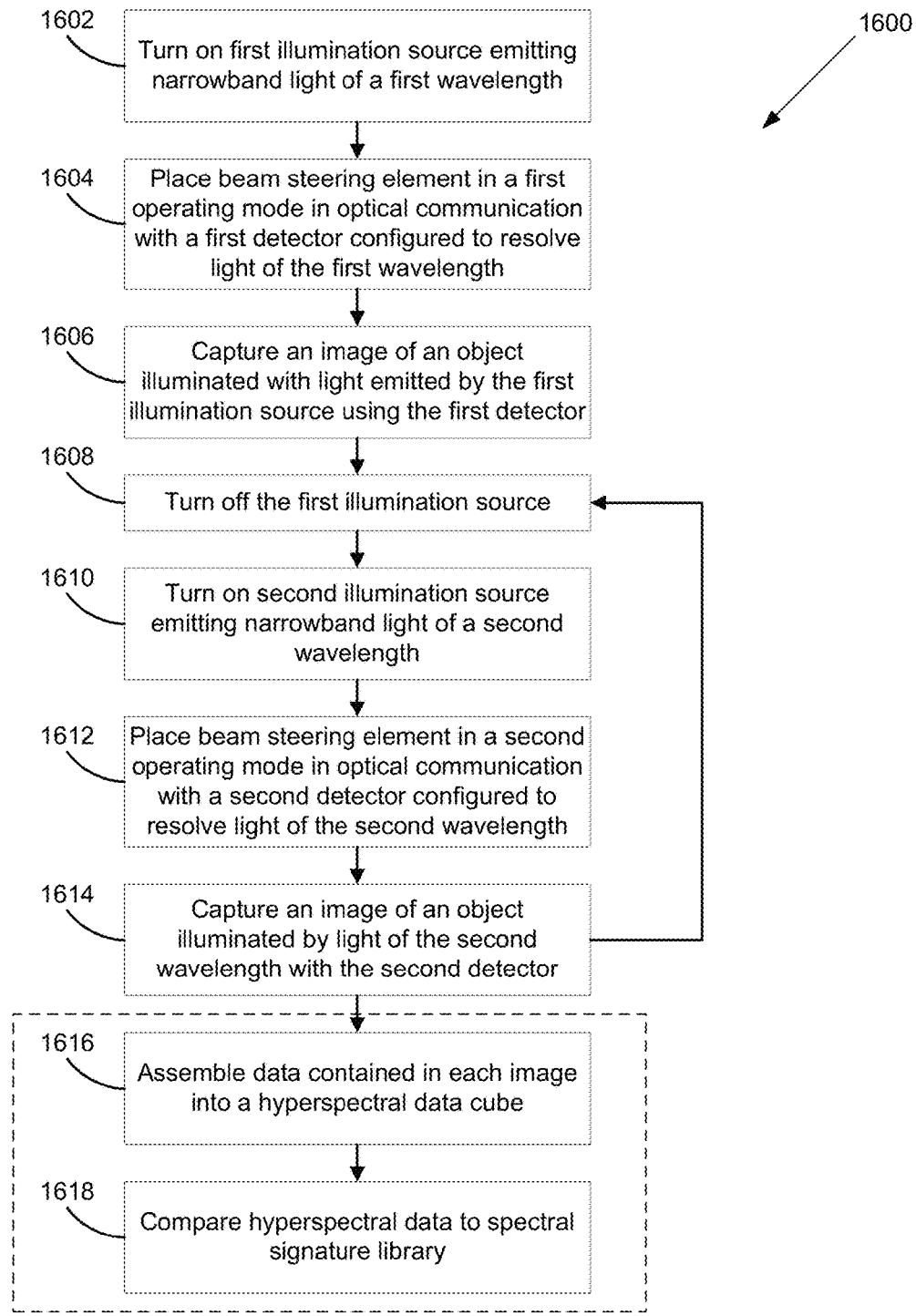
FIG. 16 is a schematic illustration of instructions for collecting and optionally processing hyperspectral/multispectral images, according to some embodiments.

In one aspect, the present disclosure provides a non-transitory computer readable storage medium storing one or more programs executable by a computer for collecting co-axially aligned hyperspectral/multispectral images of an object or subject at a plurality of narrowband wavelengths. As illustrated in FIG. 16, in one embodiment, the program contains instructions for: turning on a first illumination source capable of emitting narrowband light having a first wavelength (1602), placing a beam steering element in a first operating mode in optical communication with a first optical detector configured to resolve narrowband light having the first wavelength (1604); capturing an image of an object or subject illuminated by the light emitted by the first illumination source using the first optical detector (1606); turning off the first illumination source (1608); turning on a second illumination source capable of emitting narrowband light having a second wavelength (1610); placing the beam steering element in a second operating mode in optical communication with a second detector configured to resolve narrowband light having the second wavelength (1612); capturing an image of an object or subject illuminated by the light emitted by the second illumination source using the second optical detector (1614); repeating steps 1608 to 1614 as needed to collect a desired number of images at distinct wavelengths; optionally assembling data contained in each captured image into a hyperspectral data cube; and optionally comparing the data in the hyperspectral data cube to a library of spectral signatures associated with one or more medical conditions, as described herein.

In certain embodiments, the program further comprises instructions for performing at least one of: adjusting the brightness of an acquired image, adjusting the contrast of an acquired image, removing an artifact from an acquired image, cropping an acquired image, processing one or more sub-pixels of an acquired image, compressing the size of an acquired image, assembling a plurality of acquired images into a spectral hypercube, transforming a spectral hypercube assembled from the plurality of acquired digital images, formatting data contained within an acquired image, and encrypting data contained within an acquired image.

In other embodiments, additional programs are provided for operating hyperspectral imaging systems and collecting hyperspectral data, as described herein. For example, in some embodiments, the programs include instructions for illuminating multiple light sources simultaneously, collecting multiple images using multiple optical detectors simultaneously, controlling MEMS mirror or MEMS micromirror arrays, collecting images in line scanning operational modes, etc.

REFERENCES

All references cited herein are hereby incorporated by reference herein in their entirety and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments described herein are offered by way of example only, and the application is to be limited only by the terms of the appended claims, along with the full scope of equivalents to which the claims are entitled.

What is claimed:

1. A method for forming a hyperspectral/multispectral image of a region of a tissue using an imaging system having a plurality of 2-dimensional optical detectors, the hyperspectral/multispectral image comprising a plurality of sub-images, wherein each respective sub-image in the plurality of sub-images is acquired of the region of the tissue at a corresponding wavelength band in a plurality of wavelength bands, the method comprising:

acquiring, using a first 2-dimensional optical detector in the plurality of 2-dimensional optical detectors of the imaging system, a first sub-image in the plurality of sub-images of the region of the tissue at a first wavelength band in the plurality of wavelength bands at a corresponding first minimum exposure time in a plurality of minimum exposure times; and acquiring, using a second 2-dimensional optical detector in the plurality of 2-dimensional optical detectors of the imaging system, a second sub-image in the plurality of sub-images of the region of the tissue at a second wavelength band in the plurality of wavelength bands at a corresponding second minimum exposure time, wherein, the first and second 2-dimensional optical detectors in the plurality of 2-dimensional optical detectors of the imaging system are discrete optical detectors that are independent from each other and spatially separated from each other, the first and second sub-images are acquired of the same region of the tissue, the plurality of minimum exposure times is determined by identifying baseline minimum exposure times for resolving the plurality of sub-images and adjusting the baseline minimum exposure times based on the plurality of wavelength bands, wherein the first minimum exposure time is determined by adjusting, based on the first wavelength band in the plurality of wavelength bands, a first baseline minimum exposure time identified for resolving the first sub-image in the plurality of sub-images, and the second minimum exposure time is determined by adjusting, based on the second wavelength band in the plurality of wavelength bands, a second baseline minimum exposure time identified for resolving the second sub-image in the plurality of sub-images, the second wavelength band is different than the first wavelength band in the plurality of wavelength bands, and the second minimum exposure time is different than the first minimum exposure time.

2. The method of claim 1, further comprising:
acquiring a third sub-image in the plurality of sub-images at a third wavelength band in the plurality of wavelength bands at a corresponding third minimum exposure time in a plurality of minimum exposure times, wherein the third minimum exposure time is different than the first minimum exposure time and the second minimum exposure time.

3. The method of claim 1, wherein the plurality of minimum exposure times is further determined by:
identifying at least one factor affecting one or more minimum baseline exposure times; and
adjusting the baseline minimum exposure times based on the identified factors, thereby determining the plurality of minimum exposure times.

4. The method of claim 3, wherein the at least one factor affecting one or more baseline minimum exposure times includes illumination provided by a device used to acquire the hyperspectral/multispectral image.

5. The method of claim 3, wherein the at least one factor affecting one or more baseline minimum exposure times includes ambient light.

6. The method of claim 3, wherein the at least one factor affecting one or more minimum exposure times includes a concentration of melanin in the tissue.

7. The method of claim 1, wherein the baseline minimum exposure times are based on baseline illumination of the tissue.

8. The method of claim 1, wherein the baseline minimum exposure times are based on the sensitivity of an optical detector acquiring the image.

9. The method of claim 1, wherein the plurality of optical detectors comprises at least four optical detectors.

10. The method of claim 1, wherein each optical detector in the plurality of optical detectors is used for detecting a different wavelength band of light.

11. The method of claim 1, wherein each optical detector in the plurality of optical detectors is covered with a different band-pass filter.

12. A non-transitory computer-readable storage medium storing one or more programs executable by an imaging system with one or more processing units to execute the one or more programs and an optical acquisition system to acquire a hyperspectral/multispectral image of a region of a tissue, the hyperspectral/multispectral image comprising a plurality of sub-images, wherein each respective sub-image in the plurality of sub-images is acquired of the region of the tissue at a corresponding wavelength band in a plurality of wavelength bands, the optical acquisition system comprising a plurality of 2-dimensional optical detectors including a first 2-dimensional optical detector and a second 2-dimensional optical detector, the one or more programs comprising instructions to cause the imaging system to:

acquire a first sub-image in the plurality of sub-images at a first wavelength band in the plurality of wavelength bands at a corresponding first minimum exposure time in a plurality of minimum exposure times using the first 2-dimensional optical detector in the plurality of 2-dimensional optical detectors; and acquire a second sub-image in the plurality of sub-images at a second wavelength band in the plurality of wavelength bands at a corresponding second minimum exposure time using the second 2-dimensional optical detector in the plurality of 2-dimensional optical detectors, wherein the first and second 2-dimensional optical detectors in the plurality of 2-dimensional optical detectors of the imaging system are discrete optical detectors that are independent from each other and spatially separated from each other, the first and second sub-images are acquired of the same region of the tissue, the plurality of minimum exposure times is determined by identifying baseline minimum exposure times for resolving the plurality of sub-images and adjusting the baseline minimum exposure times based on the plurality of wavelength bands, wherein the first minimum exposure time is determined by adjusting, based on the first wavelength band in the plurality of wavelength bands, a first baseline minimum exposure time identified for resolving the first sub-image in the plurality of sub-images, and the second minimum exposure time is determined by adjusting, based on the second wavelength band in the plurality of wavelength bands, a second baseline minimum exposure time identified for resolving the second sub-image in the plurality of sub-images, the second wavelength band is different than the first wavelength band in the plurality of wavelength bands, and the second minimum exposure time is different than the first minimum exposure time.

13. The non-transitory computer readable storage medium of claim 12, the one or more programs comprising instructions further cause the imaging system to:
acquire a third sub-image in the plurality of sub-images at a third wavelength band in the plurality of wavelength bands at a corresponding third minimum exposure time, wherein the third minimum exposure time is different than the first minimum exposure time and the second minimum exposure time.

14. The non-transitory computer readable storage medium of claim 12, the one or more programs comprising instructions further cause the imaging system to:
further determine the plurality of minimum exposure times by:
identifying at least one factor affecting one or more minimum baseline exposure times; and
adjusting the baseline exposure times based on the identified factors, thereby determining the plurality of minimum exposure times.

15. The non-transitory computer-readable storage medium of claim 14, wherein the at least one factor affecting one or more baseline minimum exposure times includes illumination provided by a device used to acquire the hyperspectral/multispectral image.

16. The non-transitory computer-readable storage medium of claim 14, wherein the at least one factor affecting one or more baseline minimum exposure times includes ambient light.

17. The non-transitory computer-readable storage medium of claim 14, wherein the at least one factor affecting one or more baseline minimum exposure times includes a concentration of melanin in the tissue.

18. The non-transitory computer-readable storage medium of claim 12, wherein the baseline minimum exposure times are based on baseline illumination of the tissue.

19. The non-transitory computer-readable storage medium of claim 12, wherein the baseline minimum exposure times are based on the sensitivity of an optical detector acquiring the image.

20. The non-transitory computer-readable storage medium of claim 12, wherein the plurality of optical detectors comprises at least four optical detectors.

21. The non-transitory computer-readable storage medium of claim 12, wherein each optical detector in the plurality of optical detectors is used for detecting a different wavelength band of light.

22. The non-transitory computer-readable storage medium of claim 12, wherein each optical detector in the plurality of optical detectors is covered with a different band-pass filter.

* * * * *